United States Patent
Chen et al.

(10) Patent No.: US 9,394,268 B2
(45) Date of Patent: Jul. 19, 2016

(54) (E)-1-(5-METHOXY-2,2-DIMETHYL-2H-CHROMEN-8-YL)-3-(4-METHOXYPHENYL) PROP-2-EN-1-ONE AND ANALOGS THEREOF, AS WELL AS PREPARATION METHOD AND USE THEREOF

(75) Inventors: Lijuan Chen, Chengdu (CN); Yuquan Wei, Chengdu (CN)

(73) Assignee: Sichuan University, Sichuan (CN)

( * ) Notice: Subject to any disclaimer, the term of this patent is extended or adjusted under 35 U.S.C. 154(b) by 0 days.

(21) Appl. No.: 14/398,643

(22) PCT Filed: May 25, 2012

(86) PCT No.: PCT/CN2012/076033
§ 371 (c)(1),
(2), (4) Date: Nov. 3, 2014

(87) PCT Pub. No.: WO2013/163835
PCT Pub. Date: Nov. 7, 2013

(65) Prior Publication Data
US 2015/0133659 A1 May 14, 2015

(30) Foreign Application Priority Data
May 3, 2012 (CN) .......................... 2012 1 0134792

(51) Int. Cl.
| C07D 413/00 | (2006.01) |
| C07D 311/74 | (2006.01) |
| C07D 405/06 | (2006.01) |
| C07D 407/06 | (2006.01) |
| C07D 409/06 | (2006.01) |
| C07D 405/10 | (2006.01) |

(Continued)

(52) U.S. Cl.
CPC ............ *C07D 311/74* (2013.01); *C07D 405/06* (2013.01); *C07D 405/10* (2013.01); *C07D 405/12* (2013.01); *C07D 407/06* (2013.01); *C07D 407/12* (2013.01); *C07D 409/06* (2013.01)

(58) Field of Classification Search
CPC .. C07D 311/74; C07D 405/10; C07D 405/12; C07D 405/06; C07D 407/06; C07D 407/12; C07D 409/06
USPC ........................................................ 544/151
See application file for complete search history.

(56) References Cited

PUBLICATIONS

Hongo et al, Melanin Synthesis Inhibitors from Lespedeza cyrtobotrya, J. Nat. Prod., 2009,72, p. 63-71.*

(Continued)

*Primary Examiner* — T. Victor Oh
(74) *Attorney, Agent, or Firm* — Caesar Rivise, PC

(57) ABSTRACT

The present invention relates to millepachine ((E)-1-(5-methoxy-2,2-dimethyl-2H-chromen-8-yl)-3-(4-methoxyphenyl)prop-2-en-1-one) and its analogs. The present invention provides methods for preparing these compounds, pharmaceutical compositions including these compounds, and methods of treating diseases utilizing pharmaceutical compositions including these compounds.

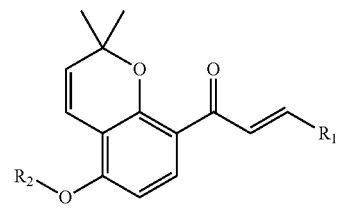

19 Claims, 11 Drawing Sheets

Figure 1:
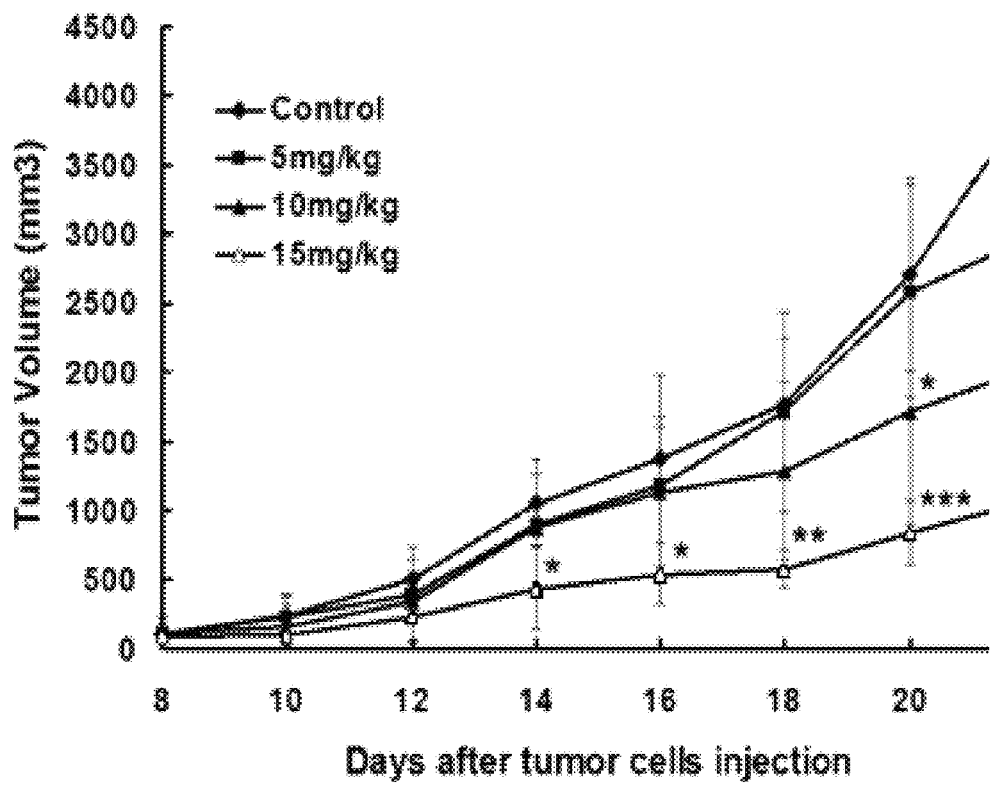

(51) Int. Cl.
*C07D 405/12* (2006.01)
*C07D 407/12* (2006.01)

(56) References Cited

PUBLICATIONS

Maya et al., Melanin Synthesis Inhibitors from Lespedeza cyrtobotrya, J. Nat. Prod., 2009, 72(1), pp. 63-71.

Zhu et al., Progress in Total Synthesis of Natural Benzopranylchalcones, Journal of Guangxi Teachers Education University (Natural Science Edition), Dec. 2004, vol. 21, No. 4, pp. 1-3.
Zhu et al., Review on Natural Benzopranylchalcones Research, Natural Product Research and Development, May 2005, vol. 17, No. 5, pp. 651-657.
International Search Report for PCT/CN2012/076033 dated Feb. 7, 2013.

* cited by examiner

(E)-1-(5-METHOXY-2,2-DIMETHYL-2H-CHROMEN-8-YL)-3-(4-METHOXYPHENYL)PROP-2-EN-1-ONE AND ANALOGS THEREOF, AS WELL AS PREPARATION METHOD AND USE THEREOF

TECHNICAL FIELD

The present invention relates to millepachine ((E)-1-(5-methoxy-2,2-dimethyl-2H-chromen-8-yl)-3-(4-methoxyphenyl)prop-2-en-1-one) and its analogues. The present invention provides methods for preparing these compounds, pharmaceutical compositions comprising these compounds, and methods of treating diseases utilizing pharmaceutical compositions comprising these compounds.

BACKGROUND OF THIS INVENTION

Cancer, also known as a malignant tumor, is a group of diseases involving abnormal cell growth with the potential to invade or spread to other parts of the body. In 2012 about 14.1 million new cases of cancer occurred globally, which caused about 8.2 million deaths or 14.6% of all human deaths. Development of prevention and treatment of cancer drugs will bring benefits to mankind, is of great significance. The important feature of tumor cells is abnormal differentiation, not starting the normal process of apoptosis.

*Millettia pachycarpa* is a perennial climbing shrub belonging to the genus *Millettia*. It is named as Houguojixueteng in Chinese, mainly distributing in Sichuan, Yunnan, Guangdong, Guangxi and Guizhou province in China and is widely used as an antihelminthic, a medication capable of causing the evacuation of parasitic intestinal worms. *M. pachycarpa* is well known to be a rich reservoir of bioactive flavonoids, which exhibited various biological activities including anti-inflammatory, anti-tumor, anti-allergic, anti-microbial and significant cytotoxic effects. Millepachine ((E)-1-(5-methoxy-2,2-dimethyl-2H-chromen-8-yl)-3-(4-methoxyphenyl)prop-2-en-1-one) was isolated as active principles from Chinese herbal medicine *M. pachycarpa* Benth. The novel chalcone was then evaluated for cytotoxic effects against several cancer cell lines. And its apoptosis-inducing effect was tested against HeLa-C3 cells. Both studies showed that millepachine demonstrated significant cytotoxic and apoptotic effects against cancer cells. As a part of continuing search for novel anticancer agents, a series of novel millepachine derivatives have been designed, synthesized and evaluated for antitumor activity by MTT assay.

SUMMARY OF THE INVENTION

In one aspect, the present invention provides compounds of Formula I:

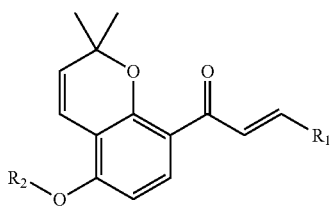

I $R_1$ is aromatic ring with or without substituent, aromatic heterocyclic base with or without a substituent;

$R_2$ is C1-C10 aliphatic hydrocarbon,

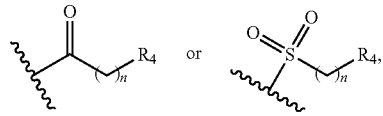

wherein, n=0-4;

$R_4$ is C1-C10 aliphatic hydrocarbon, C3-C10 naphthenic base, aromatic ring with or without substituent, aromatic heterocyclic base with or without a substituent;

C1-C10 aliphatic hydrocarbon is with one to ten carbon atom linear or branched chain, saturated or unsaturated hydrocarbon.

$R_1$ is an optionally substituted group selected from substituent aromatic ring, and the substituents on the aromatic ring are each independently halogen, C1-C5 alkyl halide, —SH, —OH, C1-C4 alkylation amino, cyano, —NO$_2$,

(n=0-4, $R_{16}$ and $R_{17}$ are each independently hydrogen, saturated or unsaturated hydrocarbon with 1 to 6 C atoms), hydroxylamine, carboxyl, trichloromethyl, trifluoromethyl, C1-C10 aliphatic hydrocarbon, C3-C10 naphthenic base, C1-C10 alkoxy, C2-C10 oxygen naphthenic base, C1-C10 alkoxycarbonyl, C1-C10 naphthenic oxygen carbonyl, C1-C10 containing carbonyl carbon chain, C1-C10 containing carbonyl, C1-C10 acetylene carbon chain alkyl amide, C1-C10 amide, C1-C10 aliphatic heterocyclic base, C5-C7 aryl, C3-C5 aromatic heterocyclic base (hetero atom for N or O atom), or

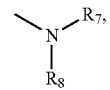

wherein R7 and R8 are each independently hydrogen, C1-C6 aliphatic hydrocarbon and C3-C10 naphthenic base, —OH, C1-C10 carbonyl, C3-C10 containing carbonyl carbon chain, C1-C10 containing carbonyl acetylene carbon chain,

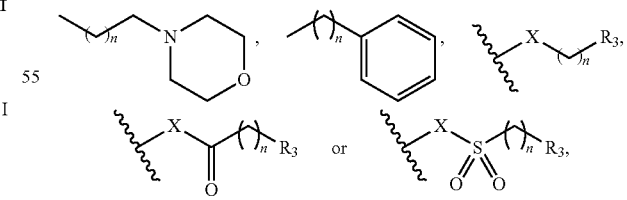

wherein, X is O, S, NH; n=0-4; R3 is linear or branched chain, saturated or unsaturated with 1 to 10 C atoms of hydroxyl, hydroxyl, NH2, halogen, halogen substituted C1-C$_5$ alkyl, C1-C10 naphthenic base, C1-C10 alkoxy, C1-C10 naphthenic oxygen radicals, hydroxylamine, hydroxy amide and carboxyl, trifluoromethyl,

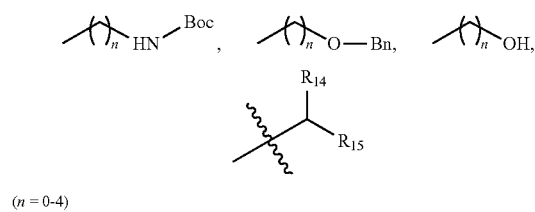

($n$ = 0-4)

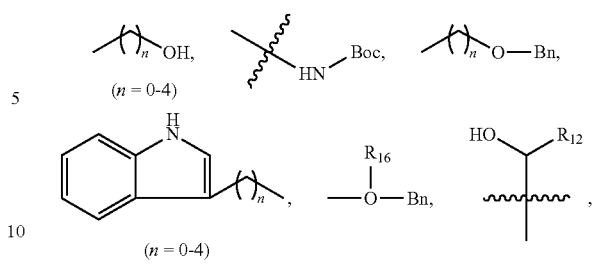

($n$ = 0-4)

($R_{14}$ and $R_{15}$ are each independently hydrogen, saturated or unsaturated hydrocarbon with 1 to 6 C atoms,

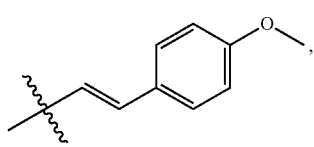 [SMILES: */C=C/c1ccc(OC)cc1]

C3-C10 aliphatic heterocyclic base (heteroatomic for N, O, and S or in one or two), substituted or unsubstituted the aryl, substituted or unsubstituted the aromatic heterocyclic base (hetero atom is N, O, and S or in one or two). Referred to replace the aryl, substituted aromatic heterocyclic base on independent for halogen substituents, —SH, hydroxylamine, hydroxy amide and carboxyl group, three groups, C1-C10 alkyl, C1-C10 naphthenic base, C1-C10 alkoxy, C1-C10 naphthenic base oxygen; or

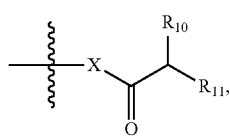

wherein, X is the O, S, NH; $R_{10}$, $R_{11}$ independently for H, linear or branched chain, saturated or unsaturated with 1 to 10 C atoms of hydroxyl, linear or branched chain of hydroxyl with C1 to 10 C atoms, —NH$_2$,

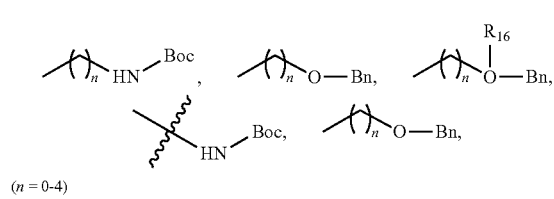

($n$ = 0-4)

substituted or unsubstituted aryl, substituted or unsubstituted the aromatic heterocyclic base (hetero atom is N, O, and S or in one or two). Referred to replace the aryl, substituted aromatic heterocyclic base on independent for halogen substituents, —SH, hydroxylamine, hydroxy amide and carboxyl group, three groups, C1-C10 alkyl, C1-C10 naphthenic base, C1-C10 alkoxy, C1-C10 naphthenic base oxygen. $R_{10}$ and $R_{11}$ an optionally substituted group.

$R_{10}$ and $R_{11}$ are optionally substituted groups independently selected from H, linear or branched chain, saturated or unsaturated hydrocarbon with 1 to 10 C atoms, $R_{12}$ is H, linear or branched chain, saturated or unsaturated hydrocarbon with 1 to 6 C atoms.

The optimization strategy is that the substituted group independently selected from halogen, Halogen substitution of C1-C5, alkyl-OH, —SH, C1-C4 alkylation amino —NO2, CF3, C1-C4 alkyl, C1-C4 alkoxy, C3-C5 aliphatic heterocyclic base (hetero atom is N or O atom), C5-C7 aryl, C3-C5 aromatic heterocyclic base (hetero atom is N or O atom), or

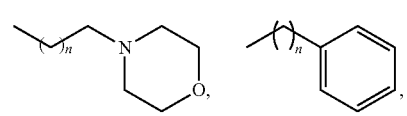

X is O, S, NH; n=0-4.

Further optimization strategy is that $R_7$ and $R_8$ are each independently hydrogen, C1-C6 aliphatic hydrocarbon, C3-C10 naphthenic base, —OH, C1-0C10 carbonyl,

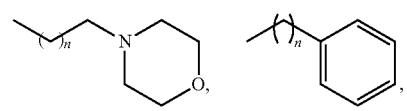

n=0-4.

Further optimization strategy is that $R_7$ and $R_8$ are each independently hydrogen, C1-C6 aliphatic hydrocarbon, C1-C6 naphthenic base,

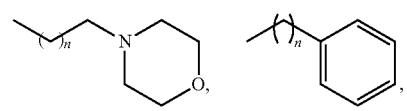

n=0-2.

As the invention optimization strategy, in Formula I as shown in the above, $R_3$ is Linear or branched chain, saturated or unsaturated with one to six carbon atoms of hydroxyl, halogen, halogen substituted C1-C5 alkyl instead of C1-C5, halogen alkyl, hydroxyl, C3-C7 naphthenic base, C1-C5 alkoxy, C1-C4 naphthenic oxygen radicals, hydroxylamine, hydroxy amide and carboxyl group, trifluoromethyl,

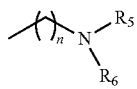

n=0-4 ($R_5$ and $R_6$ are each independently hydrogen, C1-C4 aliphatic alkyl or phenyl), or

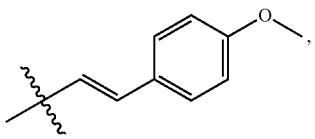 [SMILES: */C=C/c1ccc(OC)cc1]

C3-C7 aliphatic heterocyclic base, C5-C7 to replace or not replaced aryl, C2-C5 to replace or not substituted aromatic heterocyclic base; Among them, aliphatic heterocyclic base, aromatic heterocyclic base of hetero atom is N, O, or S in one or two; Referred to replace the aryl, substituted aromatic heterocyclic base on independent for halogen substituents, C1-C3 alkoxy, trifluoromethyl.

As the invention optimization strategy in Formula I as shown in the above, $R_1$ is substituted phenyl, the substituted group independently selected from C1-C4 alkoxy, C1-C4 alkylation amino, halogen substitution of C1-C5, alkyl —NO2; or

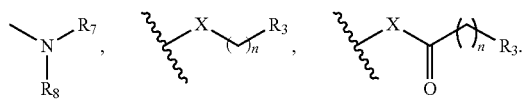

The optimization strategy is that the substituted group independently selected from C1-C4 alkoxy, hydroxyl, halogen, $NO_2$, $NH_2$,

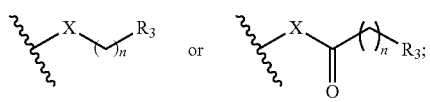

wherein, X is O or NH, n=0-4;

Further optimization strategy is that the substituted group independently selected from C1-C4 alkoxy, hydroxyl, halogen, or

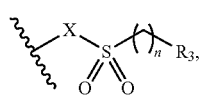

X is O or NH, n=0-4.

Further optimization is that the substituted group independently selected from C1-C4 alkoxy, hydroxyl and halogen,

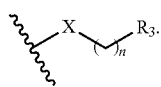

As the invention optimization strategy, in Formula I as shown in the above, $R_1$ is independently

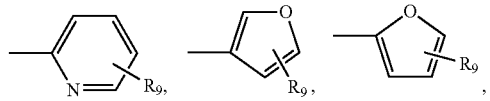

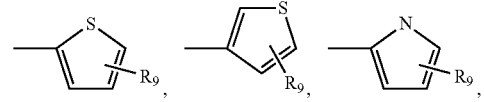

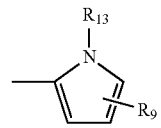

($R_{13}$ is independently hydrogen, Linear or branched chain, saturated or unsaturated hydrocarbon with one to six carbon atoms),

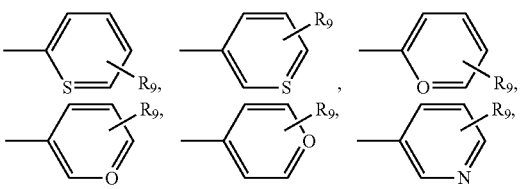

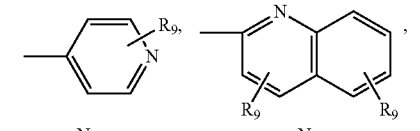

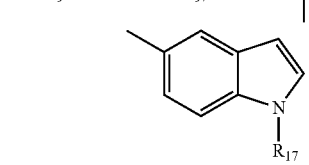

or with substituent aryl; $R_9$ is C1-C4 alkyl or C1-C4 alkoxy; R17 is C1-C4 alkyl or C1-C4 alkoxy or substituted or unsubstituted aromatic heterocyclic base, aromatic heterocyclic skeleton contains 4-10 carbon atoms and 1-2 hetero atoms, described heteroatomic for N, O, and S or in one or two; Or with substituent aryl; R9 for C1-C4 alkyl or C1-C4 alkoxy, aromatic ring on the skeleton with the substituent independently selected from H, —F, Cl, Br, —OH, SH, C1-C4 alkylation amino, $NO_2$, —$NH_2$, $CF_3$, C1-C4 alkyl, C1-C4 alkoxy.

The optimization strategy is that $R_1$ is dependently

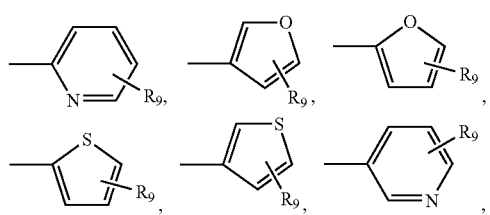

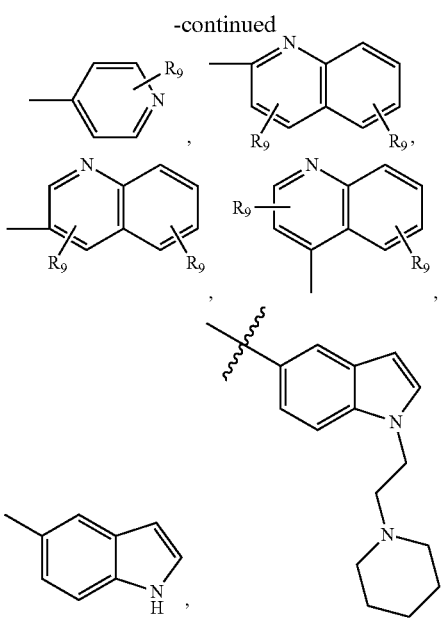

or with substituent aryl; R9 for C1-C4 alkyl or C1-C4 alkoxy, aromatic ring on the skeleton with the substituent independently selected from H, —F, Cl, Br, —OH, SH, C1-C4 alkylation amino, NO$_2$, NH$_2$, CF$_3$, C1-C4 alkyl, C1-C4 alkoxy.

Further optimization strategy is that R$_1$ is dependently

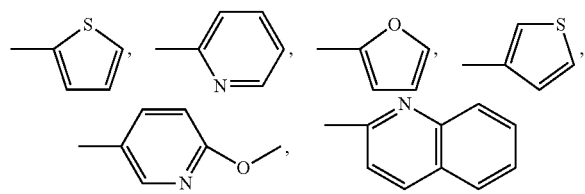

or with substituent aryl.

As the invention optimization strategy, in Formula I as shown in the above, R$_2$ is C1-C10 aliphatic hydrocarbon, C3-C10 naphthenic base,

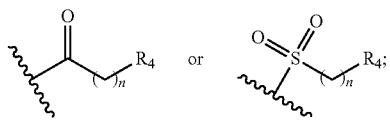

wherein, n=0-4, R$_4$ is dependently C1-C10 aliphatic hydrocarbon, C3-C10 naphthenic base,

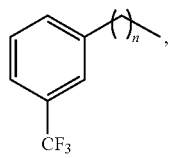

substituted or unsubstituted aryl or aromatic heterocyclic base, replaced aryl or aromatic heterocyclic described base on the substituent independent —OH, CF$_3$, C1-C10 alkyl, C1-C10 alkoxy.

The optimization strategy is that R$_2$ is dependently C1-C4 alkyl,

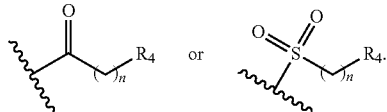

R$_4$ is optionally substituted group independently selected from substituted or unsubstituted aryl, aromatic ring skeleton contains 4-10 carbon atoms, replace the aryl ring skeleton, with one or more substituents on independent for H, halogen substituents, SH, OH, hydroxylamine, hydroxy amide and carboxyl, cyano, NO$_2$, CF$_3$, C1-C10 alkyl, C3-C10 naphthenic base, C1-C10 alkoxy, C1-C10 silane oxygen carbonyl, C1-C10 alkanes amide, C1-C10 alkyl single replace amino,

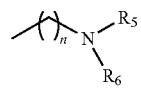

n=0-4 (R5 and R6 are each independently hydrogen, C1-C4 aliphatic alkyl or phenyl), C4-C7 nitrogenous aliphatic heterocyclic and C5-C7 nitrogen aromatic heterocyclic. Further optimization strategy is that R$_4$ is dependently substituted or unsubstituted aromatic heterocyclic base, ring skeleton with 4-6 carbon atoms and 1-2 hetero atoms, described as nitrogen, oxygen or sulfur hetero atoms.

The further optimization strategy is that aromatic heterocyclic base on the ring frame with one or more substituents, independent for H, halogen substituents, SH, —OH, hydroxylamine, hydroxy amide and carboxyl, cyano, NO$_2$, CF$_3$, C1-C10 alkyl, C1-C10 alkoxy, C1-C10 silane oxygen carbonyl, C1-C10 alkyl amide group.

As the invention optimization strategy in Formula I, R$_2$ is C1-C4 alkyl, especially methyl groups.

The structure of Formula II for the millepachine and the derivatives shows as below,

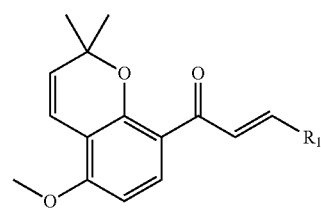

As the invention optimization strategy, R$_1$ is substituted benzene, as shown in the structure of Formula III:

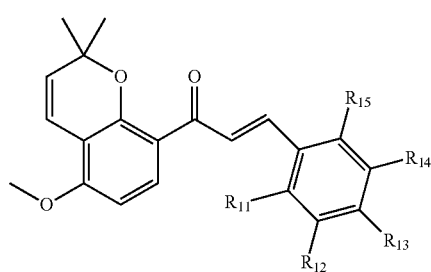

R$_{11}$-R$_{15}$ are independently H, halogen, SH, hydroxylamine, hydroxy amide and carboxyl, C1-C4 alkyl carbonyl oxygen, C1-C4 alkylation amino, OH, C1-C4 alkanes amide, cyano, NO$_2$,

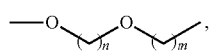

CF$_3$, C1-C4 alkyl, C1-C4 alkoxy, nitrogen heterocyclic nitrogen aromatic heterocyclic, C5-C7 alkyl aromatic ring, double R3 replace amino; Nitrogen heterocyclic contains three to five carbon atoms and 1-2 nitrogen atoms; Nitrogen containing aromatic heterocyclic 2-5 carbon atoms and 1-2 nitrogen atoms; R3 is C1-C4 alkyl or C5-C7 alkyl aromatic ring; N=1-4 m=0-7.

The optimization strategy is that $R_{11}$-$R_{15}$ are independently H, F, Cl, Br, OH, SH, carboxyl, C1-C4 silane oxygen carbonyl, C1-C4 alkylation amino, NO$_2$,

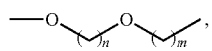

CF$_3$, C1-C4 alkyl, C1-C4 alkoxy, nitrogen heterocyclic nitrogen aromatic heterocyclic, C5-C7 alkyl aromatic ring, double R3 replace amino; Nitrogen heterocyclic contains three to five carbon atoms and 1-2 nitrogen atoms; Nitrogen containing aromatic heterocyclic 2-5 carbon atoms and 1-2 nitrogen atoms; R3 is C1-C4 alkyl or C5-C7 alkyl aromatic ring; N=1-4, m=0-7.

The further optimization strategy is that $R_{11}$-$R_{15}$ are independently H, F, Cl, Br, OH, SH, C1-C4 alkylation amino, NO$_2$,

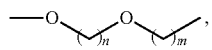

CF$_3$, C1-C4 alkyl, C1-C4 alkoxy, nitrogen heterocyclic nitrogen aromatic heterocyclic, C5-C7 alkyl aromatic ring, double R3 replace amino; Nitrogen heterocyclic contains three to five carbon atoms and 1-2 nitrogen atoms; Nitrogen containing aromatic heterocyclic 2-5 carbon atoms and 1-2 nitrogen atoms; R3 is C1-C4 or alkyl benzene; N=1, m=0-4.

The further optimization strategy is that $R_3$-$R_7$ are independently H, F, Cl, Br, OH, NO$_2$,

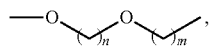

CF$_3$, C1-C4 alkyl, C1-C4 alkoxy, nitrogen heterocyclic nitrogen aromatic heterocyclic, C5-C7 alkyl aromatic ring, double R3 replace amino; Nitrogen heterocyclic contains three to five carbon atoms and 1-2 nitrogen atoms; Nitrogen containing aromatic heterocyclic 2-5 carbon atoms and 1-2 nitrogen atoms; R3 is C1-C4 or alkyl benzene; N=1, m=0-4.

As the invention optimization strategy, $R_1$ in Formula II is a benzene ring with a diethylamine base, as shown in the structure of Formula IV:

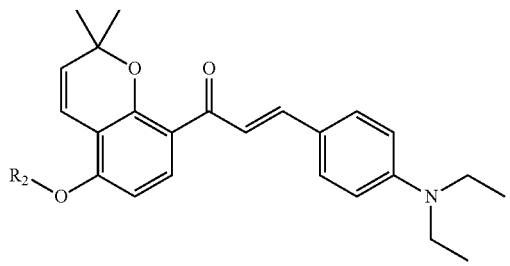

In which, $R_2$ is hydrogen atoms, C1-C6 linear or branched alkyl, C2-C6 alkenyl or alkynyl, with one or more selected from hydroxyl, amino, C1-C3 alkyl halide atom, C3-C6 naphthenic base, aralkyl not replace or various substituted phenyl, aromatic heterocyclic base; C1-C6 linear or branched alkyl ester, with one or more selected from hydroxyl, amino and halogen atom C1-C3 alkyl ester, ring of C3-C6 alkyl esters, aralkyl not replace or various substituted phenyl ester, aromatic heterocyclic base ester; C1-C6 linear or branched chain sulfonic acid ester, with one or more selected from hydroxyl, amino and halogen atom Cl-sulfonic acid ester of C3 and C3-C6 ring alkyl sulfonate, aralkyl not replace or substituted phenyl sulfonic acid ester, aromatic heterocyclic sulfonic acid ester.

The optimization strategy is that $R_1$ in Formula II is a benzene ring with p-methoxyl group, as shown in the structure of Formula V:

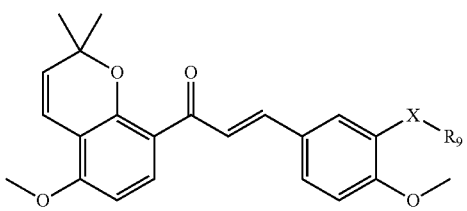

In which,

X is Oxygen, nitrogen, sulfur atoms.

$R_9$ is hydrogen, C1-C6 linear or branched alkyl, C2-C6 alkenyl or alkynyl, with one or more selected from hydroxyl, amino, C1-C3 alkyl halide atom, C3-C6 naphthenic base, aralkyl not replace or various substituted phenyl, aromatic heterocyclic base; C1-C6 linear or branched alkyl ester, with one or more selected from hydroxyl, amino and halogen atom C1-C3 alkyl ester, ring of C3-C6 alkyl esters, aralkyl not replace or various substituted phenyl ester, aromatic heterocyclic base ester; C1-C6 linear or branched chain sulfonic acid ester, with one or more selected from hydroxyl, amino and halogen atom C1-sulfonic acid ester of C3 and C3-C6 ring alkyl sulfonate, aralkyl not replace or substituted phenyl sulfonic acid ester, aromatic heterocyclic base sulfonic acid ester; C3-C6 amino acid base.

In second aspect, the present invention provides the preparation for the compounds of Formula I, II, III, IV, V, the synthetic route show below, Scheme 1,

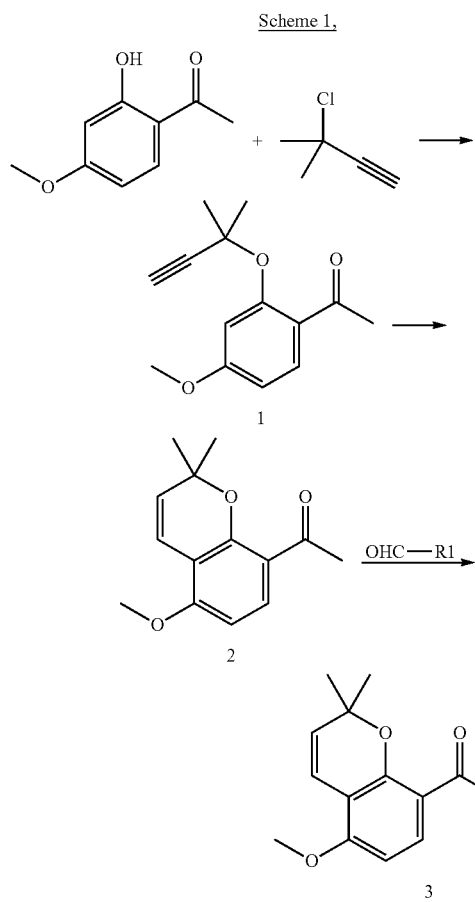

Scheme 2,

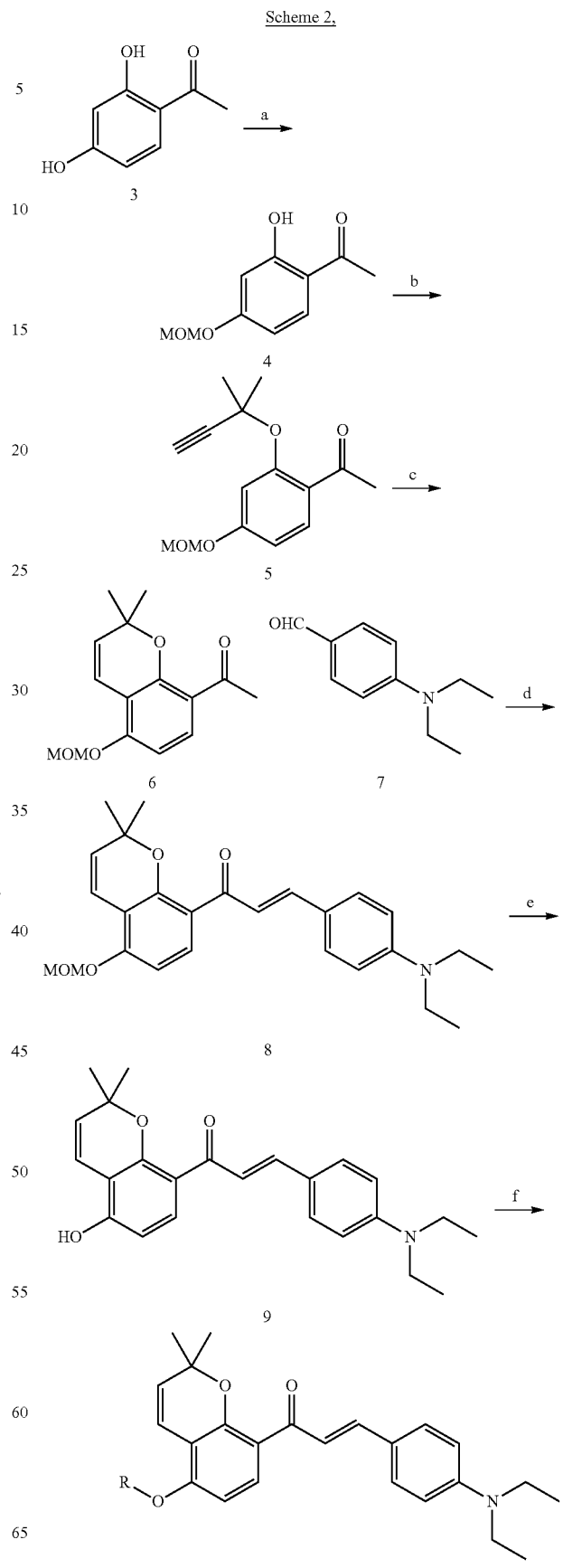

(1) Treatment of paeonol with 3-chloro-3-methyl-1-butyne in the presence of base and catalytic amounts of CuCl$_2$.2H$_2$O proceeded smoothly to afforded 1 in good yield
(2) Compound 1 was upon heating in pyridine at 120° C. for overnight to obtain 2
(3) The chalcone analog 3 was obtained by Claisene-Schmidt condensation of 2 and requisite The base used in Step (1) selected at least one from anhydrous potassium carbonate, Sodium carbonate, sodium hydroxide, potassium hydroxide, sodium hydride;

The reaction of paeonol with 3-chloro-3-methyl-1-butyne was at 0° C.;

The solution used in Step (1) was selected at least one from THF, acetone, DMF, dioxane;

The reaction time in Step (1) was 5-24 h, the temperature was 10-100° C.;

The solution used in Step (2) was selected at least one from DMF, acetate, pyridine and N,N-dimethyl aniline, N,N-diethyl aniline, xylene, toluene.

The reaction time in Step (2) was 5-48 h, the temperature was 20-300° C.;

The solution used in Step (3) was selected at least one from ethanol, methanol;

The reaction time in Step (3) was 12-56 h, the temperature was 10-80° C.;

In which:
(1) Treatment of compound 3 with MOMCl in the presence of base to obtain compound 4;
(2) Treatment of compound 4 with 3-chloro-3-methyl-1-butyne in the presence of base to obtain compound 5;
(3) Reaction compound 5 in the pyridine at 120° C. for overnight to obtain compound 6
(4) To a solution of compound 6 and diethylaminobenzaldehyde in the presence of base to obtain compound 8
(5) Compound 8 was deprotection MOM through a treatment with acid to obtain compound 9;
(6) Compound 9 was reaction with various halogenated, acid, chloride, sulfonyl chloride to obtain target product The base used in Step (1) was selected at least one from potassium carbonate, sodium carbonate, sodium hydroxide, potassium hydroxide, sodium hydride;

The solution used in Step (1) was selected at least one from THF, acetone, DMF, dioxane;

The reaction time in Step (1) was 5-24 h, the temperature was 10-100° C.;

The base used in Step (2) was selected at least one from potassium carbonate, sodium carbonate, sodium hydroxide, potassium hydroxide, sodium hydride;

The solution used in Step (2) selected at least one from DMF, acetate, pyridine and N,N-dimethyl aniline, N,N-diethyl aniline, xylene, toluene.

The reaction time in Step (2) was 5-24 h, the temperature was 10-100° C.;

The solution used in Step (3) was selected at least one from DMF, acetate, pyridine and N,N-dimethyl aniline, N,N-diethyl aniline, xylene, toluene.

The reaction time in Step (3) was 5-48 h, the temperature was 20-300° C.;

The solution used in Step (4) was selected at least one from ethanol, methanol;

The reaction time in Step (4) was 12-56 h, the temperature was 10-80° C.;

The base used in Step (4) was selected at least one from NaOH, KOH, Ba(OH)$_2$;

The acid used in Step (5) was selected at least one from hydrochloric acid, sulfuric acid, nitric acid, p-toluene sulfonic acid, trifluoroacetic acid and acetic acid The solution used in Step (5) was selected at least one from ethyl acetate, methanol, ethanol, methylene chloride, tetrahydrofuran;

The reaction time in Step (5) was 0.1-12 h, the temperature was 10-80° C.;

The base used in Step (6) selected at least one from potassium carbonate, sodium carbonate, sodium hydroxide, potassium hydroxide, sodium hydride;

The solution used in Step (6) selected at least one from THF, acetone, DMF, dioxane, ethyl acetate, methanol, ethanol, methylene chloride.

Scheme 3

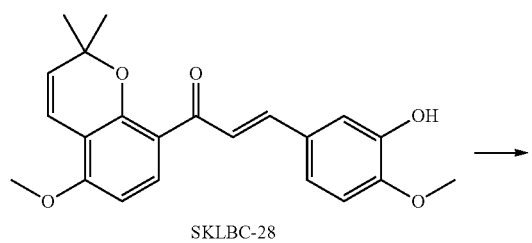

SKLBC-28

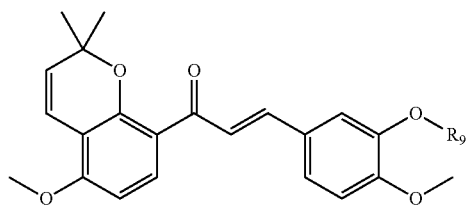

In which:
a: Compound SKLBC-28 was reaction with various halogenated, chloride, acid anhydride to obtain target product;
b: Compound SKLBC-28 was reaction with various carboxylic acids in the presence of condensing agents to obtain target product;

The base used in Step (1a) was selected at least from potassium carbonate, sodium carbonate, sodium hydroxide, potassium hydroxide, sodium hydride, triethylamine, pyridine, diethylamine and DMAP;

The solution used in Step (1a) was selected at least one from THF, acetone, DMF, dioxane, dichloromethane, ethyl acetate;

The reaction time in Step (1a) was 5-24 h, the temperature was 10-100° C.;

The condensing agent was selected at least one from EDCI, DCC;

The solution used in Step (1b) was selected at least one from THF, acetone, DMF, dioxane, dichloromethane, ethyl acetate;

The reaction time in Step (1b) was 5-24 h, the temperature was 10-100° C.;

Scheme 4

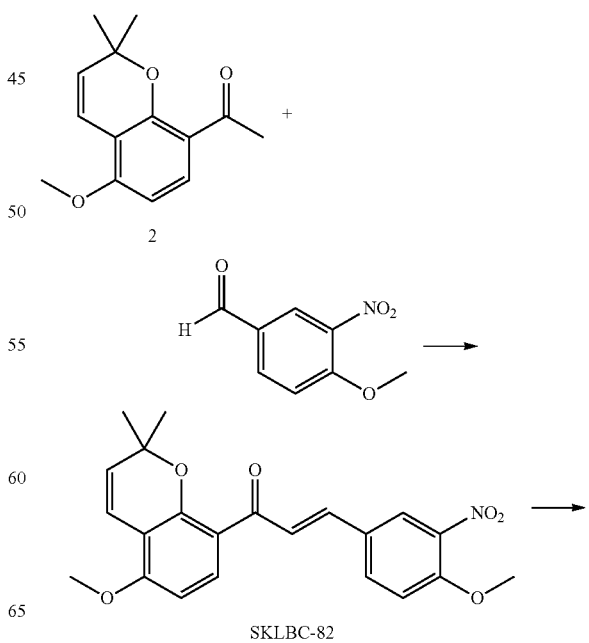

SKLBC-82

-continued

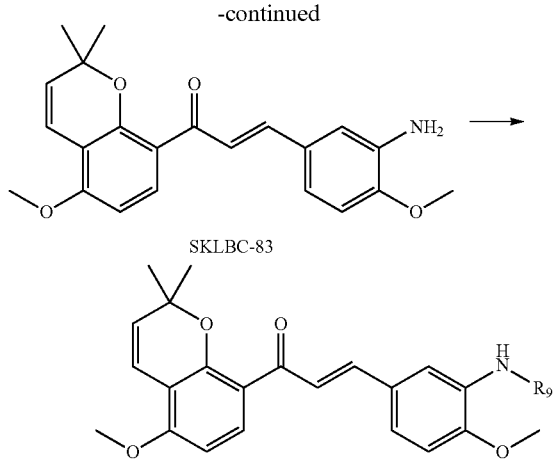

SKLBC-83

(1) To a solution of compound 2 and 4-methoxy-3-nitrobenzene formaldehyde in the presence of base to obtain compound SKLBC-82;
(2) SKLBC-82 was nitro reduction in the presence of reducing agents to obtain compound SKLBC-83;
(3) a: Compound SKLBC-83 was reaction with various halogenated, chloride, acid anhydride to obtain target product;
b: Compound SKLBC-83 was reaction with various carboxylic acids in the presence of condensing agents to obtain target product;

The solution used in Step (1) was selected at least one from ethanol, methanol;

The base used in Step (1) was selected at least one from NaOH, KOH, Ba(OH)$_2$;

The reaction time in Step (1) was 12-56 h, the temperature was 10-80° C.;

The reducing agent in Step (2) was selected at least one from iron powder, stannous chloride, insurance powder, hydrogen;

The solution in Step (2) was selected at least one from methanol, ethanol, propanol, THF, acetone, DMF, dioxane, dichloromethane, ethyl acetate The base used in Step (3a) was selected at least from potassium carbonate, sodium carbonate, sodium hydroxide, potassium hydroxide, sodium hydride, triethylamine, pyridine, diethylamine and DMAP;

The solution used in Step (3a) was selected at least one from THF, acetone, DMF, dioxane, dichloromethane, ethyl acetate;

The reaction time in Step (3a) was 5-24 h, the temperature was 10-100° C.;

The condensing agent was selected at least one from EDCI, DCC;

The solution used in Step 3b) was selected at least one from THF, acetone, DMF, dioxane, dichloromethane, ethyl acetate;

The reaction time in Step (3b) was 5-24 h, the temperature was 10-100° C.

In third aspect, the present invention provides the usage to treated the cancers of those (E)-1-(5-methoxy-2,2-dimethyl-2H-chromen-8-yl)-3-(4-methoxyphenyl)prop-2-en-1-one and the analogues.

Optical choice of antitumor drug are drugs of lung cancer, colon cancer, prostate cancer, ovarian cancer and breast cancer.

The targets of descripted antitumor drugs are hepatocellular carcinoma cell (HePG2), human colon cancer cell (SW480, HCT116), prostate cancer (DU145), ovarian cancer (SK-OV-3), human breast cancer (MDA-MB-231, MDA-MB-468, SKBR3), human lung cancer (A549).

The combination of drugs, are the combination with I, II, II, and IV of (E)-1-(5-methoxy-2,2-dimethyl-2H-chromen-8-yl)-3-(4-methoxyphenyl)prop-2-en-1-one and the analogues, and pharmaceutical acceptable carrier.

FIGURE LEGENDS

FIG. 1 presents the tumor volume time curve of the antitumor effect of Millepachine at variable doses in B16-tumor bearing mice model.

Figure 2:
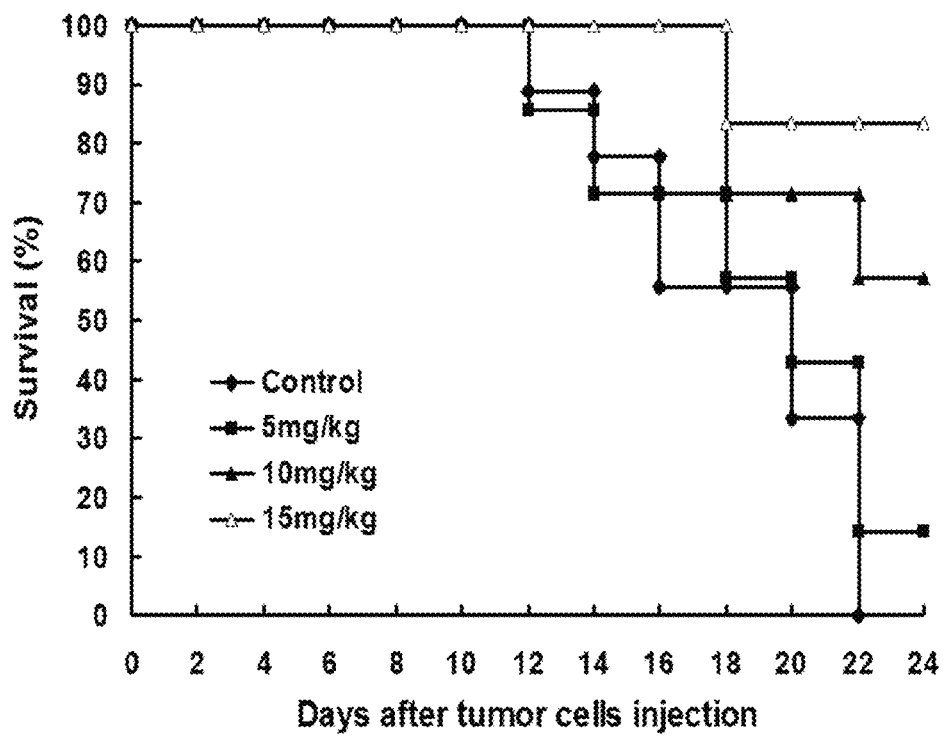

FIG. 2 presents the survival rate of the B16-tumor bearing mice treated by variable doses of Millepachine.

Figure 3:
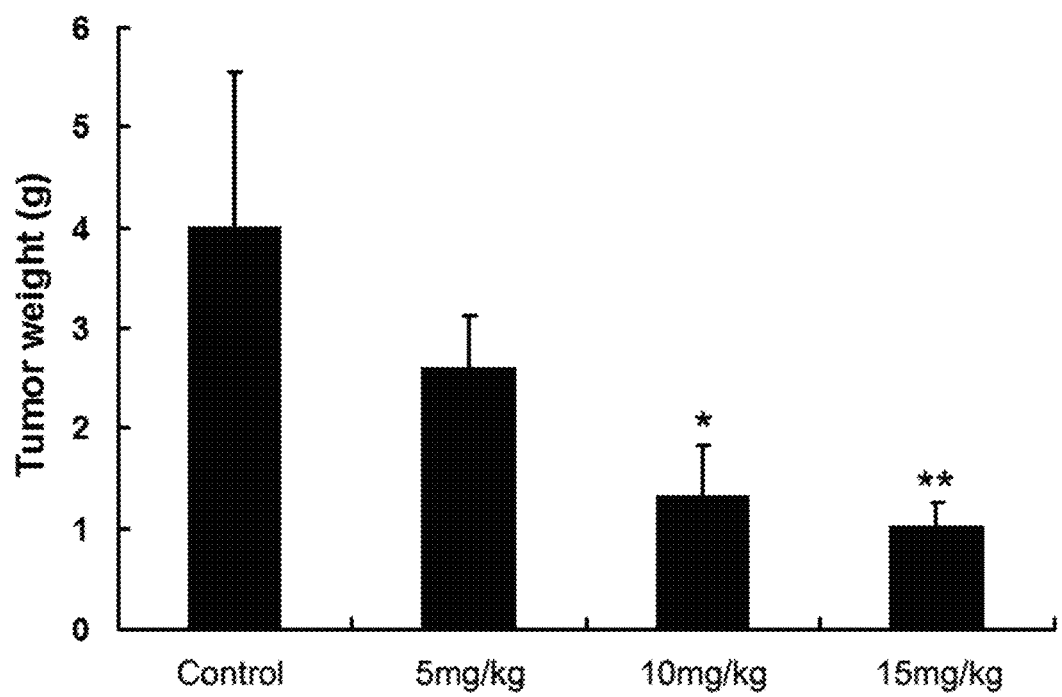

FIG. 3 presents the comparison of tumor weight of the B16-tumor bearing mice treated by variable doses of Millepachine.

Figure 4:
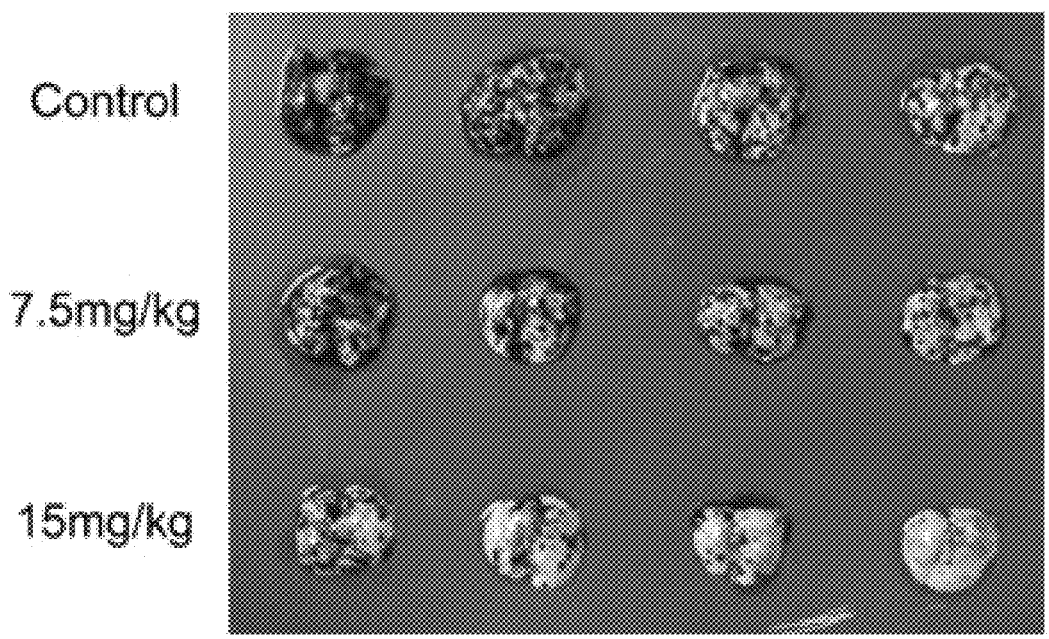

FIG. 4 presents the photo of tumor lung-metastasis. Millepachine dose-dependently inhibited B16 lung metastasis.

Figure 5:
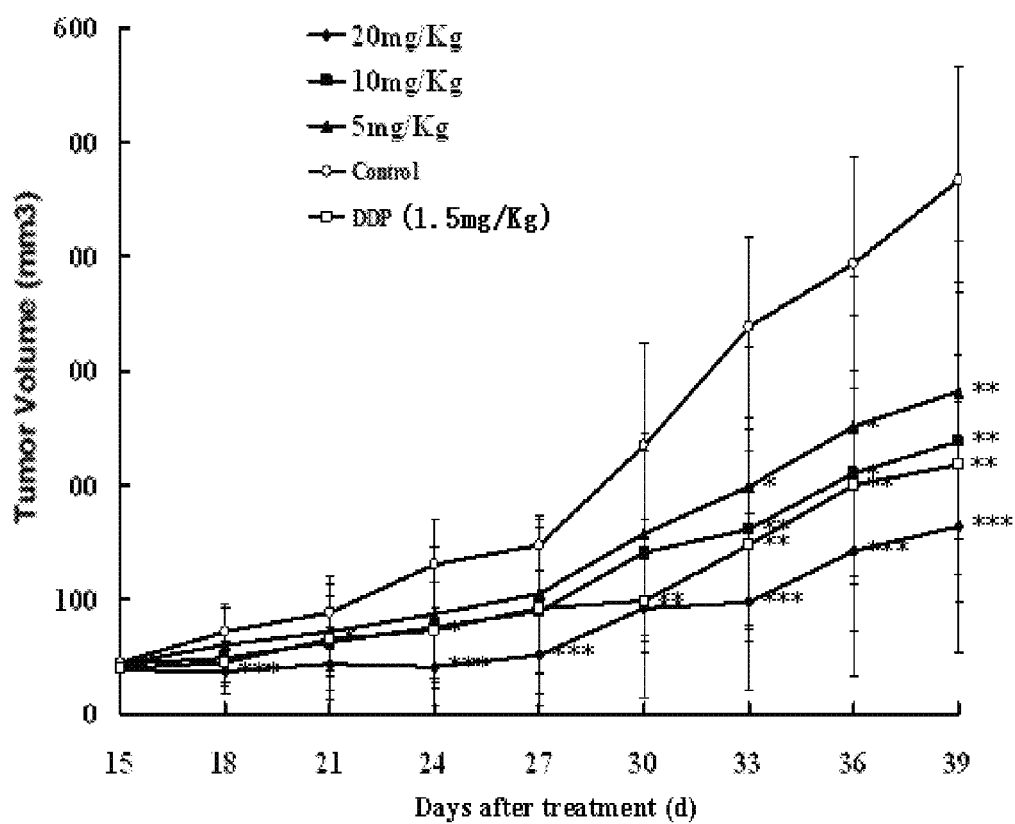

FIG. 5 presents the tumor volume time curve of the control groups and SKLBC-9 variable-dose treatment groups in human lung cancer A549 xenograft model.

Figure 6:
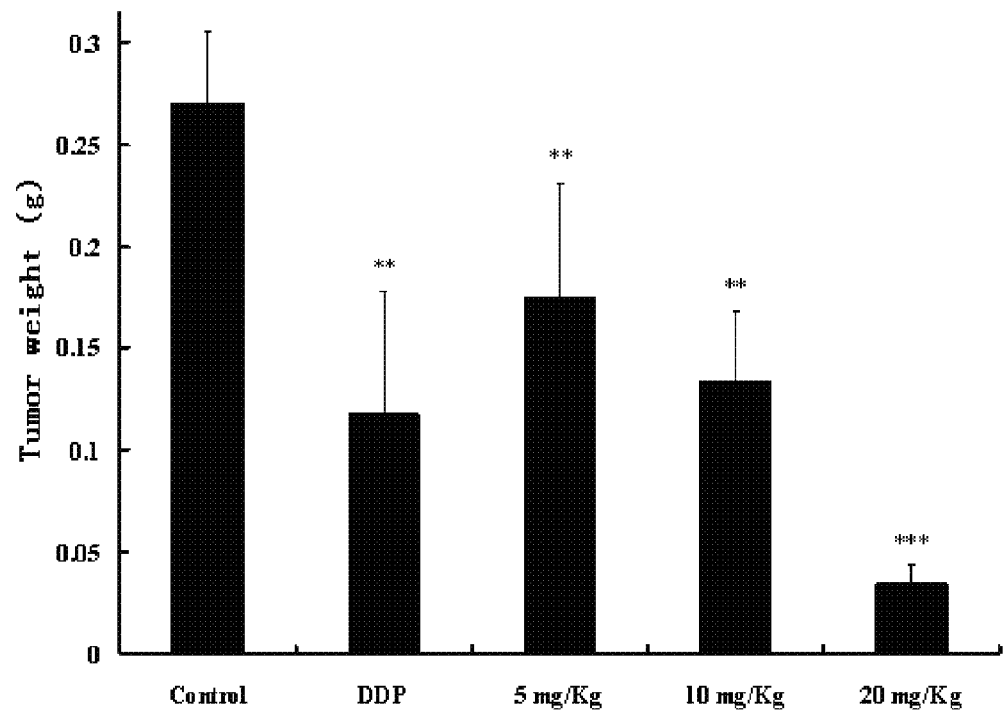

FIG. 6 presents the comparison of tumor weight of the A549 xenograft mice treated by variable doses of SKLBC-9.

Figure 7:
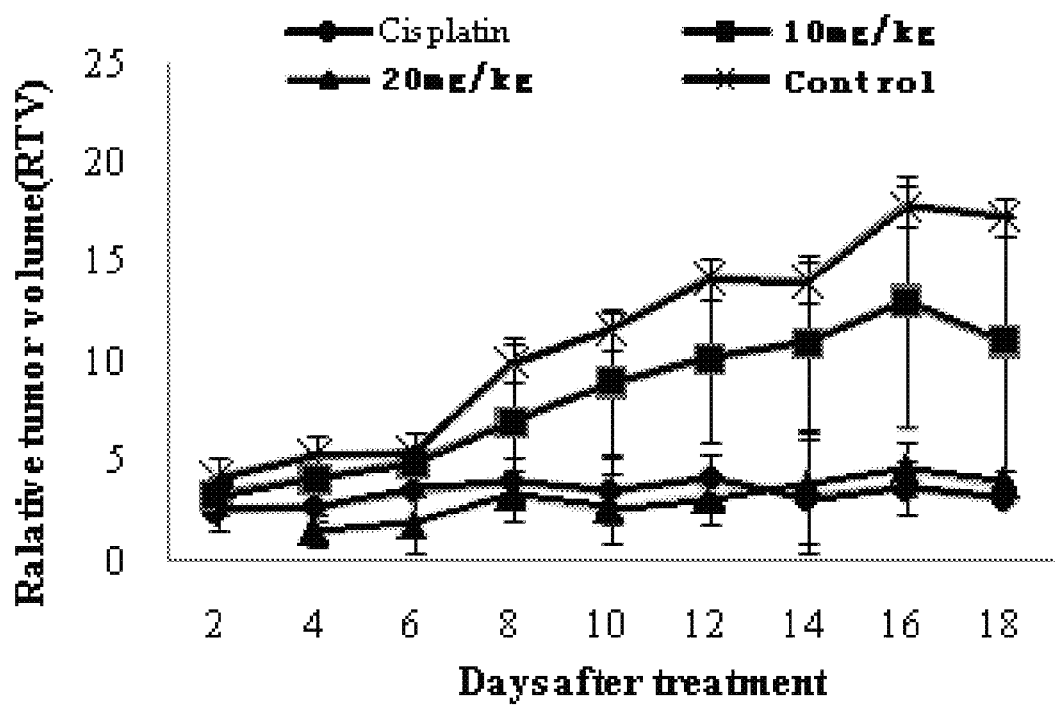

FIG. 7 presents the relative tumor volume (RTV) time curve of the control groups and SKLBC-9 variable-dose treatment groups in human lung cancer SPC-A1 xenograft model.

Figure 8:
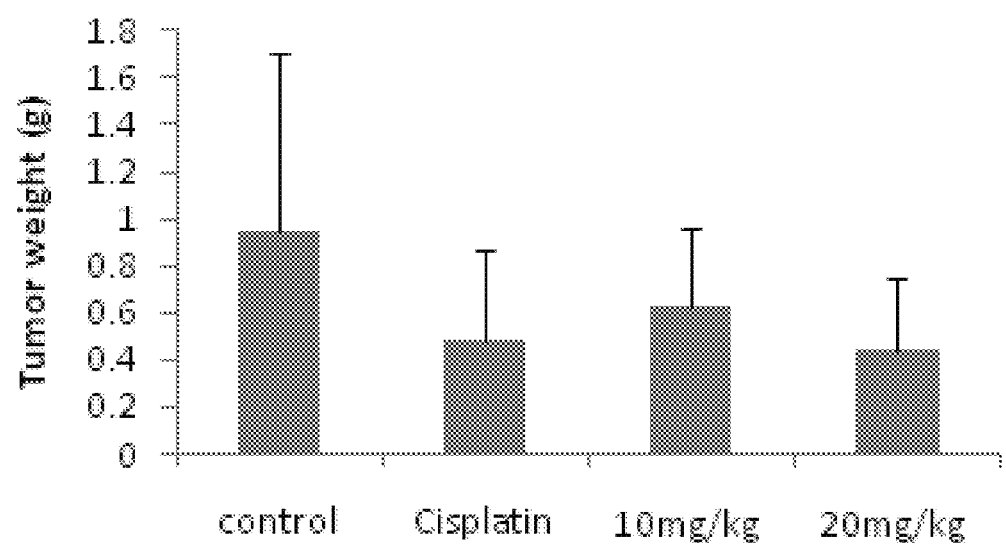

FIG. 8 presents the comparison of tumor weight of the SPC-A1 xenograft mice treated by variable doses of SKLBC-9.

Figure 9:
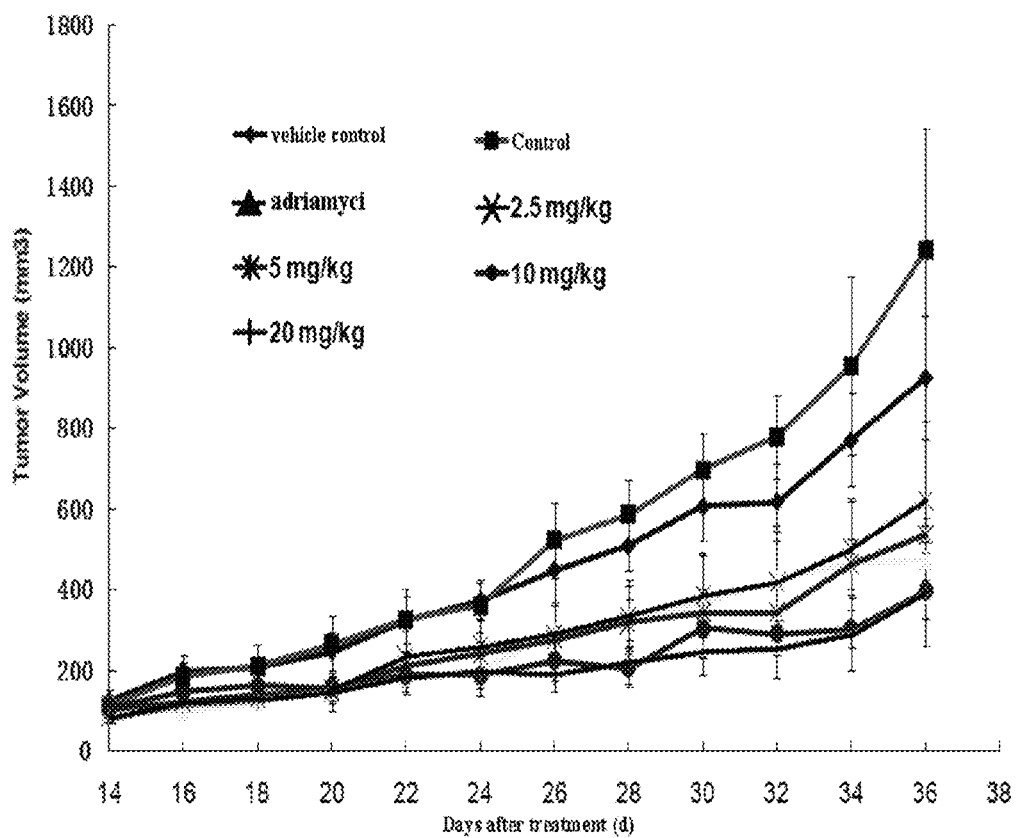

FIG. 9 presents the tumor volume time curve of the control groups and SKLBC-45 variable-dose treatment groups in human hepatocarcinoma HepG2 xenograft model.

Figure 10:
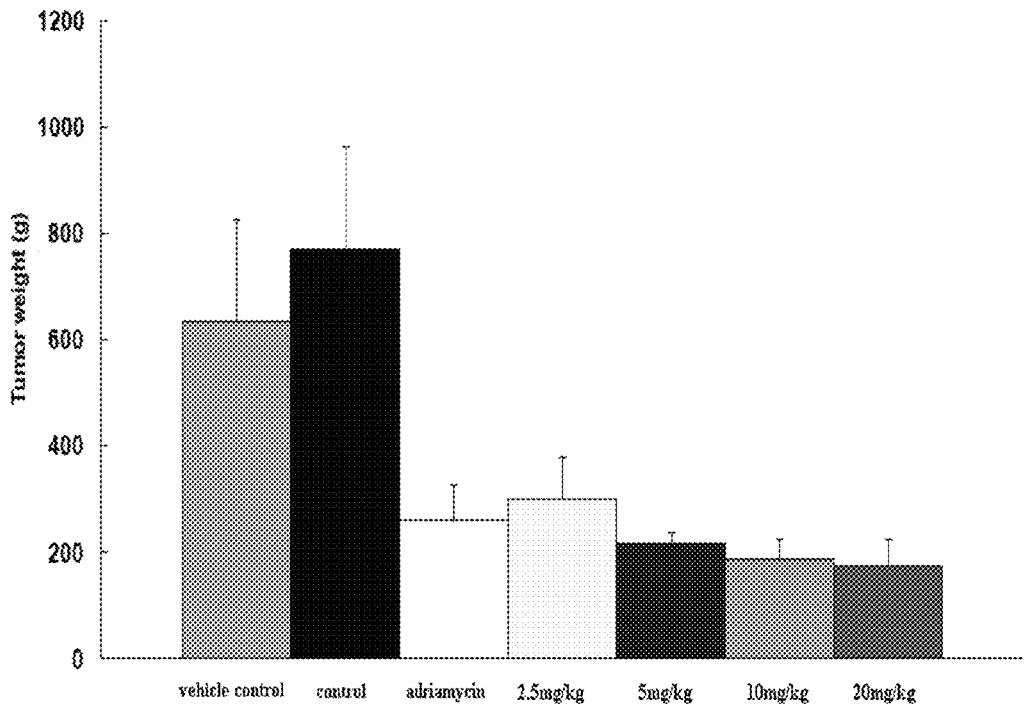

FIG. 10 presents the comparison of tumor weight of the HepG2 xenograft mice treated by the controls and variable doses of SKLBC-45.

Figure 11:
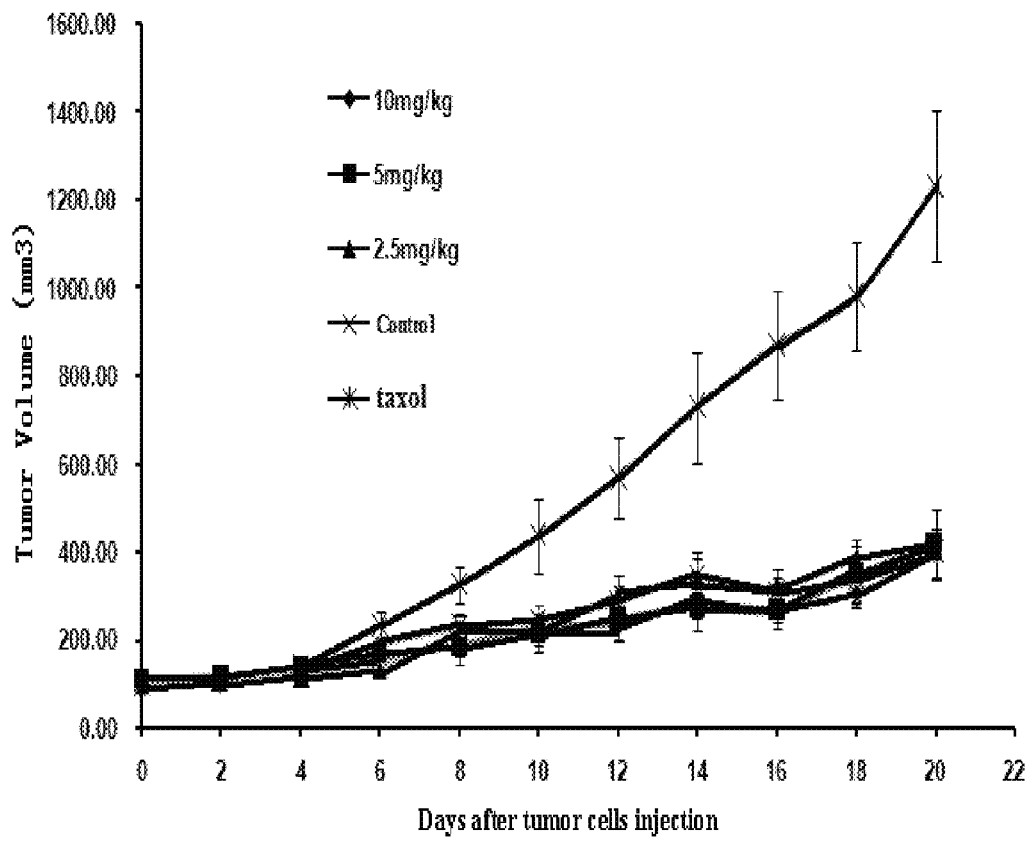

FIG. 11 presents the tumor volume time curve of the control groups and SKLBC-76 variable-dose treatment groups in human hepatocarcinoma HepG2 xenograft model.

Figure 12:
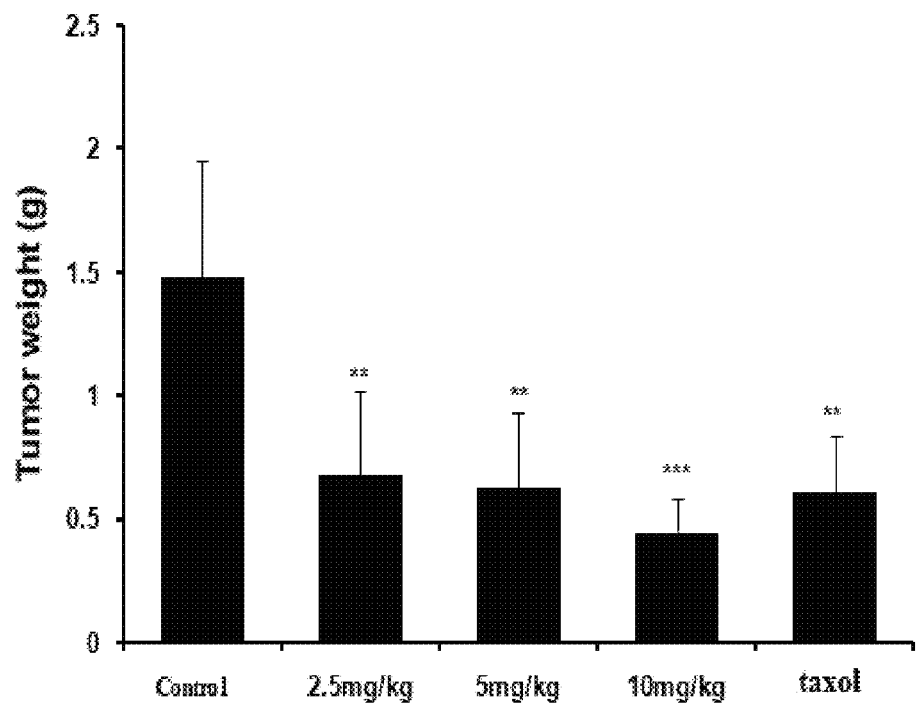

FIG. 12 presents the comparison of tumor weight of the HepG2 xenograft mice treated by the controls and variable doses of SKLBC-76.

Figure 13:
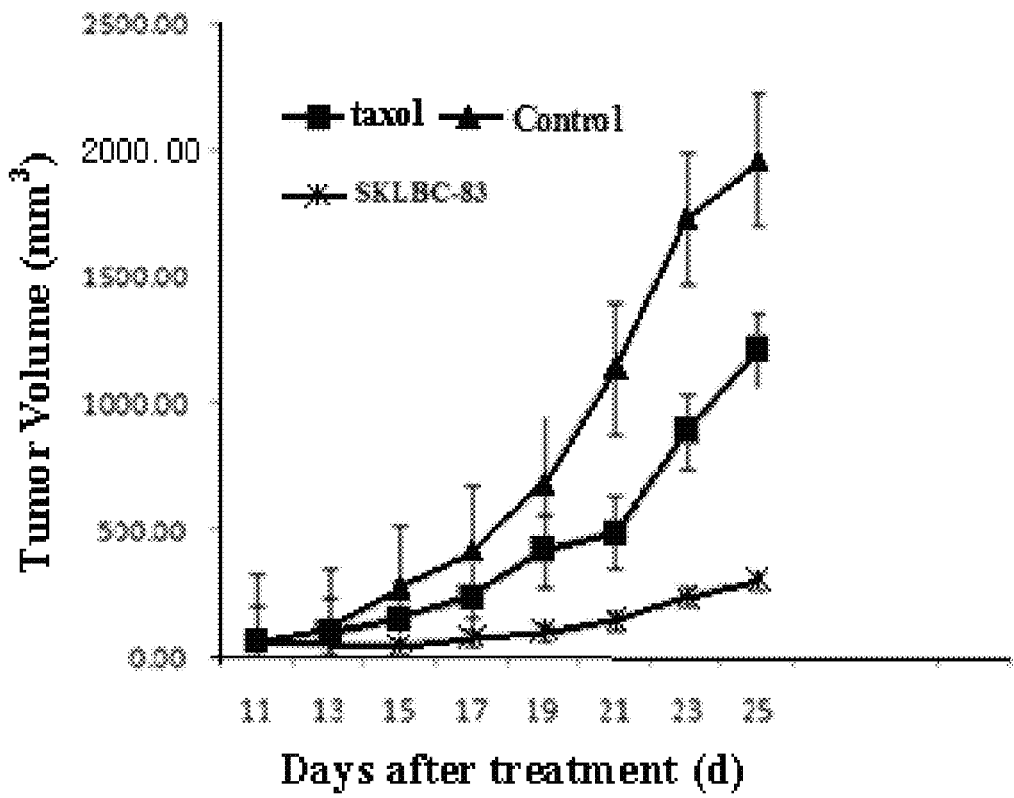

FIG. 13 presents the tumor volume time curve of the control and SKLBC-83 treatment groups in C26 tumor-bearing mice model.

Figure 14:
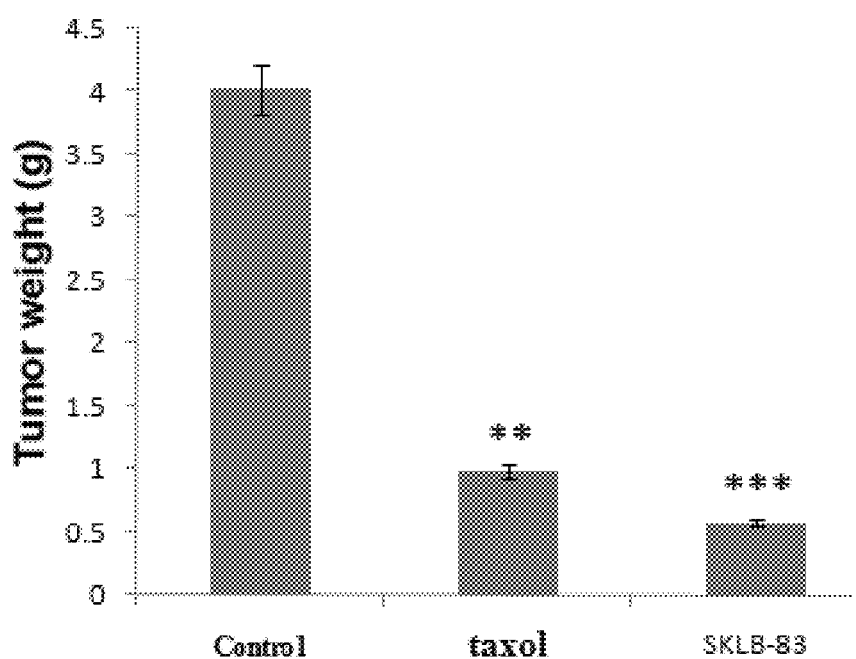

FIG. 14 presents the comparison of tumor weight of the C26 tumor-bearing mice treated by the controls and SKLBC-83.

Figure 15:
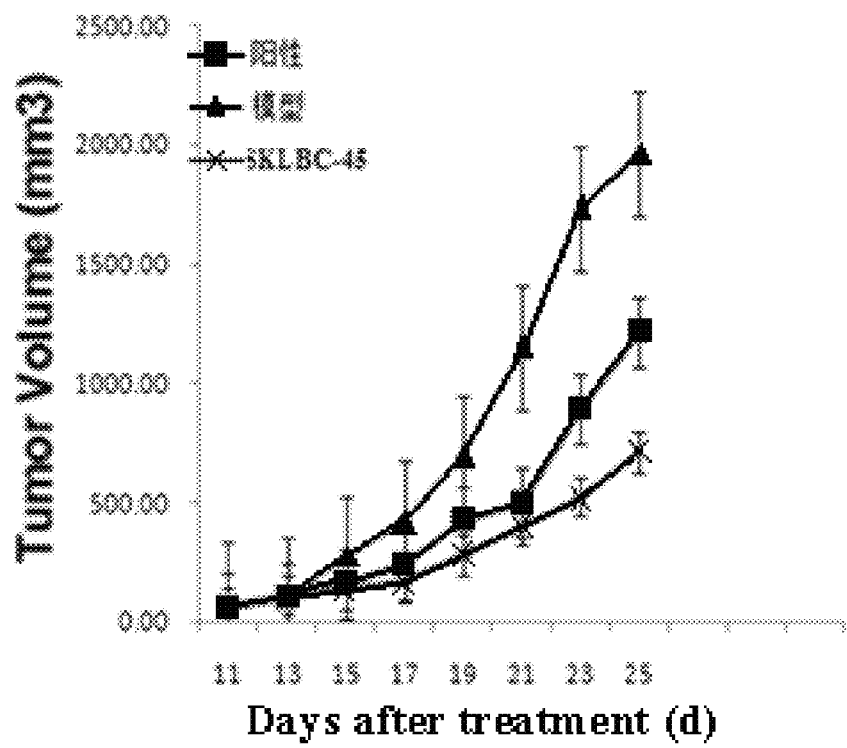

FIG. 15 presents the tumor volume time curve of the control and SKLBC-45 treatment groups in C26 tumor-bearing mice model.

Figure 16:
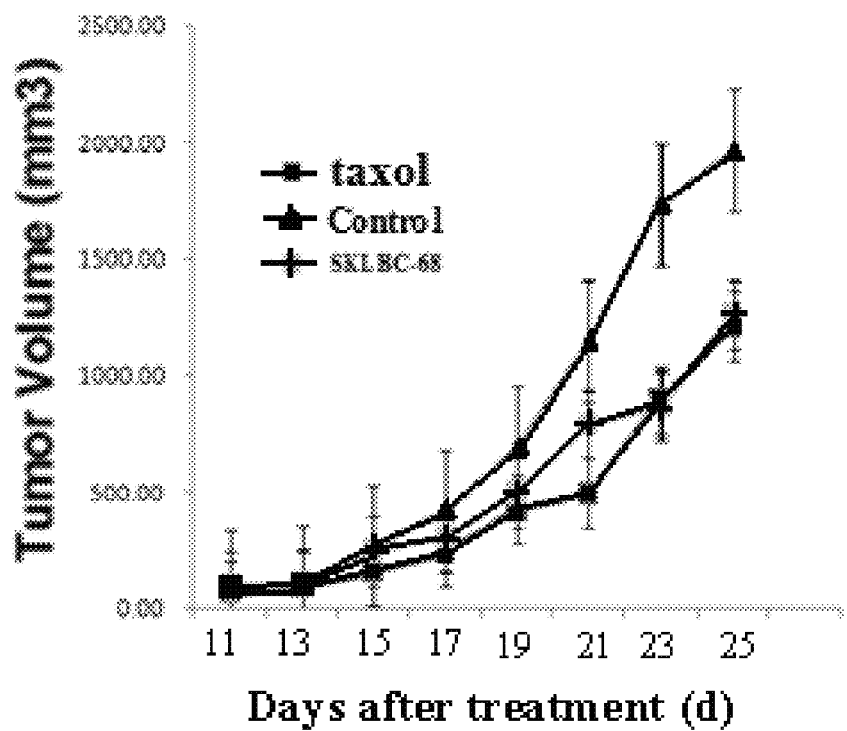

FIG. 16 presents the tumor volume time curve of the control and SKLBC-68 treatment groups in C26 tumor-bearing mice model.

Figure 17:
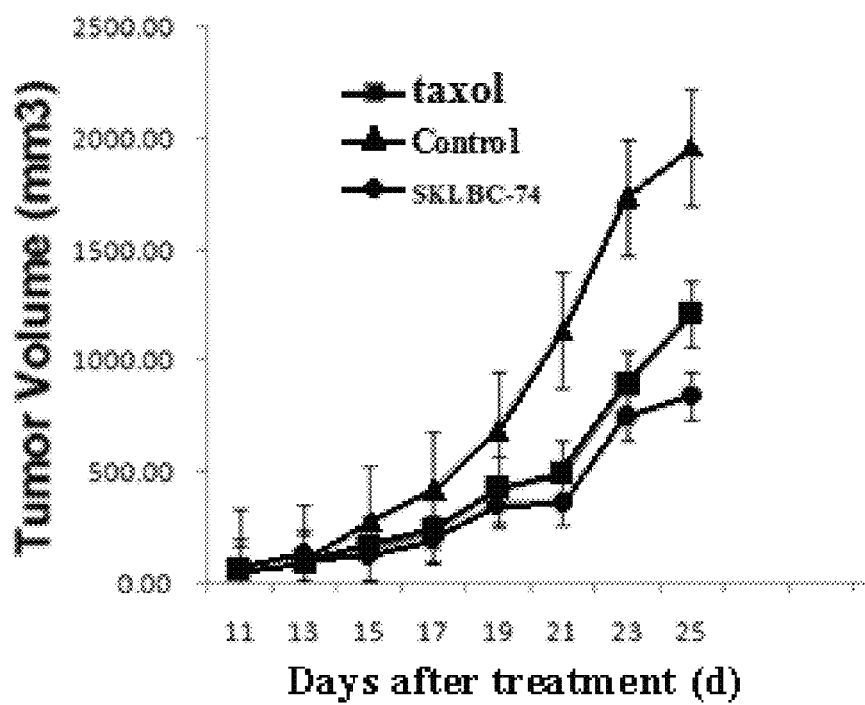

FIG. 17 presents the tumor volume time curve of the control and SKLBC-74 treatment groups in C26 tumor-bearing mice model.

Figure 18:
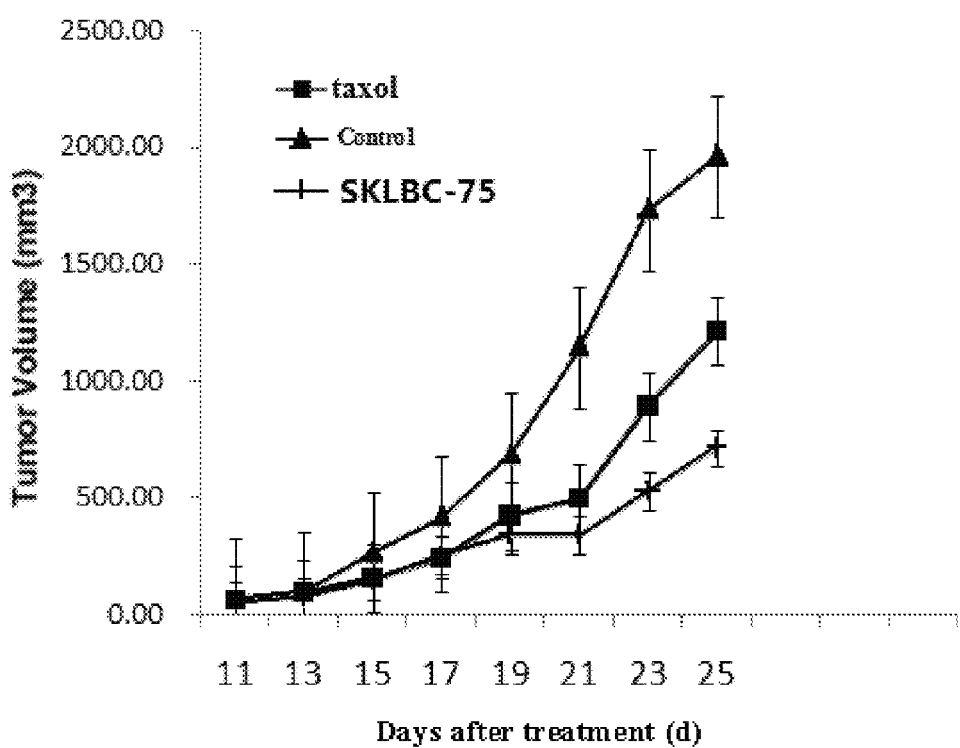

FIG. 18 presents the tumor volume time curve of the control and SKLBC-75 treatment groups in C26 tumor-bearing mice model.

Figure 19:
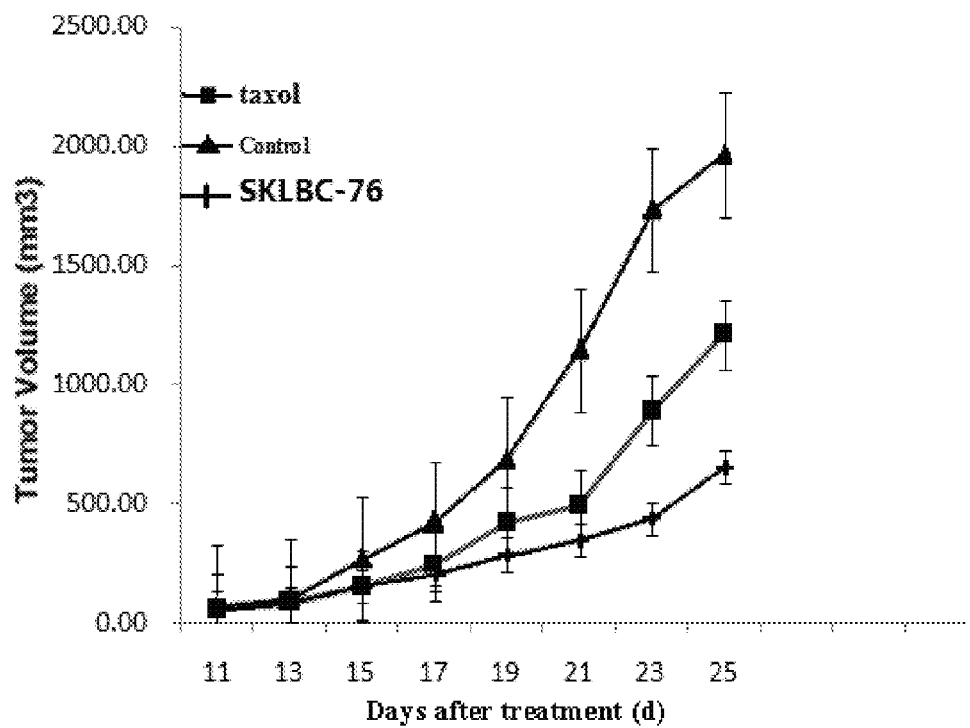

FIG. 19 presents the tumor volume time curve of the control and SKLBC-76 treatment groups in C26 tumor-bearing mice model.

Figure 20:
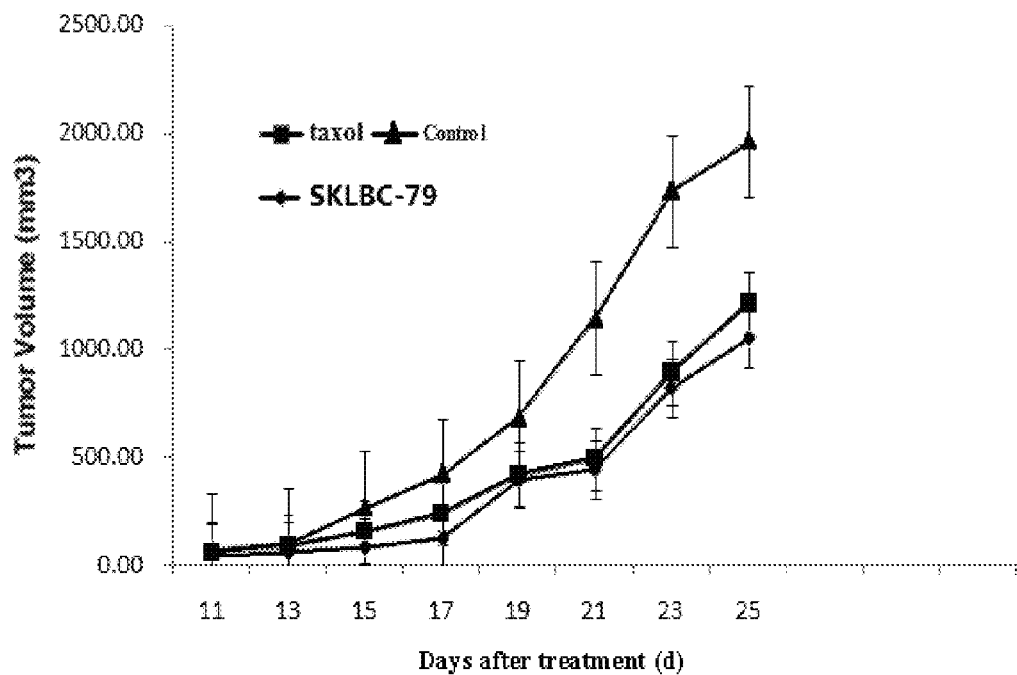

FIG. 20 presents the tumor volume time curve of the control and SKLBC-79 treatment groups in C26 tumor-bearing mice model.

Figure 21:
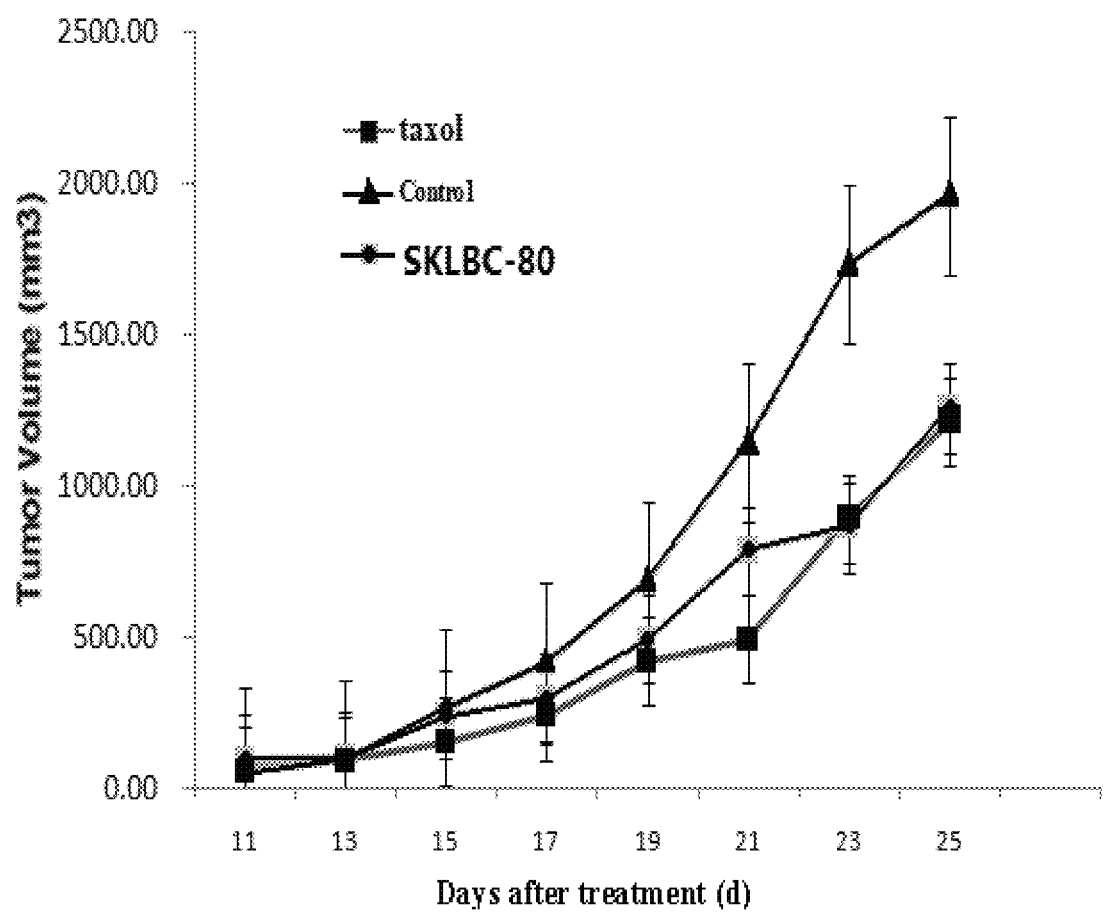

FIG. 21 presents the tumor volume time curve of the control and SKLBC-80 treatment groups in C26 tumor-bearing mice model.

The following examples are illustrative, but not limiting, of the method and composition of the present invention. Other suitable modifications and adaptations of the variety of conditions and parameters normally encountered in clinical therapy and which are obvious to those skilled in the art are within the spirit and scope of the invention.

EXAMPLE 1

The dried and finely ground seeds (10 kg) of *M. pachycarpa* Benth were extracted with ethanol (30 L×3) at room temperature. The solvent was evaporated under reduced pressure to yield a crude extract. Using water to suspend, the suspension was extracted by petro ether, ethyl acetate, then concentrated the solvent to give 150 g for petro ether part and 300 g for ethyl acetate part. The ethyl acetate part residue was used 300 g silicon gel (100-200) to mix the sample. The sample was put in BUCHI (490 mm×920 mm) and separated by ethyl acetate-petro ether (1:10, 1:5, 1:2, 1:1, 2:1, 4:1, V/V), the eluent was separated by per 500 mL as a part, detected by TLC, and combined the same parts. In the end, We got 10 parts, the Fr 7 was separated by Semi-Preparative HPLC Purification (MeOH:H$_2$O, 60:40, v/v), and got the compound Millepachine (20 mg).

The extractions were separated by chromatography, or Semi-Preparative HPLC Purification, or High-speed Countercurrent Chromatography (HSCCC).

$^1$H NMR (CDCl$_3$, 400 MHz) δ: 1.51 (s, 6H), 3.85 (s, 3H), 3.88 (s, 3H), 5.62 (d, J=10.0 Hz, 1H), 6.51 (d, J=8.8 Hz, 1H), 6.69 (d, J=10.0 Hz, 1H), 6.91 (d, J=8.8 Hz, 2H), 7.54 (d, J=8.8 Hz, 2H), 7.58 (d, J=15.6 Hz, 1H), 7.65 (d, J=15.6 Hz, 1H), 7.70 (d, J=8.8 Hz, 1H).

EXAMPLE 2

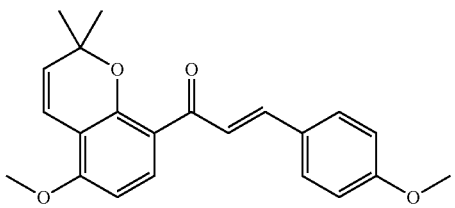

(E)-1-(5-methoxy-2,2-dimethyl-2H-chromen-8-yl)-
3-(4-methoxyphenyl)prop-2-en-1-one Compound 2 (464 mg, 2 mmol) and 4-methoxybenzaldehyde (272 mg, 2 mmol) were dissolved in 25 ml ethanol. Then 25 ml 10% KOH solution was added into the reaction by drop. The reaction was stirred at room temperature for 48 h. When the reaction was completed, 10% HCl was added to adjust the pH-7. Extracting the solution by ethyl estate, the organic layers were combined, dried by Na$_2$SO$_4$, concentrated under reduce pressure and purified by chromatography on silica gel to give the title compound (0.355 g, 51%).

EXAMPLE 3

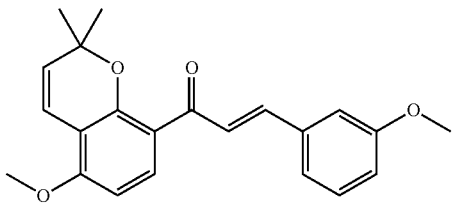

(E)-1-(5-methoxy-2,2-dimethyl-2H-chromen-8-yl)-
3-(3-methoxyphenyl)prop-2-en-1-one (SKLBC-2)

The title compound was prepared from 3-methoxybenzaldehyde by a procedure similar to example 2, and the yield was 0.4 g, 57%. $^1$H NMR (CDCl$_3$, 400 MHz) δ: 1.51 (s, 6H), 3.86 (s, 3H), 3.88 (s, 3H), 5.62 (d, J=10.0 Hz, 1H), 6.51 (d, J=8.8 Hz, 1H), 6.89 (d, J=10.0 Hz, 1H), 6.92 (dd, J=8.0 Hz, 2.0 Hz, 1H), 7.13 (s, 1H), 7.19 (d, J=8.0 Hz, 1H), 7.31 (t, J=8.0 Hz, 1H), 7.63 (d, J=15.6 Hz, 1H), 7.71 (d, J=15.6 Hz, 1H), 7.72 (d, J=8.0 Hz, 1H).

EXAMPLE 4

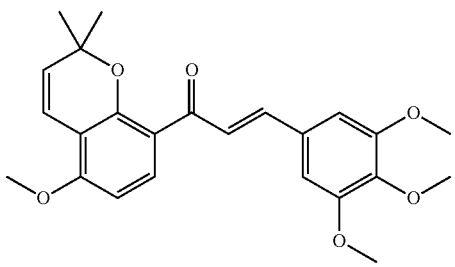

(E)-1-(5-methoxy-2,2-dimethyl-2H-chromen-8-yl)-
3-(3,4,5-trimethoxyphenyl)prop-2-en-1-one
(SKLBC-3)

The title compound was prepared from 3,4,5-trimethoxybenzaldehyde by a procedure similar to example 2, and the yield was 0.51 g, 62%. $^1$H NMR (CDCl$_3$, 400 MHz) δ: 1.52 (s, 6H), 3.90 (s, 12H), 5.63 (d, J=10.0 Hz, 1H), 6.52 (d, J=8.8 Hz, 1H), 6.70 (d, J=10.0 Hz, 1H,), 6.85 (s, 2H), 7.59 (d, J=15.6 Hz, 1H), 7.66 (d, J=15.6 Hz, 1H,), 7.73 (d, J=8.8 Hz, 1H).

EXAMPLE 5

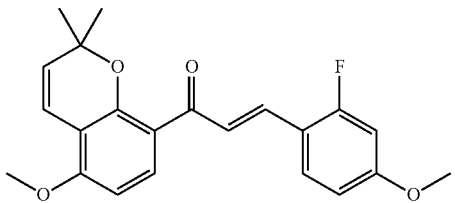

(E)-3-(2-fluoro-4-methoxyphenyl)-1-(5-methoxy-2,
2-dimethyl-2H-chromen-8-yl)prop-2-en-1-one
(SKLBC-4)

The title compound was prepared from 2-fluoro-4-methoxybenzaldehyde by a procedure similar to example 2, and the yield was 0.31 g, 42%. $^1$H NMR (CDCl$_3$, 400 MHz) δ: 1.51 (s, 6H), 3.84 (s, 3H), 3.89 (s, 3H), 5.62 (d, J=10.0 Hz, 1H), 6.51 (d, J=8.8 Hz, 1H), 6.64-6.70 (m, 2H), 6.72 (dd, J=8.8 Hz, 2.4 Hz, 1H), 7.50 (t, J=8.8 Hz, 1H), 7.71-7.75 (m, 2H), 7.77 (d, J=15.6 Hz, 1H).

EXAMPLE 6

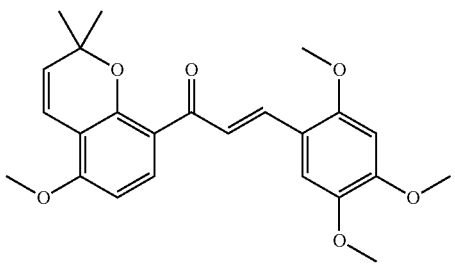

(E)-1-(5-methoxy-2,2-dimethyl-2H-chromen-8-yl)-3-(2,4,5-trimethoxyphenyl)prop-2-en-1-one (SKLBC-5)

The title compound was prepared from 2,4,5-trimethoxybenzaldehyde by a procedure similar to example 2, and the yield was 0.29 g, 42%. $^1$H NMR (CDCl$_3$, 400 MHz) δ: 1.50 (s, 6H), 3.89 (s, 9H), 3.94 (s, 3H), 5.61 (d, J=10.0 Hz, 1H), 6.50 (d, J=8.8 Hz, 1H), 6.69 (d, J=10.0 Hz, 1H), 7.14 (s, 1H), 7.59 (d, J=16.0 Hz, 1H), 7.69 (d, J=8.8 Hz, 1H), 8.03 (d, J=16.0 Hz, 1H).

EXAMPLE 7

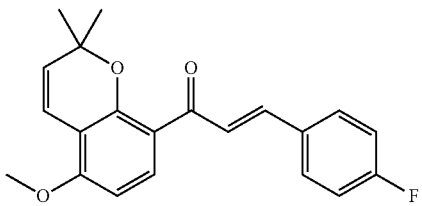 [SMILES: COc1ccc(C(=O)/C=C/c2ccc(F)cc2)c2c1C=CC(C)(C)O2]

(E)-3-(4-fluorophenyl)-1-(5-methoxy-2,2-dimethyl-2H-chromen-8-yl)prop-2-en-1-one (SKLBC-6)

The title compound was prepared from 4-fluorobenzaldehyde by a procedure similar to example 2, and the yield was 0.6 g, 89%. $^1$H NMR (CDCl$_3$, 400 MHz) δ: 1.50 (s, 6H), 3.89 (s, 3H), 5.63 (d, J=10.0 Hz, 1H), 6.51 (d, J=8.8 Hz, 1H), 6.69 (d, J=10.0 Hz, 1H), 7.09 (t, J=8.8 Hz, 2H), 7.56-7.60 (m, 2H), 7.61 (s, 2H), 7.71 (d, J=8.8 Hz, 1H).

EXAMPLE 8

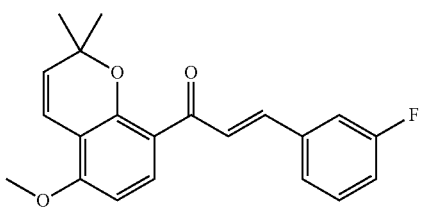 [SMILES: COc1ccc(C(=O)/C=C/c2cccc(F)c2)c2c1C=CC(C)(C)O2]

(E)-3-(3-fluorophenyl)-1-(5-methoxy-2,2-dimethyl-2H-chromen-8-yl)prop-2-en-1-one (SKLBC-7)

The title compound was prepared from 3-fluorobenzaldehyde by a procedure similar to example 2, and the yield was 0.5 g, 74%. $^1$H NMR (CDCl$_3$, 400 MHz) δ: 1.51 (s, 6H), 3.89 (s, 3H), 5.63 (d, J=10.0 Hz, 1H), 6.52 (d, J=8.8 Hz, 1H), 6.68 (d, J=10.0 Hz, 1H), 7.06-7.09 (m, 1H), 7.26-7.30 (m, 1H), 7.35-7.38 (m, 2H), 7.60 (d, J=16.0 Hz, 1H), 7.71 (d, 16.0 Hz, 1H), 7.72 (d, J=8.8 Hz, 1H).

EXAMPLE 9

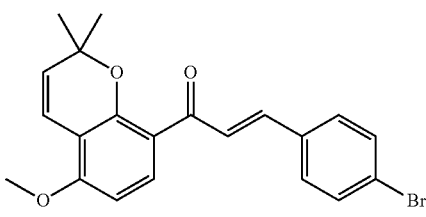 [SMILES: COc1ccc(C(=O)/C=C/c2ccc(Br)cc2)c2c1C=CC(C)(C)O2]

(E)-3-(4-bromophenyl)-1-(5-methoxy-2,2-dimethyl-2H-chromen-8-yl)prop-2-en-1-one (SKLBC-8)

The title compound was prepared from 4-bromobenzaldehyde by a procedure similar to example 2, and the yield was 0.6 g, 75%. $^1$H NMR (CDCl$_3$, 400 MHz) δ: 1.50 (s, 6H), 3.89 (s, 3H), 5.63 (d, J=10.0 Hz, 1H), 6.52 (d, J=8.8 Hz, 1H), 6.68 (d, J=10.0 Hz, 1H), 7.44 (d, J=8.8 Hz, 2H), 7.52 (d, J=8.8 Hz, 2H), 7.58 (d, J=16.0 Hz, 1H), 7.70-7.74 (m, 2H).

EXAMPLE 10

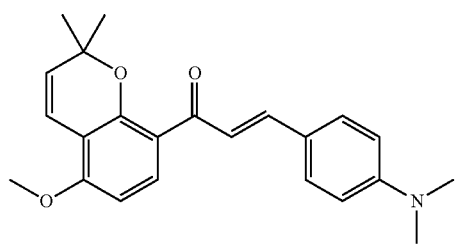

(E)-3-(4-(dimethylamino)phenyl)-1-(5-methoxy-2,2-dimethyl-2H-chromen-8-yl)prop-2-en-1-one (SKLBC-9)

The title compound was prepared from 4-(dimethylamino)benzaldehyde by a procedure similar to example 2, and the yield was 0.4 g, 55%. $^1$H NMR (CDCl$_3$, 400 MHz) δ: 1.51 (s, 6H), 3.03 (s, 6H), 3.89 (s, 3H), 5.62 (d, J=10.0 Hz, 1H), 6.50 (d, J=8.8 Hz, 1H), 6.68-6.71 (m, 3H), 7.50-7.55 (m, 3H), 7.66 (d, J=15.6 Hz, 1H), 7.68 (d, J=8.8 Hz, 1H).

EXAMPLE 11

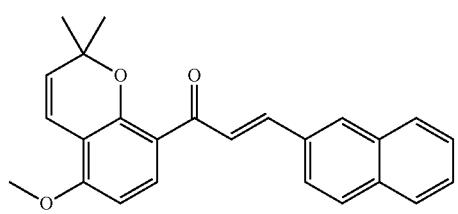 [SMILES: COc1ccc(C(=O)/C=C/c2ccc3ccccc3c2)c2c1C=CC(C)(C)O2]

(E)-1-(5-methoxy-2,2-dimethyl-2H-chromen-8-yl)-3-(naphthalen-2-yl)prop-2-en-1-one (SKLBC-10)

The title compound was prepared from 2-naphthaldehyde by a procedure similar to example 2, and the yield was 0.58 g, 78%. $^1$H NMR (CDCl$_3$, 400 MHz) δ: 1.54 (s, 6H), 3.90 (s, 3H), 5.64 (d, J=10.0 Hz, 1H), 6.53 (d, J=8.8 Hz, 1H), 6.70 (d, J=10.0 Hz, 1H), 7.50-7.52 (m, 2H), 7.75 (d, J=8.8 Hz, 2H), 7.83-7.88 (m, 5H), 8.00 (s, 1H).

EXAMPLE 12

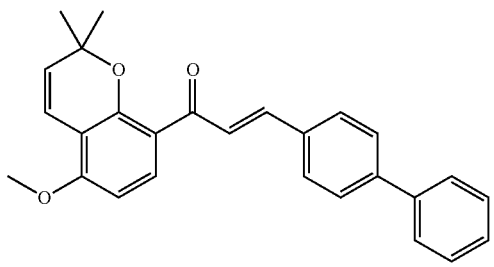 [SMILES: COc1ccc(C(=O)/C=C/c2ccc(-c3ccccc3)cc2)c2c1C=CC(C)(C)O2]

(E)-3-([1,1'-biphenyl]-4-yl)-1-(5-methoxy-2,2-dimethyl-2H-chromen-8-yl)prop-2-en-1-one (SKLBC-11)

The title compound was prepared from [1,1'-biphenyl]-4-carbaldehyde by a procedure similar to example 2, and the yield was 0.49 g, 62%. $^1$H NMR (CDCl$_3$, 400 MHz) δ: 1.53 (s, 6H), 3.90 (s, 3H), 5.64 (d, J=10.0 Hz, 1H), 6.53 (d, J=8.8 Hz, 1H), 6.70 (d, J=10.0 Hz, 1H), 7.38 (d, J=7.6 Hz, 1H), 7.47 (t, J=7.6 Hz, 2H), 7.63-7.80 (m, 9H).

EXAMPLE 13

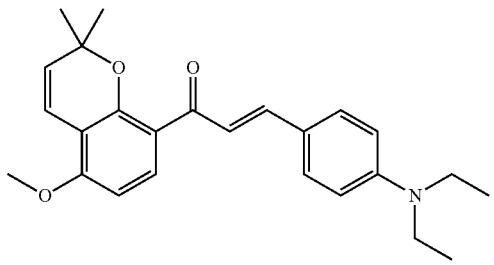 [SMILES: CCN(CC)c1ccc(/C=C/C(=O)c2ccc(OC)c3c2OC(C)(C)C=C3)cc1]

(E)-3-(4-(diethylamino)phenyl)-1-(5-methoxy-2,2-dimethyl-2H-chromen-8-yl)prop-2-en-1-one (SKLBC-12)

The title compound was prepared from 4-(diethylamino)benzaldehyde by a procedure similar to example 2, and the yield was 0.39 g, 49%. $^1$H NMR (CDCl$_3$, 400 MHz) δ: 1.20 (t, J=6.8 Hz, 6H), 1.51 (s, 6H), 3.40 (d, J=6.8 Hz, 4H), 3.88 (s, 3H), 5.62 (d, J=10.0 Hz, 1H), 6.50 (d, J=8.8 Hz, 1H), 6.65 (d, J=6.8 Hz, 2H), 6.68 (d, J=10.0 Hz, 1H), 7.48-7.52 (m, 3H), 7.65-7.70 (m, 2H).

EXAMPLE 14

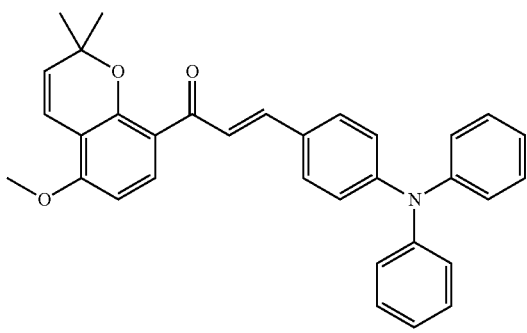 [SMILES: COc1ccc(C(=O)/C=C/c2ccc(N(c3ccccc3)c3ccccc3)cc2)c2c1C=CC(C)(C)O2]

(E)-3-(4-(diphenylamino)phenyl)-1-(5-methoxy-2,2-dimethyl-2H-chromen-8-yl)prop-2-en-1-one (SKLBC-13)

The title compound was prepared from 4-(diphenylamino)benzaldehyde by a procedure similar to example 2, and the yield was 0.77 g, 79%. $^1$H NMR (CDCl$_3$, 400 MHz) δ: 1.50 (s, 6H), 3.88 (s, 3H), 5.61 (d, J=10.0 Hz, 1H), 6.53 (d, J=8.8 Hz, 1H), 6.68 (d, J=10.0 Hz, 1H), 7.01 (d, J=8.8 Hz, 2H), 7.07-7.11 (m, 2H), 7.13-7.15 (m, 4H), 7.28-7.32 (m, 4H), 7.44 (d, J=8.8 Hz, 2H), 7.59 (d, J=15.2 Hz, 1H), 7.65 (d, J=15.2 Hz, 1H), 7.71 (d, J=8.8 Hz, 1H).

EXAMPLE 15

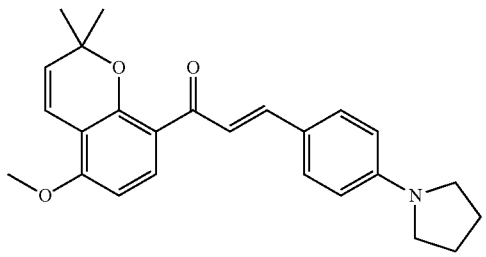 [SMILES: COc1ccc(C(=O)/C=C/c2ccc(N3CCCC3)cc2)c2c1C=CC(C)(C)O2]

(E)-1-(5-methoxy-2,2-dimethyl-2H-chromen-8-yl)-3-(4-(pyrrolidin-1-yl)phenyl)prop-2-en-1-one (SKLBC-14)

The title compound was prepared from 4-(pyrrolidin-1-yl)benzaldehyde by a procedure similar to example 2, and the yield was 0.36 g, 46%. $^1$H NMR (CDCl$_3$, 400 MHz) δ: 1.51 (s, 6H), 2.18 (s, 2H), 3.40 (s, 2H), 3.88 (s, 3H), 5.62 (d, J=10.0 Hz, 1H), 6.50 (d, J=8.8 Hz, 1H), 6.68-6.71 (m, 3H), 7.51-7.55 (m, 3H), 7.65-7.71 (m, 2H).

EXAMPLE 16

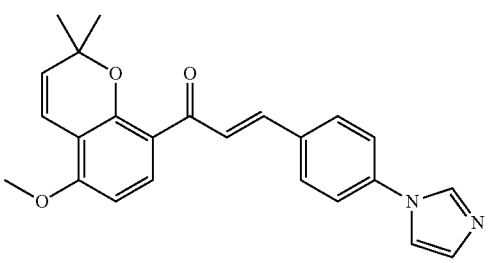 [SMILES: COc1ccc(C(=O)/C=C/c2ccc(-n3ccnc3)cc2)c2c1C=CC(C)(C)O2]

(E)-3-(4-(1H-imidazol-1-yl)phenyl)-1-(5-methoxy-2,2-dimethyl-2H-chromen-8-yl)prop-2-en-1-one (SKLBC-15)

The title compound was prepared from 4-(1H-imidazol-1-yl)benzaldehyde by a procedure similar to example 2, and the yield was 0.51 g, 66%. $^1$H NMR (CDCl$_3$, 400 MHz) δ: 1.51 (s, 6H), 3.90 (s, 3H), 5.64 (d, J=10.0 Hz, 1H), 6.53 (d, J=8.8 Hz, 1H), 6.69 (d, J=10.0 Hz, 1H), 7.46-7.50 (m, 2H), 7.59 (d, J=8.0 Hz, 2H), 7.65 (d, J=16.0 Hz, 1H), 7.34-7.81 (m, 4H), 9.07 (s, 1H).

EXAMPLE 17

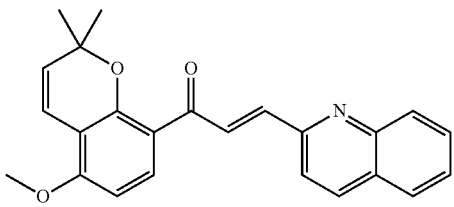 [SMILES: COc1ccc(C(=O)/C=C/c2ccc3ccccc3n2)c2c1C=CC(C)(C)O2]

(E)-1-(5-methoxy-2,2-dimethyl-2H-chromen-8-yl)-
3-(quinolin-2-yl)prop-2-en-1-one (SKLBC-16)

The title compound was prepared from quinoline-2-carbaldehyde by a procedure similar to example 2, and the yield was 0.49 g, 66%. ¹H NMR (CDCl₃, 400 MHz) δ: 1.57 (s, 6H), 3.90 (s, 3H), 5.64 (d, J=10.0 Hz, 1H), 6.53 (d, J=8.8 Hz, 1H), 6.69 (d, J=10.0 Hz, 1H), 7.56 (t, J=7.6 Hz, 1H), 7.66 (d, J=8.8 Hz, 1H), 7.73-7.86 (m, 4H), 8.14 (s, 1H), 8.20 (d, J=8.0 Hz, 1H), 8.33 (d, J=15.6 Hz, 1H).

EXAMPLE 18

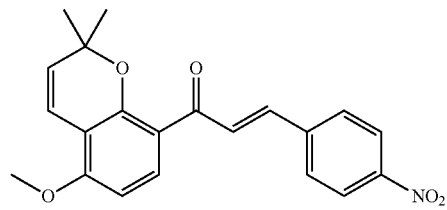 [SMILES: COc1ccc(C(=O)/C=C/c2ccc([N+](=O)[O-])cc2)c2c1C=CC(C)(C)O2]

(E)-1-(5-methoxy-2,2-dimethyl-2H-chromen-8-yl)-
3-(4-nitrophenyl)prop-2-en-1-one (SKLBC-17)

The title compound was prepared from 4-nitrobenzaldehyde by a procedure similar to example 2, and the yield was 0.41 g, 56%. ¹H-NMR (CDCl₃, 400 MHz) δ: 1.51 (s, 6H), 3.91 (s, 3H), 5.64 (d, J=10.0 Hz, 1H), 6.54 (d, J=8.8 Hz, 1H), 6.69 (d, J=10.0 Hz, 1H), 7.65 (d, J=15.6 Hz, 1H), 7.72 (d, J=8.8 Hz, 2H), 7.75 (d, J=8.8 Hz, 1H), 7.83 (d, J=15.6 Hz, 1H), 8.26 (d, J=8.8 Hz, 2H).

EXAMPLE 19

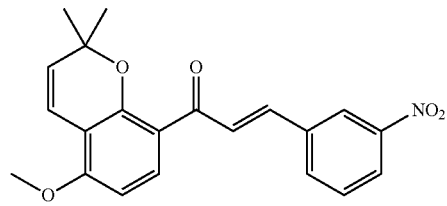 [SMILES: COc1ccc(C(=O)/C=C/c2cccc([N+](=O)[O-])c2)c2c1C=CC(C)(C)O2]

(E)-1-(5-methoxy-2,2-dimethyl-2H-chromen-8-yl)-
3-(3-nitrophenyl)prop-2-en-1-one (SKLBC-18)

The title compound was prepared from 3-nitrobenzaldehyde by a procedure similar to example 2, and the yield was 0.47 g, 64%. ¹H NMR (CDCl₃, 400 MHz) δ: 1.55 (s, 6H), 3.91 (s, 3H), 5.65 (d, J=10.0 Hz, 1H), 6.54 (d, J=8.8 Hz, 1H), 6.70 (d, J=10.0 Hz, 1H), 7.59 (t, J=8.0 Hz, 1H), 7.68 (d, J=15.6 Hz, 1H), 7.77 (d, J=8.8 Hz, 1H), 7.84 (d, J=8.0 Hz, 1H), 7.90 (d, J=15.6 Hz, 1H), 8.21 (dd, J=8.0 Hz, 1.2 Hz, 1H), 8.52 (s, 1H).

EXAMPLE 20

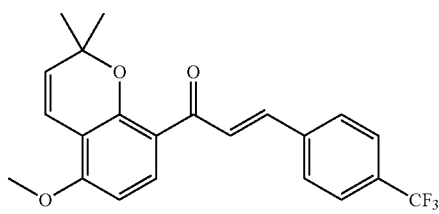 [SMILES: COc1ccc(C(=O)/C=C/c2ccc(C(F)(F)F)cc2)c2c1C=CC(C)(C)O2]

(E)-1-(5-methoxy-2,2-dimethyl-2H-chromen-8-yl)-
3-(4-(trifluoromethyl)phenyl)prop-2-en-1-one
(SKLBC-19)

The title compound was prepared from 4-(trifluoromethyl)benzaldehyde by a procedure similar to example 2, and the yield was 0.59 g, 76%. ¹H NMR (CDCl₃, 400 MHz) δ: 1.51 (s, 6H), 3.90 (s, 3H), 5.64 (d, J=10.0 Hz, 1H), 6.53 (d, J=8.8 Hz, 1H), 6.69 (d, J=10.0 Hz, 1H), 7.65-7.71 (m, 5H), 7.74 (d, J=8.8 Hz, 1H), 7.78 (d, J=15.6 Hz, 1H).

EXAMPLE 21

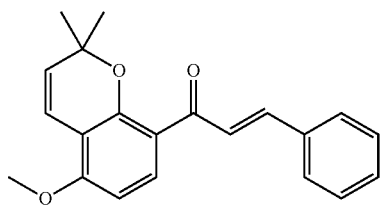 [SMILES: COc1ccc(C(=O)/C=C/c2ccccc2)c2c1C=CC(C)(C)O2]

(E)-1-(5-methoxy-2,2-dimethyl-2H-chromen-8-yl)-
3-phenylprop-2-en-1-one (SKLBC-20)

The title compound was prepared from benzaldehyde by a procedure similar to example 2, and the yield was 0.35 g, 55%. ¹H NMR (CDCl₃, 400 MHz) δ: 1.51 (s, 6H), 3.89 (s, 3H), 5.63 (d, J=10.0 Hz, 1H), 6.52 (d, J=8.8 Hz, 1H), 6.69 (d, J=10.0 Hz, 1H), 7.37-7.42 (m, 3H), 7.60-7.67 (m, 2H), 7.71-7.76 (m, 3H).

EXAMPLE 22

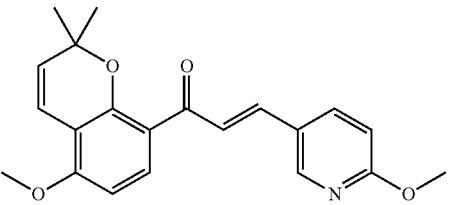

(E)-1-(5-methoxy-2,2-dimethyl-2H-chromen-8-yl)-
3-(6-methoxypyridin-3-yl)prop-2-en-1-one
(SKLBC-21)

The title compound was prepared from 6-methoxynicotinaldehyde by a procedure similar to example 2, and the yield was 0.51 g, 72%. ¹H NMR (CDCl₃, 400 MHz) δ: 1.50 (s, 6H), 3.89 (s, 3H), 3.98 (s, 3H), 5.63 (d, J=10.0 Hz, 1H), 6.52 (d, J=8.8 Hz, 1H), 6.69 (d, J=10.0 Hz, 1H), 6.78 (d, J=8.8 Hz, 1H), 7.64 (s, 2H), 7.71 (d, J=8.8 Hz, 1H), 7.81-7.84 (m, 1H), 8.37 (s, 1H).

EXAMPLE 23

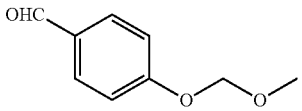

4-(methoxymethoxy)benzaldehyde (SKLBC-22a)

4-hydroxybenzaldehyde (1.22 g, 10 mmol) was dissolved in 100 ml dried DMF and stirred at room temperature. NaH (0.8 g) was added in to the reaction. After 10 min, MOMCl (1.5 ml) was added into the reaction by drop. Then the result solution was stirred at room temperature, and monitored by TLC. When the reaction was completed, 500 ml H₂O was added. The resulting solution was extracted by ethyl acetate, and the organic layers were combined, dried by Na₂SO₄, concentrated by reduce pressure. The resulting oil was directly used in the next step without further purification. ¹H NMR (CDCl₃, 400 MHz) δ: 3.50 (s, 3H), 5.26 (s, 2H), 7.14 (d, J=8.8 Hz, 2H), 7.83 (d, J=8.8 Hz, 2H), 9.90 (s, 1H).

EXAMPLE 24

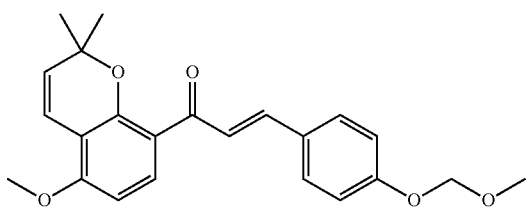

(E)-1-(5-methoxy-2,2-dimethyl-2H-chromen-8-yl)-
3-(4-(methoxymethoxy)phenyl)prop-2-en-1-one
(SKLBC-22b)

The title compound was prepared from SKLBC-22a by a procedure similar to example 2, and the yield was 0.49 g, 64%. ¹H NMR (CDCl₃, 400 MHz) δ: 1.51 (s, 6H), 3.49 (s, 3H), 3.88 (s, 3H), 5.21 (s, 2H), 5.62 (d, J=10.0 Hz, 1H), 6.51 (d, J=8.8 Hz, 1H), 6.69 (d, J=10.0 Hz, 1H), 7.05 (d, J=8.4 Hz, 2H), 7.54 (d, J=8.4 Hz, 2H), 7.60 (d, J=15.6 Hz, 1H), 7.65 (d, J=15.6 Hz, 1H), 7.70 (d, J=8.8 Hz, 1H).

EXAMPLE 25

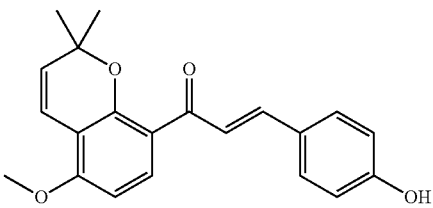 [SMILES: COc1ccc(C(=O)/C=C/c2ccc(O)cc2)c2c1C=CC(C)(C)O2]

(E)-3-(4-hydroxyphenyl)-1-(5-methoxy-2,2-dimethyl-2H-chromen-8-yl)prop-2-en-1-one (SKLBC-22)

SKLBC-22b (100 mg) was dissolved in 3 ml methanol, then 2 ml 10% HCl was added. The result solution was refluxed for 1 h, then cooled to room temperature and filtered. The solid was purified by chromatography on silica gel to give the title compound 84 mg, 95%. ¹H NMR (CDCl₃, 400 MHz) δ: 1.50 (s, 6H), 3.89 (s, 3H), 5.52 (s, 1H), 5.63 (d, J=10.0 Hz, 1H), 6.51 (d, J=8.8 Hz, 1H), 6.69 (d, J=10.0 Hz, 1H), 6.86 (d, J=8.4 Hz, 2H), 7.49 (d, J=8.4 Hz, 2H), 7.57 (d, J=15.6 Hz, 1H), 7.65 (d, J=15.6 Hz, 1H), 7.70 (d, J=8.8 Hz, 1H).

EXAMPLE 26

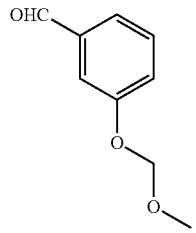

3-(methoxymethoxy)benzaldehyde (SKLBC-23a)

The title compound was prepared from 3-hydroxybenzaldehyde by a procedure similar to example 23. ¹H NMR (CDCl₃, 400 MHz) δ: 3.47 (s, 3H), 5.21 (s, 2H), 7.26-7.29 (m, 1H), 7.43 (t, J=8.0 Hz, 1H), 7.49-7.52 (m, 2H), 9.95 (s, 1H).

EXAMPLE 27

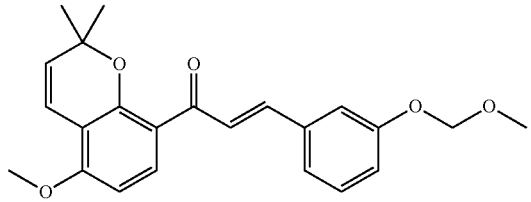

(E)-1-(5-methoxy-2,2-dimethyl-2H-chromen-8-yl)-
3-(3-(methoxymethoxy)phenyl)prop-2-en-1-one
(SKLBC-23b)

The title compound was prepared from SKLBC-23a by a procedure similar to example 2, and the yield was 0.55 g, 72%. ¹H NMR (CDCl₃, 400 MHz) δ: 1.52 (s, 6H), 3.49 (s, 3H), 3.89 (s, 3H), 5.20 (s, 2H), 5.63 (d, J=10.0 Hz, 1H), 6.51 (d, J=8.8 Hz, 1H), 6.68 (d, J=10.0 Hz, 1H), 7.23 (d, J=8.0 Hz, 1H), 7.29 (d, J=8.0 Hz, 1H), 7.33-7.33 (m, 1H), 7.63 (d, J=15.6 Hz, 1H), 7.71 (d, J=15.6 Hz, 1H), 7.72 (d, J=8.8 Hz, 1H).

EXAMPLE 28

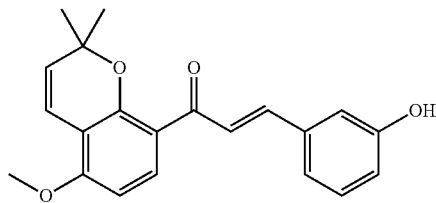 [SMILES: COc1ccc(C(=O)/C=C/c2cccc(O)c2)c2c1C=CC(C)(C)O2]

(E)-3-(3-hydroxyphenyl)-1-(5-methoxy-2,2-dimethyl-2H-chromen-8-yl)prop-2-en-1-one (SKLBC-23)

The title compound was prepared from SKLBC-23b by a procedure similar to example 25, and the yield was 75 g, 85%. ¹H NMR (CDCl₃, 400 MHz) δ: 1.51 (s, 6H), 3.89 (s, 3H), 5.21 (s, 1H), 5.63 (d, J=10.0 Hz, 1H), 6.52 (d, J=8.8 Hz, 1H), 6.68 (d, J=10.0 Hz, 1H), 6.86 (dd, J=8.0 Hz, 1.6 Hz, 1H), 7.10 (s, 1H), 7.19 (d, J=8.0 Hz, 1H), 7.28 (d, J=8.0 Hz, 1H), 7.62 (d, J=15.6 Hz, 1H), 7.69 (d, J=15.6 Hz, 1H), 7.72 (d, J=8.8 Hz, 1H).

EXAMPLE 29

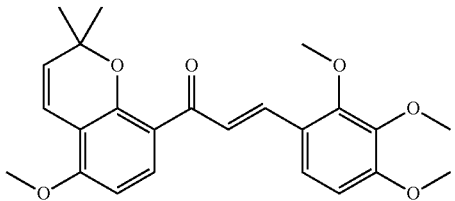

(E)-1-(5-methoxy-2,2-dimethyl-2H-chromen-8-yl)-3-(2,3,4-trimethoxyphenyl)prop-2-en-1-one (SKLBC-24)

The title compound was prepared from 2,3,4-trimethoxybenzaldehyde by a procedure similar to example 2, and the yield was 0.61 g, 74%. ¹H NMR (CDCl₃, 400 MHz) δ: 1.50 (s, 6H), 3.88 (s, 3H), 3.89 (s, 3H), 3.92 (s, 3H), 3.94 (s, 3H), 5.62 (d, J=10.0 Hz, 1H), 6.51 (d, J=8.8 Hz, 1H), 6.68 (d, J=10.0 Hz, 1H), 6.70 (d, J=8.4 Hz, 1H), 7.36 (d, J=8.8 Hz, 1H), 7.66 (d, J=15.6 Hz, 1H), 7.70 (d, J=8.4 Hz, 1H), 7.91 (d, J=15.6 Hz, 1H).

EXAMPLE 30

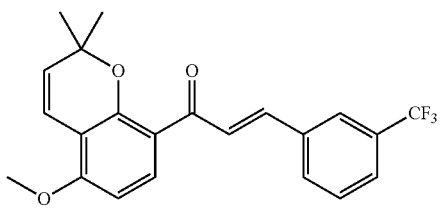 [SMILES: COc1ccc(C(=O)/C=C/c2cccc(C(F)(F)F)c2)c2c1C=CC(C)(C)O2]

(E)-1-(5-methoxy-2,2-dimethyl-2H-chromen-8-yl)-3-(3-(trifluoromethyl)phenyl)prop-2-en-1-one (SKLBC-25)

The title compound was prepared from 3-(trifluoromethyl)benzaldehyde by a procedure similar to example 2, and the yield was 0.47 g, 61%. ¹H NMR (CDCl₃, 400 MHz) δ: 1.52 (s, 6H), 3.90 (s, 3H), 5.64 (d, J=10.0 Hz, 1H), 6.53 (d, J=8.8 Hz, 1H), 6.69 (d, J=10.0 Hz, 1H), 7.53 (t, J=7.6 Hz, 1H), 7.61 (d, J=7.6 Hz, 1H), 7.66 (d, J=15.6 Hz, 1H), 7.72 (d, J=7.6 Hz, 1H), 7.76 (d, J=8.8 Hz, 1H), 7.82 (d, J=15.6 Hz, 1H), 7.89 (s, 1H).

EXAMPLE 31

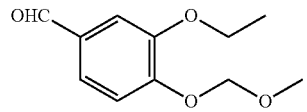

3-ethoxy-4-(methoxymethoxy)benzaldehyde (SKLBC-16a)

The title compound was prepared from 4-ethoxy-3-hydroxybenzaldehyde by a procedure similar to example 23. ¹H NMR (CDCl₃, 400 MHz) δ: 1.46 (t, J=6.8 Hz, 3H), 3.51 (s, 3H), 4.15 (q, J=6.8 Hz, 13.6 Hz, 2H), 5.29 (s, 2H), 7.23 (d, J=8.0 Hz, 1H), 7.39-7.41 (m, 2H), 9.84 (s, 1H).

EXAMPLE 32

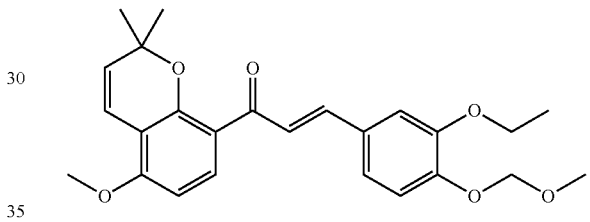

(E)-3-(4-ethoxy-3-(methoxymethoxy)phenyl)-1-(5-methoxy-2,2-dimethyl-2H-chromen-8-yl)prop-2-en-1-one (SKLBC-26b)

The title compound was prepared from SKLBC-26a by a procedure similar to example 2, and the yield was 0.67 g, 79%. ¹H NMR (CDCl₃, 400 MHz) δ: 1.48 (t, J=7.6 Hz, 3H), 1.51 (s, 6H), 3.53 (s, 3H), 3.89 (s, 3H), 4.14 (q, J=7.6 Hz, 14.0 Hz, 2H), 5.26 (s, 2H), 5.63 (d, J=10.0 Hz, 1H), 6.51 (d, J=8.8 Hz, 1H), 6.69 (d, J=10.0 Hz, 1H), 7.16 (s, 1H), 7.63-7.63 (m, 2H), 7.71 (d, J=8.8 Hz, 1H).

EXAMPLE 33

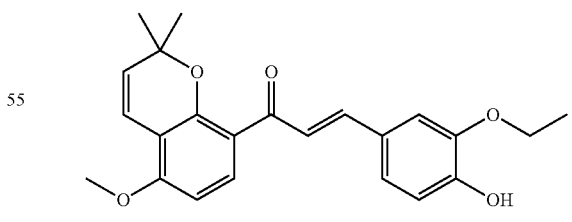

(E)-3-(3-ethoxy-4-hydroxyphenyl)-1-(5-methoxy-2,2-dimethyl-2H-chromen-8-yl)prop-2-en-1-one (SKLBC-26)

The title compound was prepared from SKLBC-26b by a procedure similar to example 25, and the yield was 88%.

¹H-NMR (CDCl₃, 400 MHz) δ: 1.46-1.50 (m, 9H), 3.89 (s, 3H), 4.15 (q, J=7.6 Hz, 13.6 Hz, 2H), 5.62 (d, J=10.0 Hz, 1H), 5.89 (s, 1H), 6.51 (d, J=8.8 Hz, 1H), 6.69 (d, J=10.0 Hz, 1H), 6.93 (d, J=8.4 Hz, 1H), 7.10 (s, 1H), 7.14 (d, J=8.4 Hz, 1H), 7.55 (d, J=15.6 Hz, 1H), 7.61 (d, J=15.6 Hz, 1H), 7.70 (d, J=8.8 Hz, 1H).

EXAMPLE 34

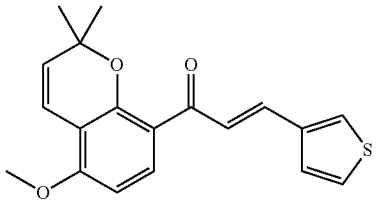 [SMILES: COc1ccc(C(=O)/C=C/c2ccsc2)c2c1C=CC(C)(C)O2]

(E)-1-(5-methoxy-2,2-dimethyl-2H-chromen-8-yl)-3-(thiophen-3-yl)prop-2-en-1-one (SKLBC-27)

The title compound was prepared from thiophene-3-carbaldehyde by a procedure similar to example 2, and the yield was 0.31 g, 48%. ¹H NMR (CDCl₃, 400 MHz) δ: 1.51 (s, 6H), 3.89 (s, 3H), 5.62 (d, J=10.0 Hz, 1H), 6.51 (d, J=8.8 Hz, 1H), 6.68 (d, J=10.0 Hz, 1H), 7.35-7.36 (m, 2H), 7.53 (s, 1H), 7.54 (d, J=15.6 Hz, 1H), 7.67 (d, J=15.6 Hz, 1H), 7.71 (d, J=8.8 Hz, 1H).

EXAMPLE 35

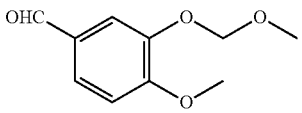

4-methoxy-3-(methoxymethoxy)benzaldehyde (SKLBC-28a)

The title compound was prepared from 3-hydroxy-4-methoxybenzaldehyde by a procedure similar to example 23. ¹H NMR (CDCl₃, 400 MHz) δ: 3.50 (s, 3H), 3.93 (s, 3H), 5.25 (s, 2H), 6.97 (d, J=8.0 Hz, 1H), 7.50 (dd, J=8.0 Hz, 2.0 Hz, 1H), 7.63 (d, J=2.0 Hz, 1H), 9.81 (s, 1H).

EXAMPLE 36

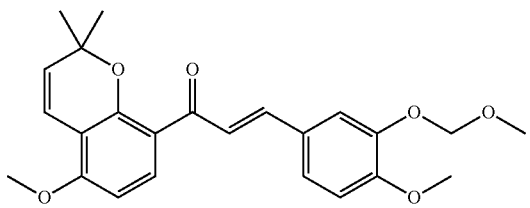

(E)-1-(5-methoxy-2,2-dimethyl-2H-chromen-8-yl)-3-(4-methoxy-3-(methoxymethoxy)phenyl)prop-2-en-1-one (SKLBC-28b)

The title compound was prepared from SKLBC-28a by a procedure similar to example 2, and the yield was 0.36 g, 44%. ¹H NMR (CDCl₃, 400 MHz) δ: 1.52 (s, 6H), 3.52 (s, 3H), 3.88 (s, 3H), 3.92 (s, 3H), 5.26 (s, 2H), 5.62 (d, J=10.0 Hz, 1H), 6.51 (d, J=8.8 Hz, 1H), 6.68 (d, J=10.0 Hz, 1H), 6.90 (d, J=8.0 Hz, 1H), 7.20 (dd, J=8.0 Hz, 2.0 Hz, 1H), 7.52 (d, J=2.0 Hz, 1H), 7.60 (d, J=15.6 Hz, 1H), 7.64 (d, J=15.6 Hz, 1H), 7.71 (d, J=8.8 Hz, 1H).

EXAMPLE 37

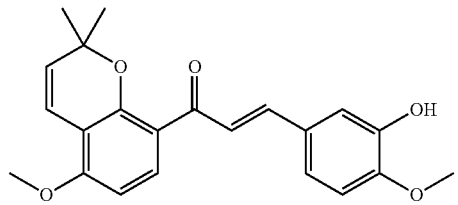

(E)-3-(3-hydroxy-4-methoxyphenyl)-1-(5-methoxy-2,2-dimethyl-2H-chromen-8-yl)prop-2-en-1-one (SKLBC-28)

The title compound was prepared from SKLBC-28b by a procedure similar to example 25, and the yield was 59%. ¹H NMR (CDCl₃, 400 MHz) δ: 1.51 (s, 6H), 3.89 (s, 3H), 3.94 (s, 3H), 5.62 (d, J=10.0 Hz, 1H), 5.64 (s, 1H), 6.51 (d, J=8.8 Hz, 1H), 6.68 (d, J=10.0 Hz, 1H), 6.86 (d, J=8.4 Hz, 1H), 7.09 (dd, J=8.4 Hz, 2.0 Hz, 1H), 7.21 (d, J=8.4 Hz, 1H), 7.56 (d, J=15.6 Hz, 1H), 7.60 (d, J=15.6 Hz, 1H), 7.70 (d, J=8.8 Hz, 1H).

EXAMPLE 38

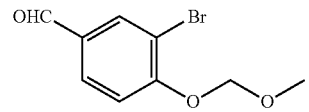

3-bromo-4-(methoxymethoxy)benzaldehyde (SKLBC-29a)

The title compound was prepared from 3-bromo-4-hydroxybenzaldehyde by a procedure similar to example 23. ¹H NMR (CDCl₃, 400 MHz) δ: 3.50 (s, 3H), 5.32 (s, 2H), 7.23-7.27 (m, 1H), 7.75-7.78 (m, 1H), 8.05-8.07 (m, 1H), 9.84 (s, 1H).

EXAMPLE 39

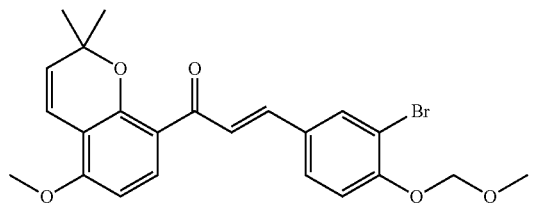

(E)-3-(3-bromo-4-(methoxymethoxy)phenyl)-1-(5-methoxy-2,2-dimethyl-2H-chromen-8-yl)prop-2-en-1-one (SKLBC-29b)

The title compound was prepared from SKLBC-29a by a procedure similar to example 2, and the yield was 0.51 g, 56%. $^1$H NMR (CDCl$_3$, 400 MHz) δ: 1.51 (s, 6H), 3.53 (s, 3H), 3.89 (s, 3H), 5.29 (s, 2H), 5.63 (d, J=10.0 Hz, 1H), 6.51 (d, J=8.8 Hz, 1H), 6.68 (d, J=10.0 Hz, 1H), 7.16 (d, J=8.8 Hz, 1H), 7.46 (dd, J=8.8 Hz, 2.0 Hz, 1H), 7.55 (d, J=15.6 Hz, 1H), 7.63 (d, J=15.6 Hz, 1H), 7.71 (d, J=8.8 Hz, 1H), 7.82 (d, J=2.0 Hz, 1H).

EXAMPLE 40

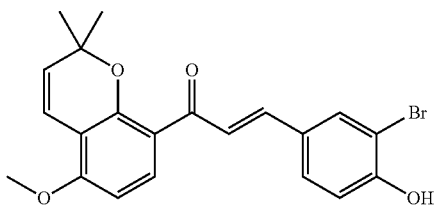 [SMILES: COc1ccc(C(=O)/C=C/c2ccc(O)c(Br)c2)c2c1C=CC(C)(C)O2]

(E)-3-(3-bromo-4-hydroxyphenyl)-1-(5-methoxy-2,2-dimethyl-2H-chromen-8-yl)prop-2-en-1-one (SKLBC-29)

The title compound was prepared from SKLBC-29b by a procedure similar to example 25, and the yield was 91%. $^1$H NMR (CDCl$_3$, 400 MHz) δ: 1.51 (s, 6H), 3.89 (s, 3H), 5.63 (d, J=10.0 Hz, 1H), 5.77 (s, 1H), 6.51 (d, J=8.8 Hz, 1H), 6.68 (d, J=10.0 Hz, 1H), 7.03 (d, J=8.4 Hz, 1H), 7.46 (dd, J=8.4 Hz, 2.0 Hz, 1H), 7.54 (d, J=15.6 Hz, 1H), 7.60 (d, J=15.6 Hz, 1H), 7.71-7.73 (m, 2H).

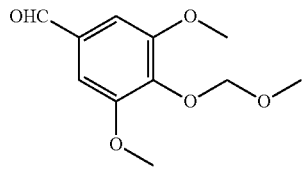 [SMILES: COCOc1c(OC)cc(C=O)cc1OC]

EXAMPLE 41

3,5-dimethoxy-4-(methoxymethoxy)benzaldehyde (SKLBC-30a)

The title compound was prepared from 4-hydroxy-3,5-dimethoxybenzaldehyde by a procedure similar to example 23. $^1$H NMR (CDCl$_3$, 400 MHz) δ: 3.59 (s, 3H), 3.92 (s, 6H), 5.22 (s, 2H), 7.13 (s, 2H), 9.86 (s, 1H).

EXAMPLE 42

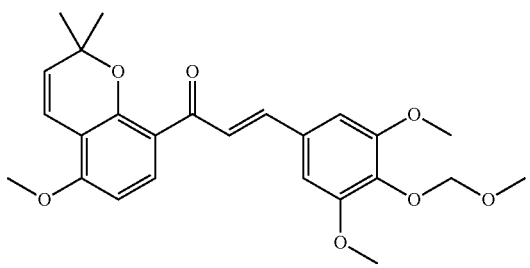

(E)-3-(3,5-dimethoxy-4-(methoxymethoxy)phenyl)-1-(5-methoxy-2,2-dimethyl-2H-chromen-8-yl)prop-2-en-1-one (SKLBC-30b)

The title compound was prepared from SKLBC-30a by a procedure similar to example 2, and the yield was 0.48 g, 55%. $^1$H NMR (CDCl$_3$, 400 MHz) δ: 1.52 (s, 6H), 3.60 (s, 3H), 3.89 (s, 9H), 5.18 (s, 2H), 5.63 (d, J=10.0 Hz, 1H), 6.52 (d, J=8.8 Hz, 1H), 6.70 (d, J=10.0 Hz, 1H), 6.85 (s, 2H), 7.59 (d, J=15.6 Hz, 1H), 7.65 (d, J=15.6 Hz, 1H), 7.73 (d, J=8.8 Hz, 1H).

EXAMPLE 43

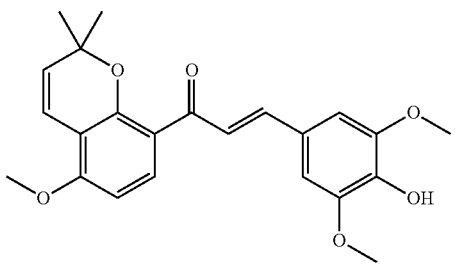

(E)-3-(4-hydroxy-3,5-dimethoxyphenyl)-1-(5-methoxy-2,2-dimethyl-2H-chromen-8-yl)prop-2-en-1-one (SKLBC-30)

The title compound was prepared from SKLBC-30b by a procedure similar to example 25, and the yield was 75%. $^1$H NMR (CDCl$_3$, 400 MHz) δ: 1.52 (s, 6H), 3.90 (s, 3H), 3.93 (s, 6H), 5.63 (d, J=10.0 Hz, 1H), 6.52 (d, J=8.8 Hz, 1H), 6.70 (d, J=10.0 Hz, 1H), 6.87 (s, 2H), 7.63 (s, 2H), 7.72 (d, J=8.8 Hz, 1H).

EXAMPLE 44

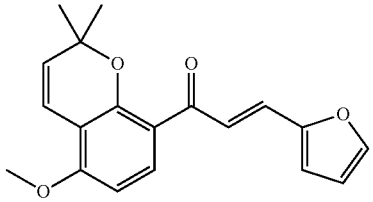 [SMILES: COc1ccc(C(=O)/C=C/c2ccco2)c2c1C=CC(C)(C)O2]

(E)-3-(furan-2-yl)-1-(5-methoxy-2,2-dimethyl-2H-chromen-8-yl)prop-2-en-1-one (SKLBC-31)

The title compound was prepared from furan-2-carbaldehyde by a procedure similar to example 2, and the yield was 0.36 g, 58%. $^1$H NMR (CDCl$_3$, 400 MHz) δ: 1.52 (s, 6H), 3.88 (s, 3H), 5.62 (d, J=10.0 Hz, 1H), 6.48-6.49 (m, 1H), 6.50 (d, J=8.8 Hz, 1H), 6.63 (d, J=3.2 Hz, 1H), 6.71 (d, J=10.0 Hz, 1H), 7.45-7.49 (m, 2H), 7.64 (d, J=15.6 Hz, 1H), 7.71 (d, J=8.8 Hz, 1H).

EXAMPLE 45

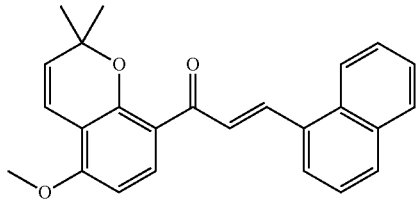 [SMILES: COc1ccc(C(=O)/C=C/c2cccc3ccccc23)c2c1C=CC(C)(C)O2]

(E)-1-(5-methoxy-2,2-dimethyl-2H-chromen-8-yl)-3-(naphthalen-1-yl)prop-2-en-1-one (SKLBC-32)

The title compound was prepared from 1-naphthaldehyde by a procedure similar to example 2, and the yield was 0.58 g, 78%. $^1$H NMR (CDCl$_3$, 400 MHz) δ: 1.51 (s, 6H), 3.90 (s, 3H), 5.63 (d, J=10.0 Hz, 1H), 6.54 (d, J=8.8 Hz, 1H), 6.70 (d, J=10.0 Hz, 1H), 7.49-7.61 (m, 3H), 7.79-7.91 (m, 5H), 8.32 (d, J=8.0 Hz, 1H), 8.53 (d, J=15.6 Hz, 1H).

EXAMPLE 46

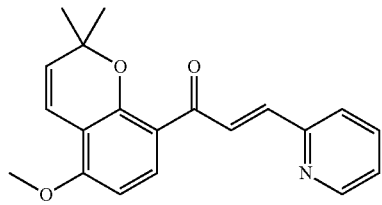 [SMILES: COc1ccc(C(=O)/C=C/c2ccccn2)c2c1C=CC(C)(C)O2]

(E)-1-(5-methoxy-2,2-dimethyl-2H-chromen-8-yl)-3-(pyridin-2-yl)prop-2-en-1-one (SKLBC-33)

The title compound was prepared from picolinaldehyde by a procedure similar to example 2, and the yield was 0.48 g, 75%. $^1$H NMR (CDCl$_3$, 400 MHz) δ: 1.52 (s, 6H), 3.89 (s, 3H), 5.62 (d, J=10.0 Hz, 1H), 6.51 (d, J=8.8 Hz, 1H), 6.70 (d, J=10.0 Hz, 1H), 7.25-7.28 (m, 1H), 7.48 (d, J=8.0 Hz, 1H), 7.62 (d, J=15.6 Hz, 1H), 7.71-7.75 (m, 2H), 8.18 (d, J=15.6 Hz, 1H), 8.66 (d, J=4.4 Hz, 1H).

EXAMPLE 47

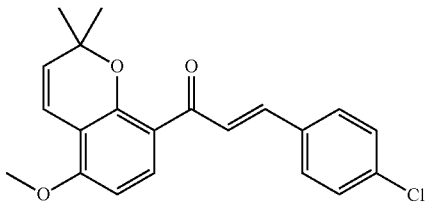 [SMILES: COc1ccc(C(=O)/C=C/c2ccc(Cl)cc2)c2c1C=CC(C)(C)O2]

(E)-3-(4-chlorophenyl)-1-(5-methoxy-2,2-dimethyl-2H-chromen-8-yl)prop-2-en-1-one (SKLBC-34)

The title compound was prepared from 4-chlorobenzaldehyde by a procedure similar to example 2, and the yield was 0.43 g, 61%. $^1$H NMR (CDCl$_3$, 400 MHz) δ: 1.50 (s, 6H), 3.89 (s, 3H), 5.63 (d, J=10.0 Hz, 1H), 6.52 (d, J=8.8 Hz, 1H), 6.69 (d, J=10.0 Hz, 1H), 7.36 (d, J=8.8 Hz, 2H), 7.51 (d, J=8.8 Hz, 2H), 7.60 (d, J=15.6 Hz, 1H), 7.68 (d, J=15.6 Hz, 1H), 7.72 (d, J=8.8 Hz, 1H).

EXAMPLE 48

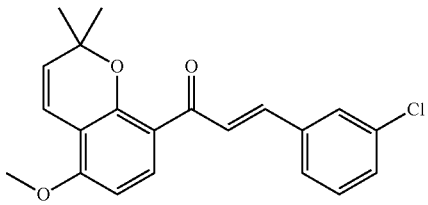 [SMILES: COc1ccc(C(=O)/C=C/c2cccc(Cl)c2)c2c1C=CC(C)(C)O2]

(E)-3-(3-chlorophenyl)-1-(5-methoxy-2,2-dimethyl-2H-chromen-8-yl)prop-2-en-1-one (SKLBC-35)

The title compound was prepared from 3-chlorobenzaldehyde by a procedure similar to example 2, and the yield was 0.39 g, 55%. $^1$H NMR (CDCl$_3$, 400 MHz) δ: 1.52 (s, 6H), 3.90 (s, 3H), 5.64 (d, J=10.0 Hz, 1H), 6.52 (d, J=8.8 Hz, 1H), 6.69 (d, J=10.0 Hz, 1H), 7.33-7.35 (m, 2H), 7.45-7.47 (m, 1H), 7.58 (d, J=15.6 Hz, 1H), 7.59 (s, 1H), 7.72 (d, J=15.6 Hz, 1H), 7.73 (d, J=8.8 Hz, 1H).

EXAMPLE 49

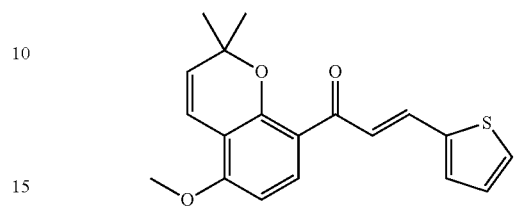

(E)-1-(5-methoxy-2,2-dimethyl-2H-chromen-8-yl)-3-(thiophen-2-yl)prop-2-en-1-one (SKLBC-36)

The title compound was prepared from thiophene-2-carbaldehyde by a procedure similar to example 2, and the yield was 0.31 g, 48%. $^1$H NMR (CDCl$_3$, 400 MHz) δ: 1.55 (s, 6H), 3.89 (s, 3H), 5.63 (d, J=10.0 Hz, 1H), 6.51 (d, J=8.8 Hz, 1H), 6.68 (d, J=10.0 Hz, 1H), 7.06 (dd, J=4.8 Hz, 3.6 Hz, 1H), 7.28 (d, J=3.6 Hz, 1H), 7.34 (d, J=4.8 Hz, 1H), 7.60 (d, J=15.6 Hz, 1H), 7.74 (d, J=8.8 Hz, 1H), 7.82 (d, J=15.6 Hz, 1H).

EXAMPLE 50

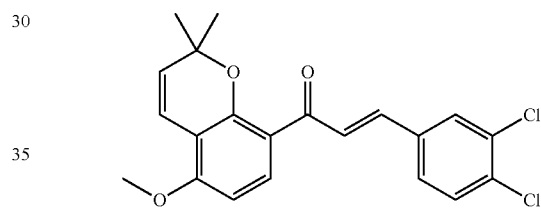

(E)-3-(3,4-dichlorophenyl)-1-(5-methoxy-2,2-dimethyl-2H-chromen-8-yl)prop-2-en-1-one (SKLBC-37)

The title compound was prepared from 3,4-dichlorobenzaldehyde by a procedure similar to example 2, and the yield was 0.43 g, 55%. $^1$H NMR (CDCl$_3$, 400 MHz) δ: 1.51 (s, 6H), 3.90 (s, 3H), 5.64 (d, J=10.0 Hz, 1H), 6.52 (d, J=8.8 Hz, 1H), 6.69 (d, J=10.0 Hz, 1H), 7.39 (dd, J=8.4 Hz, 2.0 Hz, 1H), 7.46 (d, J=8.4 Hz, 1H), 7.53 (d, J=15.6 Hz, 1H), 7.67 (d, J=2.0 Hz, 1H), 7.70 (d, J=15.6 Hz, 1H), 7.73 (d, J=8.8 Hz, 1H).

EXAMPLE 51

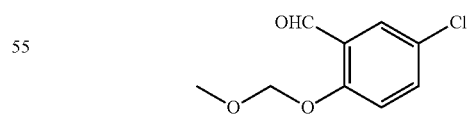

5-chloro-2-(methoxymethoxy)benzaldehyde (SKLBC-38a)

The title compound was prepared from 5-chloro-2-hydroxybenzaldehyde by a procedure similar to example 23. $^1$H-NMR (CDCl$_3$, 400 MHz) δ: 3.49 (s, 3H), 5.26 (s, 2H), 7.16 (d, J=8.8 Hz, 1H), 7.41 (dd, J=9.2, 2.8 Hz, 1H), 7.73 (d, J=2.4 Hz, 1H), 10.39 (s, 1H).

EXAMPLE 52

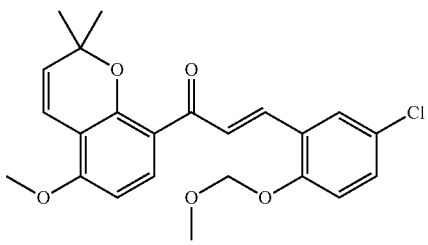 [SMILES: COCOc1ccc(Cl)cc1/C=C/C(=O)c1ccc(OC)c2c1OC(C)(C)C=C2]

(E)-3-(5-chloro-2-(methoxymethoxy)phenyl)-1-(5-methoxy-2,2-dimethyl-2H-chromen-8-yl)prop-2-en-1-one (SKLBC-38b)

The title compound was prepared from SKLBC-38a by a procedure similar to example 2, and the yield was 0.32 g, 39%. $^1$H NMR (CDCl$_3$, 400 MHz) δ: 1.52 (s, 6H), 3.49 (s, 3H), 3.89 (s, 3H), 5.23 (s, 2H), 5.64 (d, J=10.0 Hz, 1H), 6.52 (d, J=8.8 Hz, 1H), 6.69 (d, J=10.0 Hz, 1H), 7.11 (d, J=8.8 Hz, 1,), 7.25 (dd, J=8.8 Hz, 2.4 Hz, 1H), 7.62 (d, J=2.4 Hz, 1H), 7.70 (d, J=15.6 Hz, 1H), 7.73 (d, J=8.8 Hz, 1H), 8.00 (d, J=15.6 Hz, 1H).

EXAMPLE 53

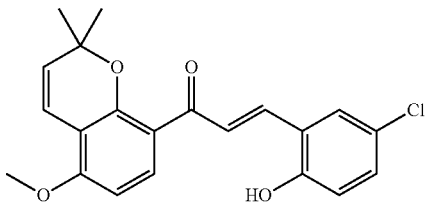 [SMILES: COc1ccc(C(=O)/C=C/c2cc(Cl)ccc2O)c2c1C=CC(C)(C)O2]

(E)-3-(5-chloro-2-hydroxyphenyl)-1-(5-methoxy-2,2-dimethyl-2H-chromen-8-yl)prop-2-en-1-one (SKLBC-38)

The title compound was prepared from SKLBC-38b by a procedure similar to example 25, and the yield was 79%. $^1$H NMR (CDCl$_3$, 400 MHz) δ: 1.52 (s, 6H), 3.90 (s, 3H), 5.63 (d, J=10.0 Hz, 1H), 6.50 (s, 1H), 6.52 (d, J=8.8 Hz, 1H), 6.68 (d, J=10.0 Hz, 1H), 6.85 (d, J=8.8 Hz, 1H), 7.18 (d, J=8.8 Hz, 1H), 7.52 (d, J=2.0 Hz, 1H), 7.74 (d, J=8.8 Hz, 1H), 7.78 (d, J=15.6 Hz, 1H), 7.97 (d, J=15.6 Hz, 1H).

EXAMPLE 54

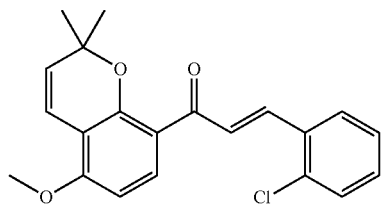 [SMILES: COc1ccc(C(=O)/C=C/c2ccccc2Cl)c2c1C=CC(C)(C)O2]

(E)-3-(2-chlorophenyl)-1-(5-methoxy-2,2-dimethyl-2H-chromen-8-yl)prop-2-en-1-one (SKLBC-39)

The title compound was prepared from 2-chlorobenzaldehyde by a procedure similar to example 2, and the yield was 0.37 g, 52%. $^1$H NMR (CDCl$_3$, 400 MHz) δ: 1.50 (s, 6H), 3.89 (s, 3H), 5.62 (d, J=10.0 Hz, 1H), 6.52 (d, J=8.8 Hz, 1H), 6.68 (d, J=10.0 Hz, 1H), 7.28-7.31 (m, 2H), 7.42-7.44 (m, 1H), 7.70-7.75 (m, 3H), 8.07 (d, J=15.6 Hz, 1H).

EXAMPLE 55

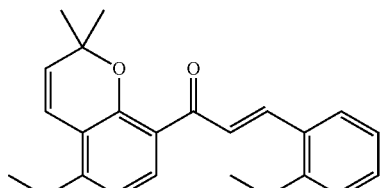

(E)-1-(5-methoxy-2,2-dimethyl-2H-chromen-8-yl)-3-(2-methoxyphenyl)prop-2-en-1-one (SKLBC-40)

The title compound was prepared from 2-methoxybenzaldehyde by a procedure similar to example 2, and the yield was 0.29 g, 41%. $^1$H NMR (CDCl$_3$, 400 MHz) δ: 1.50 (s, 6H), 3.89 (s, 3H), 3.89 (s, 3H), 5.62 (d, J=10.0 Hz, 1H), 6.50 (d, J=8.8 Hz, 1H), 6.68 (d, J=10.0 Hz, 1H), 6.92 (d, J=8.0 Hz, 1H), 6.98 (t, J=7.6 Hz, 1H), 7.35 (t, J=7.6 Hz, 1H), 7.61 (dd, J=8.0 Hz, 1.6 Hz, 1H), 7.69 (d, J=8.8 Hz, 1H), 7.72 (d, J=15.6 Hz, 1H), 8.03 (d, J=15.6 Hz, 1H).

EXAMPLE 56

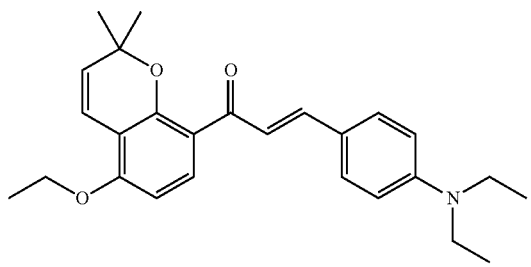 [SMILES: CCOc1ccc(C(=O)/C=C/c2ccc(N(CC)CC)cc2)c2c1C=CC(C)(C)O2]

(E)-3-(4-(diethylamino)phenyl)-1-(5-ethoxy-2,2-dimethyl-2H-chromen-8-yl)prop-2-en-1-one (SKLBC-41)

Compound 9 (188.74 mg, 0.5 mmol) was dissolved in 5 ml acetone, and K$_2$CO$_3$ (1.25 mmol) and dimethyl sulfate (132 μL, 1 mmol) were added to the reaction by drop. Then the reaction was stirred at room temperature for 12 h. When the reaction was completed, K$_2$CO$_3$ was filtered, and the filtration was concentrated under reduce pressure. Then residue was purified by chromatography by silicon gel to give the title compound 40%. $^1$H NMR (400 MHz, CDCl$_3$) δ: 1.20 (t, J=7.2 Hz, 6H), 1.44 (t, J=7.2 Hz, 3H), 1.51 (s, 6H), 3.38 (q, J=7.2 Hz, 4H), 4.07 (q, J=7.2 Hz, 2H), 5.61 (d, J=10.0 Hz, 1H), 6.47 (d, J=8.4 Hz, 1H), 6.65 (d, J=8.4 Hz, 2H), 6.72 (d, J=10.0 Hz, 1H), 7.47-7.53 (m, 3H), 7.65 (d, J=15.6 Hz, 1H) 7.66 (d, J=8.8 Hz, 1H); MS (ESI, m/z): 406.27 [M+H]$^+$.

EXAMPLE 57

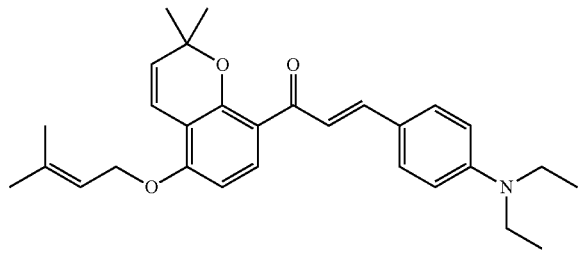 [SMILES: CCN(CC)c1ccc(/C=C/C(=O)c2ccc(OCC=C(C)C)c3c2OC(C)(C)C=C3)cc1]

(E)-3-(4-(diethylamino)phenyl)-1-(2,2-dimethyl-5-((3-methylbut-2-en-1-yl)oxy)-2H-chromen-8-yl)prop-2-en-1-one (SKLBC-42)

The title compound was prepared from 1-bromo-3-methylbut-2-ene by a procedure similar to example 56, and the yield was 42%. $^1$H NMR (400 MHz, CDCl$_3$) δ : 1.20 (t, J=7.2 Hz, 6H), 1.51 (s, 6H), 1.74 (s, 3H), 1.80 (s, 3H), 3.38 (q, J=7.2 Hz, 4H), 4.57 (d, J=6.8 Hz, 2H), 5.48 (t, J=6.8 Hz, 1H), 5.60 (d, J=10.0 Hz, 1H), 6.49 (d, J=8.8 Hz, 1H), 6.64 (d, J=8.0 Hz, 2H), 6.71 (d, J=10.0 Hz, 1H), 7.47 (d, J=8.0 Hz, 2H), 7.49 (d, J=15.2 Hz, 1H), 7.65 (d, J=15.2 Hz, 1H), 7.66 (d, J=8.8 Hz, 1H); MS (ESI, m/z): 446.26 [M+H]$^+$.

EXAMPLE 58

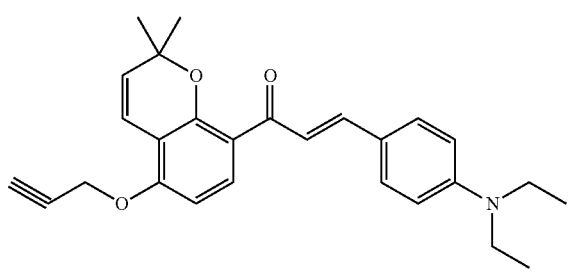 [SMILES: C#CCOc1ccc(C(=O)/C=C/c2ccc(N(CC)CC)cc2)c2c1C=CC(C)(C)O2]

(E)-3-(4-(diethylamino)phenyl)-1-(2,2-dimethyl-5-(prop-2-yn-1-yloxy)-2H-chromen-8-yl)prop-2-en-1-one (SKLBC-43)

The title compound was prepared from 3-bromoprop-1-yne by a procedure similar to example 56, and the yield was 45%. $^1$H NMR (400 MHz, CDCl$_3$) δ : 1.22 (t, J=7.2 Hz, 6H), 1.51 (s, 6H), 2.55 (t, J=2.0 Hz, 1H), 3.40 (q, J=7.2 Hz, 4H), 4.76 (d, J=2.0 Hz, 2H), 5.63 (d, J=10.0 Hz, 1H), 6.59 (d, J=8.8 Hz, 1H), 6.65 (d, J=8.0 Hz, 2H), 6.70 (d, J=10.0 Hz, 1H), 7.42-7.51 (m, 3H), 7.64 (d, J=15.2 Hz, 1H), 7.65 (d, J=8.8 Hz, 1H); MS (ESI, m/z): 416.21 [M+H]$^+$.

EXAMPLE 59

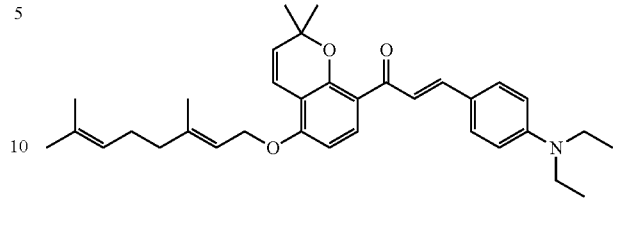

(E)-3-(4-(diethylamino)phenyl)-1-(5-(((E)-3,7-dimethylocta-2,6-dien-1-yl)oxy)-2,2-dimethyl-2H-chromen-8-yl)prop-2-en-1-one (SKLBC-44)

The title compound was prepared from (E)-1-bromo-3,7-dimethylocta-2,6-diene by a procedure similar to example 56, and the yield was 37%. $^1$H NMR (400 MHz, CDCl$_3$) δ: 1.20 (t, J=7.2 Hz, 6H), 1.25 (s, 6H), 1.51 (s, 6H), 1.68 (s, 3H), 2.08-2.03 (m, 4H), 3.38 (q, J=7.2 Hz, 4H), 4.56-4.61 (m, 2H), 5.08-5.11 (m, 1H), 5.46-5.49 (m, 1H), 5.60 (d, J=10.0 Hz, 1H), 6.49 (d, J=8.8 Hz, 1H), 6.64 (d, J=8.4 Hz, 2H), 6.71 (d, J=10.0 Hz, 1H), 7.47 (d, J=8.4 Hz, 2H), 7.49 (d, J=15.6 Hz, 1H), 7.65 (d, J=15.6 Hz, 1H), 7.66 (d, J=8.8 Hz, 1H). MS (ES), m/z: 514.32 (ES+).

EXAMPLE 60

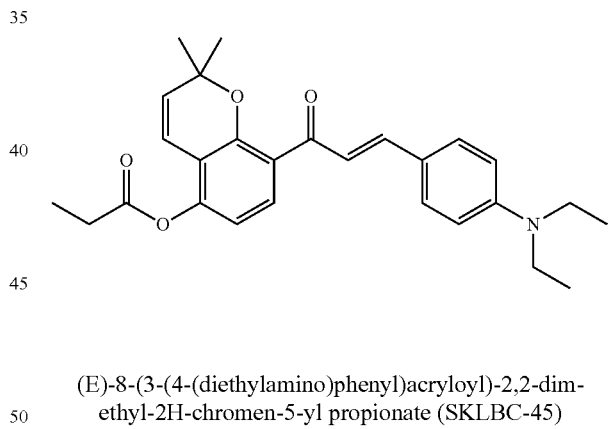

(E)-8-(3-(4-(diethylamino)phenyl)acryloyl)-2,2-dimethyl-2H-chromen-5-yl propionate (SKLBC-45)

Compound 9 (188.74 mg, 0.5 mmol) was dissolved in 3 mL pyridine. Propionic anhydride (838.91 μL, 6.5 mmol) was added to the reaction. Then the reaction was stirred at room temperature for 12 h. When the reaction was completed, the solvent was removed by reduce pressure, the residue was poured into 30 mL H$_2$O, extracted by ethyl acetate, dried by Na$_2$SO$_4$, concentrated by reduce pressure, and purified by chromatography by silicon gel to give the target compound 50%. $^1$H NMR (400 MHz, CDCl$_3$) δ: 1.20 (t, J=7.2 Hz, 6H), 1.30 (t, J=7.6 Hz, 3H), 1.50 (s, 6H), 2.61 (q, J=7.6 Hz, 2H), 3.38 (q, J=7.2 Hz, 4H), 5.70 (d, J=10.0 Hz, 1H), 6.36 (d, J=10.0 Hz, 1H), 6.64 (d, J=8.0 Hz, 2H), 6.69 (d, J=8.8 Hz, 1H), 7.28 (d, J=15.6 Hz, 1H), 7.46 (d, J=8.0 Hz, 2H), 7.55 (d, J=8.8 Hz, 1H), 7.61 (d, J=15.6 Hz, 1H); MS (ESI, m/z): 434.22 [M+H]$^+$.

EXAMPLE 61

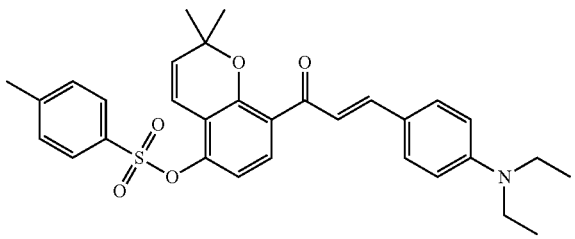 [SMILES: CCN(CC)c1ccc(/C=C/C(=O)c2ccc(OS(=O)(=O)c3ccc(C)cc3)c3c2OC(C)(C)C=C3)cc1]

(E)-8-(3-(4-(diethylamino)phenyl)acryloyl)-2,2-dimethyl-2H-chromen-5-yl 4-methylbenzenesulfonate (SKLBC-46)

Compound 9 (188.74 mg, 0.5 mmol) was dissolved in 5 mL DCM. paratoluensulfonyl chloride (172.20 μL, 1.25 mmol) and triethylamine (140 μL, 1 mmol) were added to the reaction. Then the reaction was stirred at room temperature for 12 h. When the reaction was completed, the reaction was poured into 30 mL H$_2$O, extracted by ethyl acetate, dried by Na$_2$SO$_4$, concentrated by reduce pressure, and purified by chromatography by silicon gel to give the target compound 47%. $^1$H NMR (400 MHz, CDCl$_3$) δ: 1.20 (t, J=7.2 Hz, 6H), 1.39 (s, 6H), 2.45 (s, 3H), 3.39 (q, J=7.2 Hz, 4H), 5.58 (d, J=10.0 Hz, 1H), 6.40 (d, J=10.4 Hz, 1H), 6.60 (d, J=8.8 Hz, 1H), 6.64 (d, J=8.0 Hz, 2H), 7.21 (d, J=8.8 Hz, 1H), 7.31 (d, J=8.4 Hz, 2H), 7.42 (d J=15.6 Hz, 1H), 7.44 (d, J=8.0 Hz, 2H), 7.57 (d, J=15.6 Hz, 1H), 7.73 (d, J=8.4 Hz, 2H). MS (ESI, m/z): 532.23 [M+H]$^+$.

EXAMPLE 62

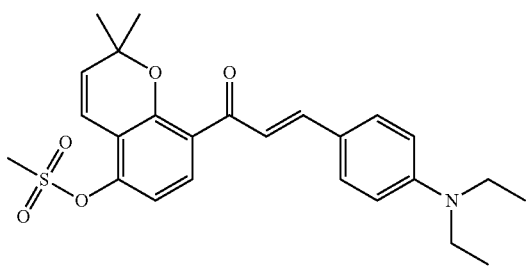 [SMILES: CCN(CC)c1ccc(/C=C/C(=O)c2ccc(OS(C)(=O)=O)c3c2OC(C)(C)C=C3)cc1]

(E)-8-(3-(4-(diethylamino)phenyl)acryloyl)-2,2-dimethyl-2H-chromen-5-yl methanesulfonate (SKLBC-47)

The title compound was prepared from methylsulfonyl chloride by a procedure similar to example 61, and the yield was 31%. $^1$H NMR (400 MHz, CDCl$_3$) δ: 1.22 (t, J=7.2 Hz, 6H), 1.50 (s, 6H), 3.20 (s, 3H), 3.39 (q, J=7.2 Hz, 4H), 5.78 (d, J=10.0 Hz, 1H), 6.63 (d, J=10.0 Hz, 1H), 6.66 (d, J=8.4 Hz, 2H), 6.91 (d, J=8.4 Hz, 1H), 7.23 (d, J=15.6 Hz, 1H), 7.46 (d, J=8.4 Hz, 2H), 7.53 (d, J=8.4 Hz, 1H), 7.59 (d, J=15.6 Hz, 1H).

MS (ESI, m/z): 456.17 [M+H]$^+$.

EXAMPLE 63

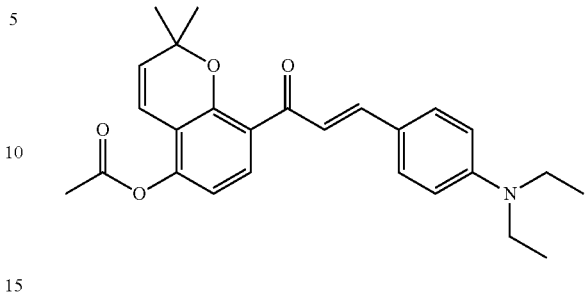

(E)-8-(3-(4-(diethylamino)phenyl)acryloyl)-2,2-dimethyl-2H-chromen-5-yl acetate (SKLBC-48)

The title compound was prepared from acetyl chloride by a procedure similar to example 61, and the yield was 43%. $^1$H NMR (400 MHz, CDCl$_3$) δ: 1.20 (t, J=7.2 Hz, 6H), 1.50 (s, 6H), 2.35 (s, 3H), 3.38 (q, J=7.2 Hz, 4H), 5.71 (d, J=10.0 Hz, 1H), 6.38 (d, J=10.0 Hz, 1H), 6.64 (d, J=8.0 Hz, 2H), 6.69 (d, J=8.4 Hz, 1H), 7.28 (d, J=15.6 Hz, 1H), 7.46 (d, J=8.0 Hz, 2H), 7.55 (d, J=8.4 Hz, 1H), 7.61 (d, J=15.6 Hz, 1H). MS (ESI, m/z): 420.22 [M+H]$^+$.

EXAMPLE 64

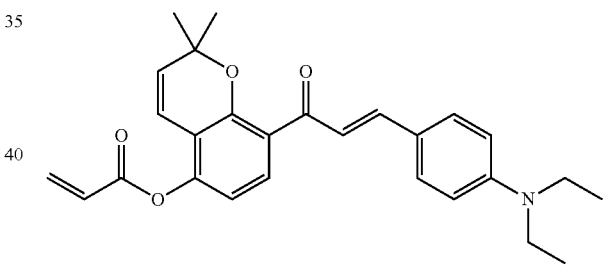

(E)-8-(3-(4-(diethylamino)phenyl)acryloyl)-2,2-dimethyl-2H-chromen-5-yl acrylate (SKLBC-49)

Compound 9 (188.74 mg, 0.5 mmol), acroleic acid (72.06 mg, 1 mmol), EDCI (155.24 mg, 1 mmol) and DMAP (30.54 mg, 0.25 mmol) were dissolved in 5 mL DCM, and the result solution was stirred at room temperature for 12 h. When the reaction was completed, the reaction was poured into 30 mL H$_2$O, extracted by ethyl acetate, dried by Na$_2$SO$_4$, concentrated by reduce pressure, and purified by chromatography by silicon gel to give the target compound 45%. $^1$H NMR (400 MHz, CDCl$_3$) δ: 1.20 (t, J=7.2 Hz, 6H), 1.50 (s, 6H), 3.39 (q, J=7.2 Hz, 4H), 5.70 (d, J=10.0 Hz, 1H), 6.06 (dd, J=1.2 Hz, J=10.4 Hz, 1H), 6.32-6.39 (m, 1H), 6.37 (d, J=10.0 Hz, 1H), 6.64 (d, J=8.4 Hz, 2H), 6.68 (d, J=1.2 Hz, 1H), 6.73 (d, J=8.8 Hz, 1H), 7.29 (d, J=15.6 Hz, 1H), 7.46 (d, J=8.4 Hz, 2H), 7.56 (d, J=8.8 Hz, 1H), 7.62 (d, J=15.6 Hz, 1H). MS (ESI, m/z): 432.19 [M+H]$^+$.

EXAMPLE 65

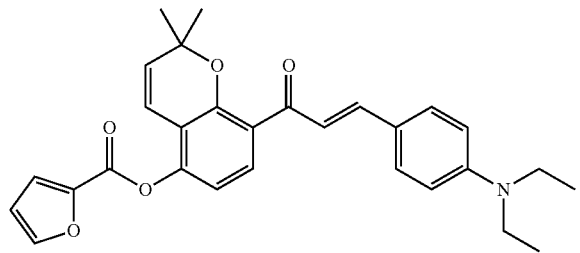 [SMILES: CCN(CC)c1ccc(/C=C/C(=O)c2ccc(OC(=O)c3ccco3)c3c2OC(C)(C)C=C3)cc1]

(E)-8-(3-(4-(diethylamino)phenyl)acryloyl)-2,2-dimethyl-2H-chromen-5-yl furan-2-carboxylate (SKLBC-50)

The title compound was prepared from pyromucic acid by a procedure similar to example 64, and the yield was 39%. $^1$H NMR (400 MHz, CDCl$_3$) δ: 1.22 (t, J=7.2 Hz, 6H), 1.51 (s, 6H), 3.44 (q, J=7.2 Hz, 4H), 5.70 (d, J=10.0 Hz, 1H), 6.45 (d, J=10.0 Hz, 1H), 6.62 (dd, J=1.2 Hz, J=3.2 Hz, 1H), 6.65 (d, J=8.4 Hz, 2H), 6.82 (d, J=8.4 Hz, 1H), 7.29 (d, J=15.6 Hz, 1H), 7.43 (d, J=3.2 Hz, 1H), 7.47 (d, J=8.4 Hz, 2H), 7.58 (d, J=8.4 Hz, 1H), 7.62 (d, J=15.6 Hz, 1H), 7.71 (d, J=1.2 Hz, 1H). MS (ESI, m/z): 472.19 [M+H]$^+$.

EXAMPLE 66

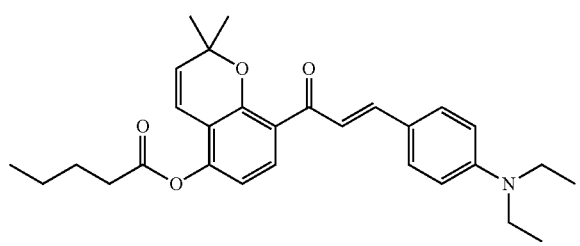 [SMILES: CCCCC(=O)Oc1ccc(C(=O)/C=C/c2ccc(N(CC)CC)cc2)c2c1C=CC(C)(C)O2]

(E)-8-(3-(4-(diethylamino)phenyl)acryloyl)-2,2-dimethyl-2H-chromen-5-ylpentanoate (SKLBC-51)

The title compound was prepared from valeric anhydride by a procedure similar to example 60, and the yield was 43%. $^1$H NMR (400 MHz, CDCl$_3$) δ: 0.94 (t, J=7.2 Hz, 3H), 1.25 (t, J=7.2 Hz, 6H), 1.50 (s, 6H), 1.60 (quint, J=7.2 Hz, J=14.8 Hz, 2H), 1.80 (sext, J=7.6 Hz, J=15.2 Hz, 2H), 2.37 (t, J=7.6 Hz, 2H), 3.47 (q, J=7.2 Hz, 4H), 5.70 (d, J=10.0 Hz, 1H), 6.35 (d, J=10.0 Hz, 1H), 6.64 (d, J=8.0 Hz, 2H), 6.68 (d, J=8.8 Hz, 1H), 7.28 (d, J=15.6 Hz, 1H), 7.45 (d, J=8.0 Hz, 2H), 7.61 (d, J=15.6 Hz, 1H) 7.65 (d, J=8.8 Hz, 1H). MS (ESI, m/z): 462.22 [M+H]$^+$.

EXAMPLE 67

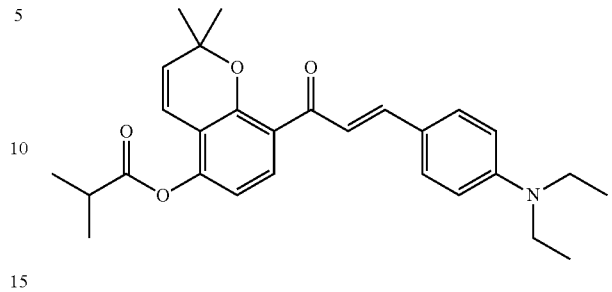

(E)-8-(3-(4-(diethylamino)phenyl)acryloyl)-2,2-dimethyl-2H-chromen-5-yl isobutyrate (SKLBC-52)

The title compound was prepared from isopropyl anhydride by a procedure similar to example 60, and the yield was 46%. $^1$H NMR (400 MHz, CDCl$_3$) δ : 1.21 (t, J=7.2 Hz, 6H), 1.34 (d, J=15.2 Hz, 6H), 1.50 (s, 6H), 2.79-2.89 (m, 1H), 3.41 (q, J=7.2 Hz, 4H), 5.69 (d, J=10.0 Hz, 1H), 6.35 (d, J=10.0 Hz, 1H), 6.64 (d, J=8.0 Hz, 2H), 6.67 (d, J=8.8 Hz, 1H), 7.29 (d, J=15.6 Hz, 1H), 7.42 (d, J=8.0 Hz, 2H), 7.55 (d, J=8.8 Hz, 1H), 7.61 (d, J=15.6 Hz, 1H). MS (ESI, m/z): 448.20 [M+H]$^+$.

EXAMPLE 68

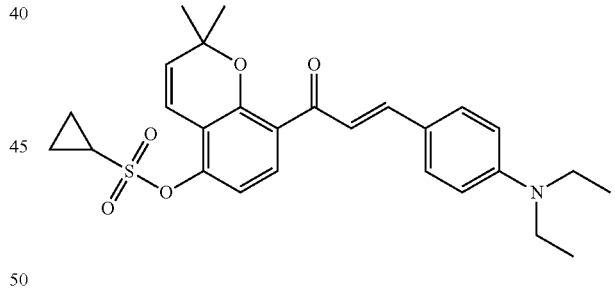

(E)-8-(3-(4-(diethylamino)phenyl)acryloyl)-2,2-dimethyl-2H-chromen-5-yl cyclopropanesulfonate (SKLBC-53)

The title compound was prepared from cyclopropane sulfonyl chloride by a procedure similar to example 61, and the yield was 38%. $^1$H NMR (400 MHz, CDCl$_3$) δ: 0.83-0.89 (m, 2H), 1.22 (t, J=7.2 Hz, 6H), 1.31-1.35 (m, 2H), 1.50 (s, 6H), 2.67 (quint, 1H), 3.40 (q, J=7.2 Hz, 4H), 5.77 (d, J=10.0 Hz, 1H), 6.66 (d, J=8.0 Hz, 2H), 6.69 (d, J=10.0 Hz, 1H), 6.95 (d, J=8.8 Hz, 1H), 7.23 (d, J=15.6 Hz, 1H), 7.47 (d, J=8.0 Hz, 2H), 7.53 (d, J=8.8 Hz, 1H), 7.60 (d, J=15.6 Hz, 1H). MS (ESI, m/z): 482.13 [M+H]$^+$.

EXAMPLE 69

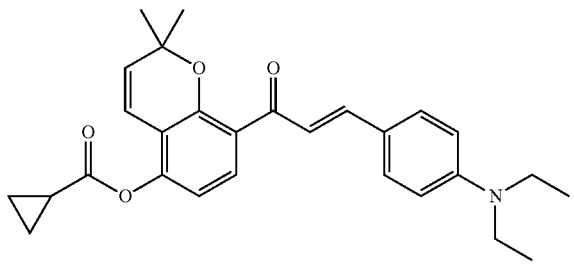 [SMILES: CCN(CC)c1ccc(/C=C/C(=O)c2ccc(OC(=O)C3CC3)c3c2OC(C)(C)C=C3)cc1]

(E)-8-(3-(4-(diethylamino)phenyl)acryloyl)-2,2-dimethyl-2H-chromen-5-yl cyclopropanecarboxylate (SKLBC-54)

The title compound was prepared from cyclopropane carboxylic acid by a procedure similar to example 64, and the yield was 30%. $^1$H NMR (400 MHz, CDCl$_3$) δ: 0.94 (m, 2H), 1.14 (m, 2H), 1.21 (t, J=7.2 Hz, 6H), 1.49 (s, 6H), 1.90 (quint, J=4.4 Hz, J=8.0 Hz, 1H), 3.42 (q, J=7.2 Hz, 4H), 5.69 (d, J=10.0 Hz, 1H), 6.39 (d, J=10.0 Hz, 1H), 6.63 (d, J=8.0 Hz, 2H), 6.68 (d, J=8.4 Hz, 1H), 7.28 (d, J=15.6 Hz, 1H), 7.45 (d, J=8.0 Hz, 2H), 7.53 (d, J=8.4 Hz, 1H), 7.60 (d, J=15.6 Hz, 1H). MS (ESI, m/z): 446.21 [M+H]$^+$.

EXAMPLE 70

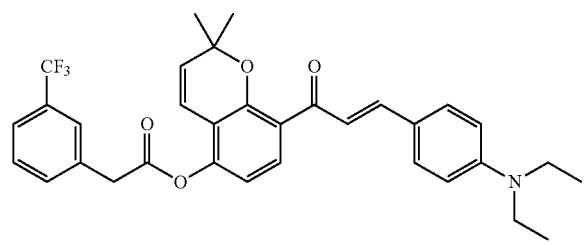 [SMILES: CCN(CC)c1ccc(/C=C/C(=O)c2ccc(OC(=O)Cc3cccc(C(F)(F)F)c3)c3c2OC(C)(C)C=C3)cc1]

(E)-8-(3-(4-(diethylamino)phenyl)acryloyl)-2,2-dimethyl-2H-chromen-5-yl 2-(3-(trifluoromethyl)phenyl)acetate (SKLBC-55)

The title compound was prepared from m-(trifluoromethyl)phenylacetic acid by a procedure similar to example 64, and the yield was 35%. $^1$H NMR (400 MHz, CDCl$_3$) δ: 1.20 (t, J=7.2 Hz, 6H), 1.47 (s, 6H), 3.38 (q, J=6.8 Hz, 4H), 3.97 (s, 2H), 5.63 (d, J=10.0 Hz, 1H), 6.11 (d, J=10.40 Hz, 1H), 6.64 (d, J=8.0 Hz, 2H), 6.68 (d, J=8.8 Hz, 1H), 7.26 (d, J=15.6 Hz, 1H), 7.45-7.50 (m, 3H), 7.52-7.62 (m, 3H), 7.59 (d, J=8.8 Hz, 1H), 7.63 (d, J=15.6 Hz, 1H). MS (ESI, m/z): 564.19 [M+H]$^+$.

EXAMPLE 71

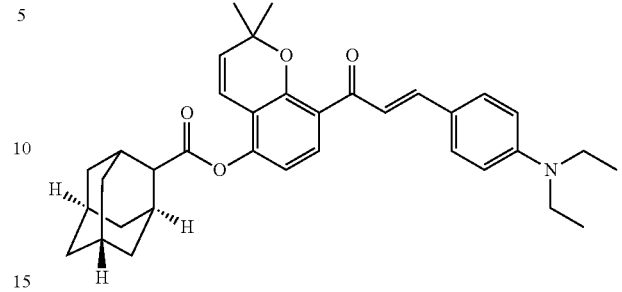

(1r,3r,5r,7r)-8-((E)-3-(4-(diethylamino)phenyl)acryloyl)-2,2-dimethyl-2H-chromen-5-yl adamantane-2-carboxylate (SKLBC-56)

The title compound was prepared from (1r,3r,5r,7r-adamantane-2-carboxylic acid by a procedure similar to example 64, and the yield was 33%. $^1$H NMR (400 MHz, CDCl$_3$) δ: 1.21 (t, J=7.2 Hz, 6H,), 1.49 (s, 6H), 1.63-2.09 (m, 15H), 3.41 (q, J=7.2 Hz, 4H), 5.68 (d, J=10.0 Hz, 1H), 6.33 (d, J=10.0 Hz, 1H), 6.21-6.64 (m, 3H), 7.28 (d, J=15.6 Hz, 1H), 7.46 (d, J=8.0 Hz, 2H), 7.54 (d, J=8.4 Hz, 1H), 7.60 (d, J=15.2 Hz, 1H). MS (ESI, m/z): 540.29 [M+H]$^+$.

EXAMPLE 72

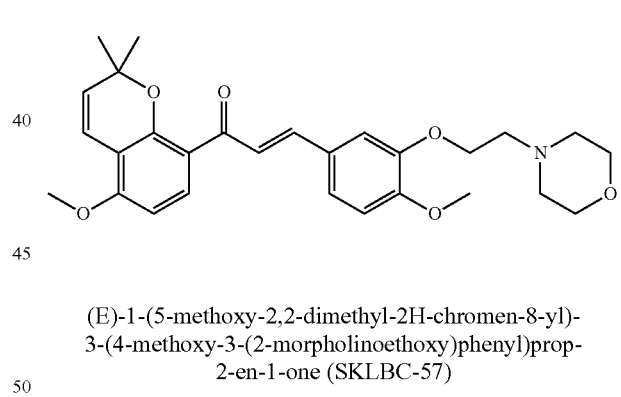

(E)-1-(5-methoxy-2,2-dimethyl-2H-chromen-8-yl)-3-(4-methoxy-3-(2-morpholinoethoxy)phenyl)prop-2-en-1-one (SKLBC-57)

To a solution of compound SKLBC-28 (0.59 g, 1.6 mmol) in anhydrous DMF (5 mL) under nitrogen was added NaH (0.38 g of a 60% dispersion, 9.5 mmol, 6 equiv). The mixture was stirred at room temperature over 30 min, by which point H$_2$ evolution had ceased. The reaction mixture was heated to 90° C., and 4-(2-chloroethyl)morpholine (3.6 mmol, 2.25 equiv) was added in portions over 30 min. The reaction mixture was stirred at 90° C. for another 12 h. The completion of the reaction was monitored by TLC. On completion, the mixture was cooled to ambient temperature, and H$_2$O (3 mL) was added to destroy excess NaH. The slurry was partitioned between water (50 mL) and ethyl acetate (50 mL), and the water was extracted with ethyl acetate (3×20 mL). The combined ethereal extract was dried (Na$_2$SO$_4$), filtered, and concentrated in vacuo to yield a brown oil. Chromatographic separation (hexanes-ethyl acetate-triethylamine, 10:5:1) gave the product as a pale yellow oil. 23.3%. $^1$H NMR (CDCl$_3$, 400 MHz) δ:1.50 (s, 6H), 2.63 (t, J=4.8 Hz, 4H), 2.90 (t, J=5.6 Hz, 2H), 3.75 (t, J=4.8 Hz, 4H), 3.90 (s, 6H), 4.19 (t, J=5.6z, 4H), 5.62 (d, J=10.0 Hz, 1H), 6.51 (d, J=8.8 Hz, 1H), 6.69 (d, J=10.0 Hz, 1H), 6.88 (d, J=8.4 Hz, 1H), 7.16 (d, J=2.0 Hz, 1H), 7.19 (dd, J=8.8 Hz, 2.0 Hz, 1H), 7.52 (d, J=16.0 Hz, 1H), 7.60 (d, J=16.0 Hz, 1H), 7.69 (d, J=8.4 Hz, 1H) MS(ES+): m/z=480.31.

EXAMPLE 73

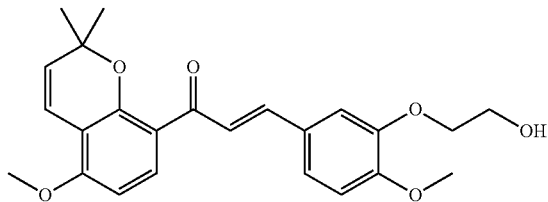 [SMILES: COc1ccc(/C=C/C(=O)c2ccc(OC)c3c2OC(C)(C)C=C3)cc1OCCO]

(E)-3-(3-(2-hydroxyethoxy)-4-methoxyphenyl)-1-(5-methoxy-2,2-dimethyl-2H-chromen-8-yl)prop-2-en-1-one (SKLBC-58)

SKLBC-28 (220.9 mg, 0.6 mmol), ethylene carbonate (184.8 mg, 2.1 mmol) and K$_2$CO$_3$ (248.8 mg, 1.8 mmol) were added in anhydrous CH$_3$CN (6 mL). The reaction mixture was stirred at reflux for 12 h and monitored by TLC. When the reaction was completed, 15 mL H$_2$O was added, and subsequently extracted with DCM. The organic layers were combined, and washed with 3 N NaOH, then brine. The organic layer was dried over sodium sulfate and concentrated in vacuo. The resulting residue was purified by flash chromatography using petroleum ether/ethyl acetate (4:1) as eluent to yield light yellow solids 69.5%. $^1$H NMR (CDCl$_3$, 400 MHz) δ: 1.51 (s, 6H), 3.89 (s, 6H), 3.97 (t, J=4.4 Hz, 2H), 4.16 (t, J=4.4 Hz, 2H), 5.62 (d, J=10.0 Hz, 1H), 6.51 (d, J=8.8 Hz, 1H), 6.69 (d, J=10.0 Hz, 1H), 6.90 (d, J=8.8 Hz, 1H), 7.20 (d, J=1.6 Hz, 1H), 7.21 (dd, J=8.8 Hz, 1.6 Hz, 1H), 7.57 (d, J=16.0 Hz, 1H), 7.62 (d, J=16.0 Hz, 1H), 7.70 (d, J=8.8 Hz, 1H) MS(ES+): m/z=411.27

EXAMPLE 74

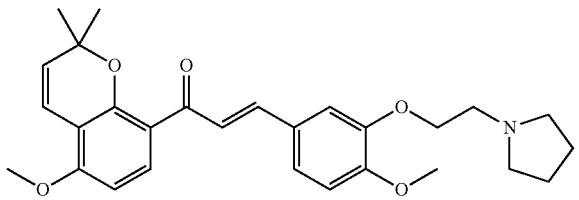 [SMILES: COc1ccc(/C=C/C(=O)c2ccc(OC)c3c2OC(C)(C)C=C3)cc1OCCN1CCCC1]

(E)-1-(5-methoxy-2,2-dimethyl-2H-chromen-8-yl)-3-(4-methoxy-3-(2-(pyrrolidin-1-yl)ethoxy)phenyl) prop-2-en-1-one (SKLBC-59)

The title compound was prepared from 1-(2-chloroethyl) pyrrolidine by a procedure similar to example 72, and the yield was 65.1%. $^1$H NMR (CDCl$_3$, 400 MHz) δ:1.51 (s, 6H), 1.82 (m, 4H), 2.66 (m, 4H), 2.98 (t, J=6.4 Hz, 2H), 3.84 (s, 6H), 4.20 (t, J=6.4 Hz, 2H), 5.62 (d, J=10.0 Hz, 1H), 6.51 (d, J=8.4 Hz, 1H), 6.69 (d, J=10.0 Hz, 1H), 6.88 (d, J=8.4 Hz, 1H), 7.17 (d, J=1.6 Hz, 1H), 7.18 (dd, J=8.4 Hz, 1.6 Hz, 1H), 7.55 (d, J=15.6 Hz, 1H), 7.62 (d, J=15.6 Hz, 1H), 7.70 (d, J=8.4 Hz, 1H) MS(ES+): m/z=464.31

EXAMPLE 75

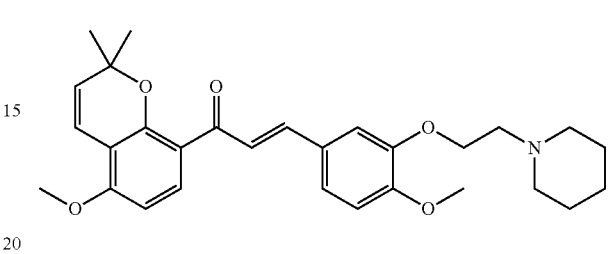

(E)-1-(5-methoxy-2,2-dimethyl-2H-chromen-8-yl)-3-(4-methoxy-3-(2-(piperidin-1-yl)ethoxy)phenyl) prop-2-en-1-one (SKLBC-60)

The title compound was prepared from 1-(2-chloroethyl) piperidine by a procedure similar to example 72, and the yield was 53.4%. $^1$H NMR (CDCl$_3$, 400 MHz) δ:1.24-1.28 (m, 2H), 1.51 (s, 6H), 1.62-1.64 (m, 4H), 2.57 (m, 4H), 2.89 (t, J=6.4 Hz, 2H), 3.84 (s, 6H), 4.20 (t, J=6.4 Hz, 2H), 5.62 (d, J=10.0 Hz, 1H), 6.51 (d, J=8.8 Hz, 1H), 6.69 (d, J=10.0 Hz, 1H), 6.88 (d, J=8.0 Hz, 1H), 7.17-7.20 (m, 2H), 7.56 (d, J=15.6 Hz, 1H), 7.62 (d, J=15.6 Hz, 1H), 7.70 (d, J=8.8 Hz, 1H) MS(ES+): m/z=478.36

EXAMPLE 76

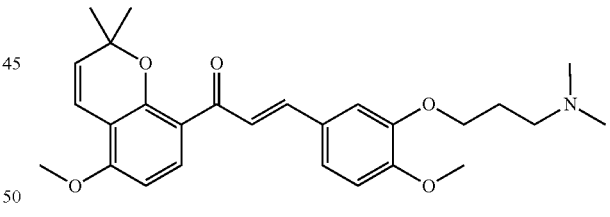

(E)-3-(3-(3-(dimethylamino)propoxy)-4-methoxyphenyl)-1-(5-methoxy-2,2-dimethyl-2H-chromen-8-yl)prop-2-en-1-one (SKLBC-61)

The title compound was prepared from 3-chloro-N,N-dimethylpropan-1-amine by a procedure similar to example 72, and the yield was 59.4%. $^1$H NMR (CDCl$_3$, 400 MHz) δ: 1.50 (s, 6H), 2.04-2.07 (m, 2H), 2.28 (s, 6H), 2.51 (t, J=6.4 Hz, 2H), 3.85 (s, 6H), 4.09 (t, J=6.4 Hz, 2H), 5.61 (d, J=10.0 Hz, 1H), 6.50 (d, J=9.2 Hz, 1H), 6.68 (d, J=10.0 Hz, 1H), 6.86 (d, J=8.0 Hz, 1H), 7.15-7.17 (m, 2H), 7.56 (d, J=16.0 Hz, 1H), 7.61 (d, J=16.0 Hz, 1H), 7.69 (d, J=8.0 Hz, 1H) MS(ES+): m/z=452.30

EXAMPLE 77

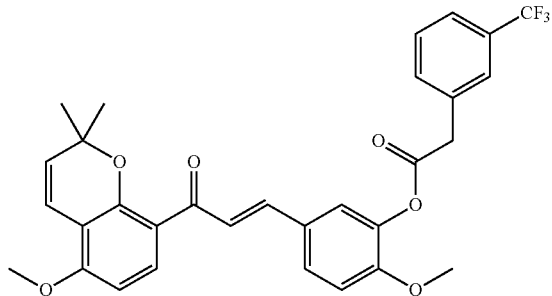 [SMILES: COc1ccc(/C=C/C(=O)c2ccc(OC)c3c2OC(C)(C)C=C3)cc1OC(=O)Cc1cccc(C(F)(F)F)c1]

(E)-2-methoxy-5-(3-(5-methoxy-2,2-dimethyl-2H-chromen-8-yl)-3-oxoprop-1-en-1-yl)phenyl 2-(3-(trifluoromethyl)phenyl)acetate (SKLBC-62)

SKLBC-28 (147.3 mg, 0.4 mmol), m-(trifluoromethyl)phenylacetic acid (0.45 mmol), EDCI (115.0 mg, 0.6 mmol) and DMAP (24.4 mg, 0.2 mmol) were dissolved in 10 mL DCM, and the result solution was stirred at room temperature for 12 h. When the reaction was completed, the reaction was poured into 30 mL H$_2$O, extracted by ethyl acetate, dried by Na$_2$SO$_4$, concentrated by reduce pressure, and purified by chromatography by silicon gel to give the target compound 152 mg, 45%. H-NMR (CDCl$_3$, 400 MHz) δ: 1.44 (s, 6H), 3.80 (s, 3H), 3.87 (s, 3H), 3.96 (s, 2H), 5.60 (d, 1H, J=10.4 Hz), 6.49 (d, 1H, J=9.2 Hz), 6.67 (d, 1H, J=10.4 Hz), 6.94 (d, 1H, J=8.4 Hz), 7.25-7.27 (m, 2H), 7.42 (d, 1H, J=8.8 Hz), 7.49 (d, 1H, J=8.0 Hz), 7.56-7.60 (m, 3H), 7.68-7.98 (m, 2H) MS(ES+): m/z=553.27

EXAMPLE 78

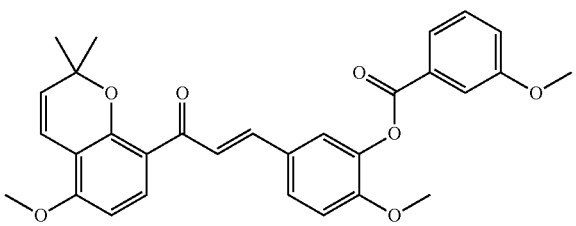

(E)-2-methoxy-5-(3-(5-methoxy-2,2-dimethyl-2H-chromen-8-yl)-3-oxoprop-1-en-1-yl)phenyl 3-methoxybenzoate (SKLBC-63)

The title compound was prepared from 3-methoxybenzoic acid by a procedure similar to example 77, and the yield was 81.9%. $^1$H NMR (CDCl$_3$, 400 MHz) δ: 1.49 (s, 6H), 3.86 (s, 9H), 5.61 (d, J=10.0 Hz, 1H), 6.50 (d, J=8.8 Hz, 1H), 6.67 (d, J=10.0 Hz, 1H), 7.02 (d, J=8.4 Hz, 1H), 7.18 (dd, J=8.8 Hz, 2.4 Hz, 1H), 7.40-7.43 (m, 2H,) 7.49 (d, J=8.4 Hz, 1H), 7.57 (q, J=16.0 Hz, 1H), 7.62 (d, J=16.0 Hz, 1H), 7.69-7.72 (m, 2H), 7.82 (d, J=8.4 Hz, 1H) MS(ES+): m/z=501.24.

EXAMPLE 79

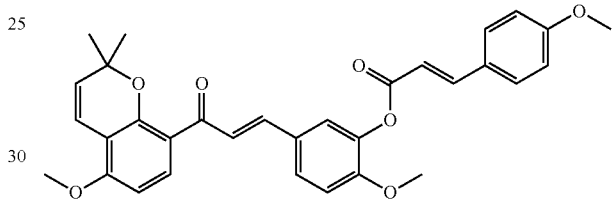

(E)-2-methoxy-5-((E)-3-(5-methoxy-2,2-dimethyl-2H-chromen-8-yl)-3-oxoprop-1-en-1-yl)phenyl 3-(4-methoxyphenyl)acrylate (SKLBC-64)

The title compound was prepared from (E)-3-(4-methoxyphenyl)acrylic acid by a procedure similar to example 77, and the yield was 81.9%. $^1$H NMR (CDCl$_3$, 400 MHz) δ: 1.49 (s, 6H), 3.86 (s, 9H), 5.61 (d, J=10.0 Hz, 1H), 6.51 (d, J=8.8 Hz, 1H), 6.53 (d, J=15.6 Hz, 1H), 6.67 (d, J=10.0 Hz, 1H), 6.93 (d, J=8.4 Hz, 2H), 7.00 (d, J=8.8 Hz, 1H), 7.38 (s, 1H), 7.46 (d, J=7.6 Hz, 1H), 7.55 (d, J=7.6 Hz, 2H), 7.57 (d, J=14.8 Hz, 1H), 7.62 (d, J=14.8 Hz, 1H), 7.70 (d, J=7.6 Hz, 1H), 7.83 (d, J=15.6 Hz, 1H) MS(ES+):m/z=527.26.

EXAMPLE 80

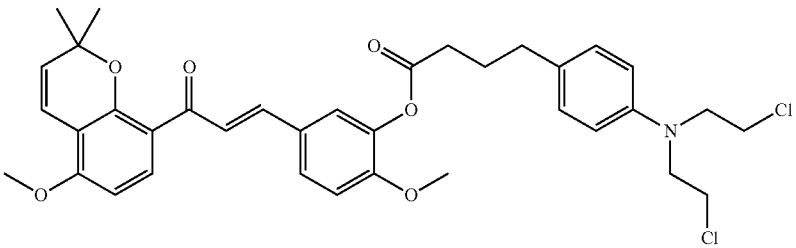 [SMILES: COc1ccc(/C=C/C(=O)c2ccc(OC)c3c2OC(C)(C)C=C3)cc1OC(=O)CCCc1ccc(N(CCCl)CCCl)cc1]

(E)-2-methoxy-5-(3-(5-methoxy-2,2-dimethyl-2H-chromen-8-yl)-3-oxoprop-1-en-1-yl)phenyl 4-(4-(bis(2-chloroethyl)amino)phenyl)butanoate (SKLBC-65)

The title compound was prepared from chlorambucil by a procedure similar to example 77, and the yield was 38.8%. $^1$H NMR (CDCl$_3$, 400 MHz) δ: 1.48 (s, 6H), 2.05 (quint, 2H), 2.62 (t, 2H), 2.69 (t, 2H), 3.62-3.65 (m, 4H), 3.70-3.74 (m, 4H), 3.87 (s, 3H), 3.89 (s, 3H), 5.61 (d, J=10.0 Hz, 1H), 6.51 (d, J=8.8 Hz, 1H), 6.66 (d, J=8.0 Hz, 2H), 6.69 (d, J=10.0 Hz, 1H), 6.98 (d, J=8.4 Hz, 1H), 7.12 (d, J=8.80 Hz, 2H), 7.27 (s, 1H), 7.44 (d, J=8.4 Hz, 1H), 7.59 (m, 2H), 7.70 (d, J=8.8 Hz, 1H) MS(ES+): m/z=652.33.

EXAMPLE 81

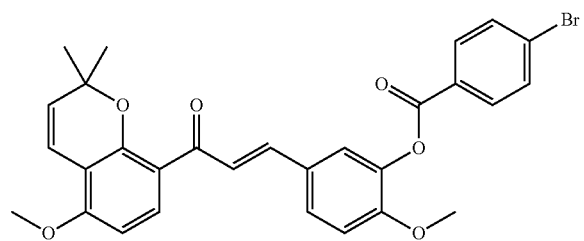 [SMILES: COc1ccc(/C=C/C(=O)c2ccc(OC)c3c2OC(C)(C)C=C3)cc1OC(=O)c1ccc(Br)cc1]

(E)-2-methoxy-5-(3-(5-methoxy-2,2-dimethyl-2H-chromen-8-yl)-3-oxoprop-1-en-1-yl)phenyl 4-bromobenzoate (SKLBC-66)

The title compound was prepared from p-bromobenzoic acid by a procedure similar to example 77, and the yield was 63.6%. $^1$H NMR (CDCl$_3$, 400 MHz) δ: 1.49 (s, 6H), 3.86 (s, 6H), 5.61 (d, J=10.0 Hz, 1H), 6.51 (d, J=8.4 Hz, 1H), 6.67 (d, J=10.0 Hz, 1H), 7.02 (d, J=8.4 Hz, 1H), 7.41 (s, 2H), 7.50 (d, J=8.4 Hz, 1H), 7.59-7.63 (m, 2H), 7.66 (d, J=8.4 Hz, 2H), 7.70 (d, J=8.4 Hz, 1H), 8.08 (d, J=8.4 Hz, 2H) MS(ES+): m/z=549.05.

EXAMPLE 82

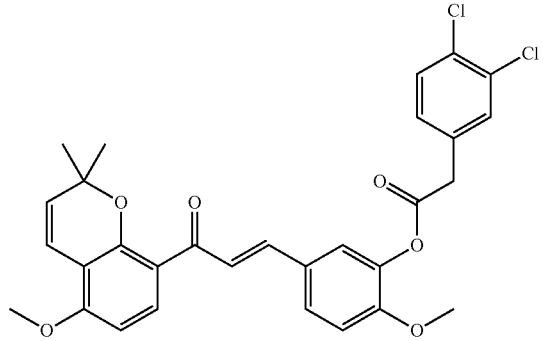 [SMILES: COc1ccc(/C=C/C(=O)c2ccc(OC)c3c2OC(C)(C)C=C3)cc1OC(=O)Cc1ccc(Cl)c(Cl)c1]

(E)-2-methoxy-5-(3-(5-methoxy-2,2-dimethyl-2H-chromen-8-yl)-3-oxoprop-1-en-1-yl)phenyl 2-(3,4-dichlorophenyl)acetate (SKLBC-67)

The title compound was prepared from 2-(3,4-dichlorophenyl)acetic acid by a procedure similar to example 77, and the yield was 70.1%. $^1$H NMR (CDCl$_3$, 400 MHz) δ: 1.45 (s, 6H), 3.83 (s, 3H), 3.86 (s, 2H), 3.88 (s, 3H), 5.62 (d, J=10.0 Hz, 1H), 6.50 (d, J=8.4 Hz, 1H), 6.68 (d, J=10.0 Hz, 1H), 6.96 (d, J=8.4 Hz, 1H), 7.24 (d, 1H), 7.26 (d, 1H), 7.43 (d, J=8.0 Hz, 2H), 7.54-7.58 (m, 3H), 7.70 (d, J=8.8 Hz, 1H) MS(ES+): m/z=553.06.

EXAMPLE 83

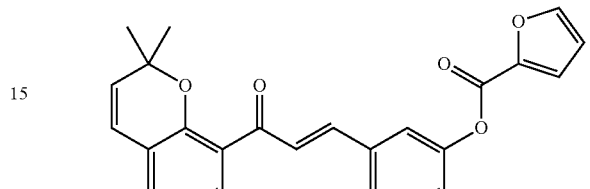

(E)-2-methoxy-5-(3-(5-methoxy-2,2-dimethyl-2H-chromen-8-yl)-3-oxoprop-1-en-1-yl)phenyl furan-2-carboxylate (SKLBC-68)

The title compound was prepared from pyromucic acid by a procedure similar to example 77, and the yield was 87.5%. $^1$H NMR (CDCl$_3$, 400 MHz) δ: 1.49 (s, 6H), 3.86 (s, 6H), 5.61 (d, J=10.0 Hz, 1H), 6.50 (d, J=8.4 Hz, 1H), 6.60-6.64 (m, 1H), 6.67 (d, J=10.0 Hz, 1H), 7.01 (d, J=8.4 Hz, 2H), 7.41 (m, 2H), 7.48 (d, J=8.4 Hz, 1H), 7.56 (d, J=15.6 Hz, 1H), 7.61 (d, J=15.6 Hz, 1H), 7.68 (m, 1H), 7.70 (d, J=8.8 Hz, 1H) MS(ES+): m/z=461.13.

EXAMPLE 84

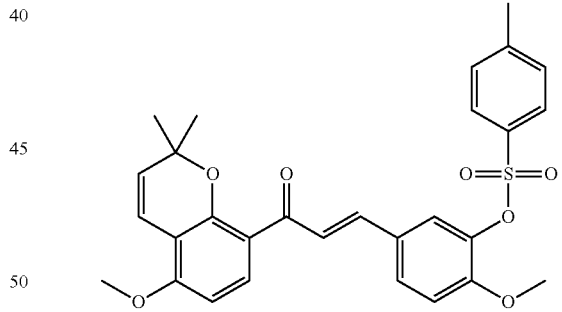

(E)-2-methoxy-5-(3-(5-methoxy-2,2-dimethyl-2H-chromen-8-yl)-3-oxoprop-1-en-1-yl)phenyl 4-methylbenzenesulfonate (SKLBC-69)

SKLBC-29 (184 mg, 0.5 mmol) was dissolved in 7 mL DCM. p-toluene sulfonyl chloride (172.20 L, 1.25 mmol) and triethylamine (140 L, 1 mmol) were added to the reaction. Then the reaction was stirred at room temperature for 12 h. When the reaction was completed, the reaction was poured into 30 mL H$_2$O, extracted by ethyl acetate, dried by Na$_2$SO$_4$, concentrated by reduce pressure, and purified by chromatography by silicon gel to give the target compound 204 mg, 78.5%. $^1$H NMR (CDCl$_3$, 400 MHz) δ: 1.52 (s, 6H) 2.35s, 3H), 3.60 (s, 3H), 3.89 (s, 3H), 5.63 (d, J=10 Hz, 1H), 6.51 (d, J=8.8 Hz, 1H), 6.68 (d, J=10.0 Hz, 1H), 6.83 (d, J=8.4 Hz, 1H), 7.29 (d, J=8.0 Hz, 1H), 7.38 (dd, J=8.8 Hz, 2.0 Hz, 1H), 7.44 (d, J=2.0 Hz, 1H), 7.53 (d, J=2.0 Hz, 1H), 7.53 (d, J=16.0 Hz, 1H), 7.58 (d, J=15.6 Hz, 1H), 7.71 (d, J=8.8 Hz, 1H), 7.74 (d, J=8.4 Hz, 1H) MS(ES+): m/z=521.19.

EXAMPLE 85

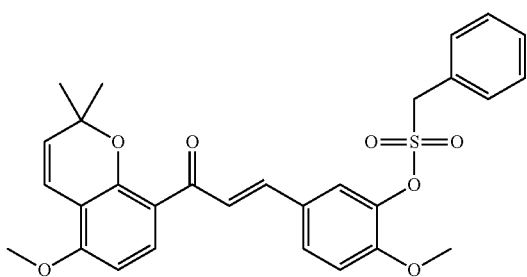 [SMILES: COc1ccc(/C=C/C(=O)c2ccc(OC)c3c2OC(C)(C)C=C3)cc1OS(=O)(=O)Cc1ccccc1]

(E)-2-methoxy-5-(3-(5-methoxy-2,2-dimethyl-2H-chromen-8-yl)-3-oxoprop-1-en-1-yl)phenyl phenyl-methanesulfonate (SKLBC-70)

The title compound was prepared from phenylmethanesulfonyl chloride by a procedure similar to example 84, and the yield was 81.2%. $^1$H NMR (CDCl$_3$, 400 MHz) δ:1.51 (s, 6H), 3.88 (s, 3H), 3.93 (s, 3H), 4.59 (s, 2H), 5.61 (d, J=10.0 Hz, 1H), 6.51 (d, J=8.8 Hz, 1H), 6.67 (d, J=10.0 Hz, 1H), 6.99 (d, J=8.4 Hz, 1H), 7.26-7.49 (m, 1H), 7.36-7.49 (m, 6H), 7.52 (d, J=15.6 Hz, 1H), 7.57 (d, J=15.6 Hz, 1H), 7.70 (d, J=8.8 Hz, 1H) MS (ES+): m/z=521.14.

EXAMPLE 86

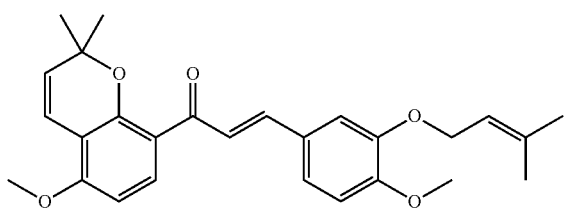 [SMILES: COc1ccc(/C=C/C(=O)c2ccc(OC)c3c2OC(C)(C)C=C3)cc1OCC=C(C)C]

(E)-1-(5-methoxy-2,2-dimethyl-2H-chromen-8-yl)-3-(4-methoxy-3-((3-methylbut-2-en-1-yl)oxy)phenyl)prop-2-en-1-one (SKLBC-71)

To a solution of compound SKLBC-28 (0.365 g, 1 mmol) in anhydrous CH$_3$CN (10 mL) was added anhydrous K$_2$CO$_3$ (0.345 g, 2.5 mmol, 2.5 equiv). After stirred over 15 min at room temperature, 1-bromo-3-methylbut-2-ene (2 mmol, 2 equiv) was added into the slurry. The reaction mixture was stirred at room temperature for 6 h. The reaction mixture was filtered, diluted with EtOAc and subsequently washed with water, then brine. The organic layer was dried over sodium sulfate and concentrated in vacuo. The resulting residue was purified by flash chromatography using petroleum ether/ethyl acetate (4:1) as eluent to yield light yellow solids 60.0%. $^1$H NMR (CDCl$_3$, 400 MHz) δ: 1.50 (s, 3H), 1.61 (s, 3H), 1.74 (m, 6H), 3.87 (s, 3H), 3.89 (s, 3H), 4.59 (d, J=6.4 Hz, 2H), 5.53 (m, 1H), 5.62 (d, J=10.0 Hz, 1H), 6.50 (d, J=8.8 Hz, 1H), 6.68 (d, J=9.6 Hz, 1H), 6.85-6.88 (m, 1H), 7.14-7.17 (m, 2H), 7.56 (d, J=16.0 Hz, 1H), 7.62 (d, J=16.0 Hz, 1H), 7.70 (d, J=8.8 Hz, 1H) MS(ES+): m/z=435.27.

EXAMPLE 87

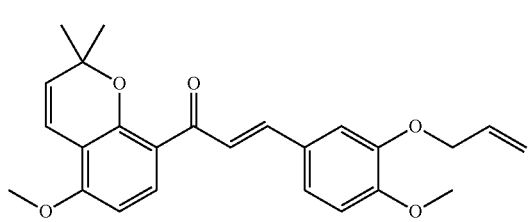 [SMILES: C=CCOc1cc(/C=C/C(=O)c2ccc(OC)c3c2OC(C)(C)C=C3)ccc1OC]

(E)-3-(3-(allyloxy)-4-methoxyphenyl)-1-(5-methoxy-2,2-dimethyl-2H-chromen-8-yl)prop-2-en-1-one (SKLBC-72)

The title compound was prepared from 3-bromoprop-1-ene by a procedure similar to example 86, and the yield was 61.3%. $^1$H NMR (CDCl$_3$, 400 MHz) δ: 1.50 (s, 6H), 3.88 (s, 3H), 3.91 (s, 3H), 4.63 (d, J=4.0 Hz, 2H), 5.28 (dd, J=9.2 Hz, 1.6 Hz, 1H), 5.38 (dd, J=17.2 Hz, 1.6 Hz, 1H), 5.61 (d, J=10.0 Hz, 1H), 6.04-6.12 (m, 1H), 6.50 (d, J=8.4 Hz, 1H), 6.68 (d, J=10.0 Hz, 1H), 6.89 (d, J=8.4 Hz, 1H), 7.14 (d, J=2.0 Hz, 1H), 7.19 (dd, J=8.40 Hz, 1.6 Hz, 1H), 7.54 (d, J=15.6 Hz, 1H), 7.60 (d, J=15.6 Hz, 1H) 7.71 (d, J=8.4 Hz, 1H) MS(ES+): m/z=407.21.

EXAMPLE 88

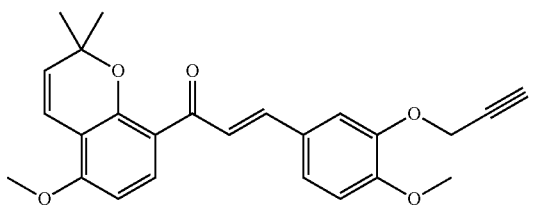 [SMILES: C#CCOc1cc(/C=C/C(=O)c2ccc(OC)c3c2OC(C)(C)C=C3)ccc1OC]

(E)-1-(5-methoxy-2,2-dimethyl-2H-chromen-8-yl)-3-(4-methoxy-3-(prop-2-yn-1-yloxy)phenyl)prop-2-en-1-one (SKLBC-73)

The title compound was prepared from 3-bromoprop-1-yne by a procedure similar to example 86, and the yield was 47.3%. $^1$H NMR (CDCl$_3$, 400 MHz) δ: 1.52 (s, 6H), 2.52 (s, 1H), 3.89 (s, 3H), 3.92 (s, 3H), 4.80 (s, 2H), 5.63 (d, J=10.0 Hz, 1H), 6.51 (d, J=8.4 Hz, 1H), 6.69 (d, J=10.0 Hz, 1H), 6.91 (d, J=8.0 Hz, 1H), 7.23-7.31 (m, 2H), 7.58 (d, J=15.6 Hz, 1H), 7.65 (d, J=15.6 Hz, 1H), 7.71 (d, J=8.4 Hz, 1H) MS(ES+): m/z=405.17.

EXAMPLE 89

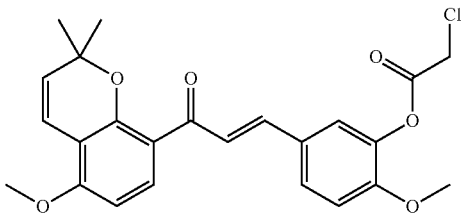 [SMILES: COc1ccc(/C=C/C(=O)c2ccc(OC)c3c2OC(C)(C)C=C3)cc1OC(=O)CCl]

(E)-2-methoxy-5-(3-(5-methoxy-2,2-dimethyl-2H-chromen-8-yl)-3-oxoprop-1-en-1-yl)phenyl 2-chloroacetate (SKLBC-74)

The title compound was prepared from 2-chloroacetic acid by a procedure similar to example 77, and the yield was 72.7%. $^1$H NMR (CDCl$_3$, 400 MHz) δ: 1.49 (s, 6H), 3.88 (s, 6H), 4.35 (s, 2H), 5.62 (d, J=10.0 Hz, 1H), 6.50 (d, J=8.8 Hz, 1H), 6.68 (d, J=10.0 Hz, 1H), 6.99 (d, J=8.4 Hz, 2H), 7.33 (d, J=2.0 Hz, 1H), 7.46 (dd, J=8.4 Hz, 1.6 Hz, 1H), 7.59 (m, 2H), 7.70 (d, J=8.8 Hz, 1H), MS(ES+): m/z=443.08.

EXAMPLE 90

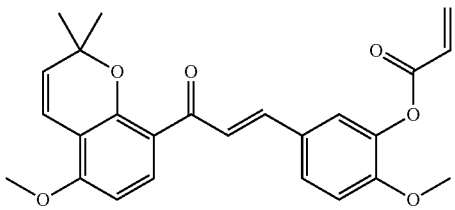 [SMILES: C=CC(=O)Oc1cc(/C=C/C(=O)c2ccc(OC)c3c2OC(C)(C)C=C3)ccc1OC]

(E)-2-methoxy-5-(3-(5-methoxy-2,2-dimethyl-2H-chromen-8-yl)-3-oxoprop-1-en-1-yl)phenyl acrylate (SKLBC-75)

The title compound was prepared from acrylic acid by a procedure similar to example 77, and the yield was 42.8%. $^1$H NMR (CDCl$_3$, 400 MHz) δ: 1.49 (s, 6H), 3.88 (s, 6H), 5.62 (d, J=10.0 Hz, 1H), 6.02 (d, J=10.4 Hz, 1H), 6.36 (dd, J=17.2 Hz, 10.4 Hz, 1H), 6.50 (d, J=8.4 Hz, 1H), 6.62 (d, J=17.2 Hz, 1H), 6.68 (d, J=10.0 Hz, 1H), 6.98 (d, J=8.8 Hz, 1H), 7.32 (d, J=2.0 Hz, 1H), 7.46 (dd, J=8.4 Hz, 2.0 Hz, 1H), 7.59 (q, 2H), 7.70 (d, J=8.8 Hz, 1H) MS(ES+): m/z=421.17.

EXAMPLE 91

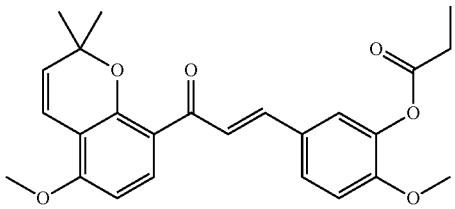 [SMILES: CCC(=O)Oc1cc(/C=C/C(=O)c2ccc(OC)c3c2OC(C)(C)C=C3)ccc1OC]

(E)-2-methoxy-5-(3-(5-methoxy-2,2-dimethyl-2H-chromen-8-yl)-3-oxoprop-1-en-1-yl)phenyl propionate (SKLBC-76)

The title compound was prepared from propanoic anhydride and SKLBC-28 by a procedure similar to example 60, and the yield was 72.0%. $^1$H NMR (CDCl$_3$, 400 MHz) δ: 1.29 (t, J=6.4 Hz, 3H), 1.49 (s, 6H), 2.61 (q, J=7.6 Hz, 2H), 3.87 (s, 6H), 5.62 (d, J=10.0 Hz, 1H), 6.51 (d, J=8.4 Hz, 1H), 6.68 (d, J=10.0 Hz, 1H), 6.97 (d, J=8.4 Hz, 1H), 7.29 (d, J=2.0 Hz, 1H), 7.43 (dd, J=8.4 Hz, 2.0 Hz, 1H), 7.55 (d, J=15.6 Hz, 1H), 7.60 (d, J=15.6 Hz, 1H), 7.70 (d, J=8.4 Hz, 1H). MS(ES+): m/z=423.18.

EXAMPLE 92

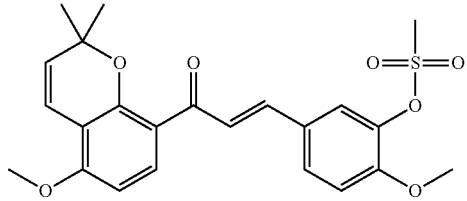 [SMILES: COc1ccc(/C=C/C(=O)c2ccc(OC)c3c2OC(C)(C)C=C3)cc1OS(C)(=O)=O]

(E)-2-methoxy-5-(3-(5-methoxy-2,2-dimethyl-2H-chromen-8-yl)-3-oxoprop-1-en-1-yl)phenyl methanesulfonate (SKLBC-77)

The title compound was prepared from methane sulfonyl chloride by a procedure similar to example 84, and the yield was 77.5%. $^1$H NMR (CDCl$_3$, 400 MHz) δ: 1.52 (s, 6H), 3.89 (s, 3H), 3.94 (s, 3H), 5.63 (d, J=10.4 Hz, 1H), 6.52 (d, J=8.8 Hz, 1H), 6.68 (d, J=10.0 Hz, 1H), 7.01 (d, J=8.8 Hz, 1H), 7.46 (dd, J=8.8 Hz, 2.0 Hz, 1H), 7.59 (d, J=15.6 Hz, 1H), 7.61 (d, J=2.0 Hz, 1H), 7.65 (d, J=15.6 Hz, 1H), 7.72 (d, J=8.8 Hz, 1H). MS(ES+): m/z=445.10.

EXAMPLE 93

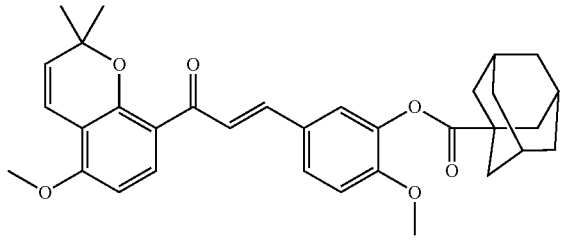 [SMILES: COc1ccc(/C=C/C(=O)c2ccc(OC)c3c2OC(C)(C)C=C3)cc1OC(=O)C12CC3CC(CC(C3)C1)C2]

The title compound was prepared from (1r,3r,5r,7r)-adamantane-2-carboxylic acid by a procedure similar to example 77, and the yield was 50.7%. $^1$H NMR (CDCl$_3$, 400 MHz) δ: 1.49 (s, 6H), 1.57 (m, 6H), 2.08 (m, 9H), 3.84 (s, 3H), 3.88 (s, 3H), 5.62 (d, J=10.0 Hz, 1H), 6.50 (d, J=8.8 Hz, 1H), 6.67 (d, J=10.0 Hz, 1H), 6.94 (d, J=8.8 Hz, 1H), 7.40 (d, J=7.6 Hz, 1H), 7.52-7.60 (m, 2H), 7.69 (d, J=8.8 Hz, 1H). MS(ES+): m/z=529.26.

EXAMPLE 94

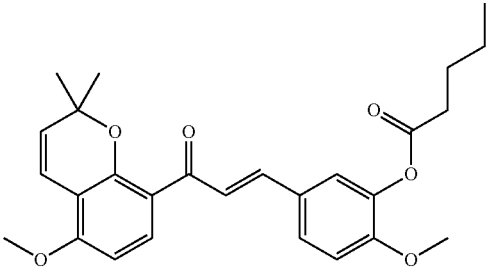 [SMILES: CCCCC(=O)Oc1cc(/C=C/C(=O)c2ccc(OC)c3c2OC(C)(C)C=C3)ccc1OC]

(E)-2-methoxy-5-(3-(5-methoxy-2,2-dimethyl-2H-chromen-8-yl)-3-oxoprop-1-en-1-yl)phenyl pentanoate (SKLBC-79)

The title compound was prepared from valeric anhydride and SKLBC-28 by a procedure similar to example 60, and the yield was 65.3%. ¹H NMR (CDCl₃, 400 MHz) δ: 0.97 (t, J=7.2 Hz, 3H), 1.43-1.47 (m, 2H), 1.48 (s, 6H), 1.76 (quint, J=7.6 Hz, 2H), 2.59 (t, J=7.2 Hz, 2H), 3.86 (s, 3H), 3.88 (s, 3H), 5.61 (d, J=10.0 Hz, 1H), 6.50 (d, J=8.8 Hz, 1H), 6.67 (d, J=10.0 Hz, 1H), 6.96 (d, J=8.4 Hz, 1H), 7.25 (d, J=2.0 Hz, 1H), 7.42 (dd, J=8.4 Hz, 2.0 Hz, 1H), 7.59 (m, 2H), 7.69 (d, J=8.8 Hz, 1H) MS(ES+): m/z=451.24.

EXAMPLE 95

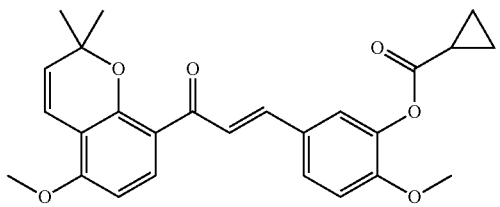 [SMILES: COc1ccc(/C=C/C(=O)c2ccc(OC)c3c2OC(C)(C)C=C3)cc1OC(=O)C1CC1]

(E)-2-methoxy-5-(3-(5-methoxy-2,2-dimethyl-2H-chromen-8-yl)-3-oxoprop-1-en-1-yl)phenyl cyclopropanecarboxylate (SKLBC-80)

The title compound was prepared from cyclopropanecarbonyl chloride by a procedure similar to example 84, and the yield was 66.6%. ¹H NMR (CDCl₃, 400 MHz) δ: 1.02-1.06 (m, 2H), 1.17-1.20 (m, 2H), 1.49 (s, 6H), 1.89 (m, 1H), 3.87 (s, 6H), 5.62 (d, J=10.0 Hz, 1H), 6.50 (d, J=8.8 Hz, 1H), 6.68 (d, J=10.0 Hz, 1H), 6.96 (d, J=8.4 Hz, 1H), 7.31 (d, J=2.0 Hz, 1H), 7.42 (dd, J=8.4 Hz, 2.0 Hz, 1H), 7.58 (m, 2H), 7.69 (d, J=8.8 Hz, 1H). MS(ES+): m/z=435.14

EXAMPLE 96

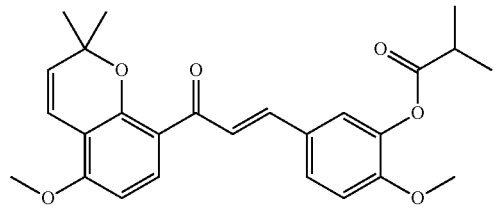 [SMILES: COc1ccc(/C=C/C(=O)c2ccc(OC)c3c2OC(C)(C)C=C3)cc1OC(=O)C(C)C]

(E)-2-methoxy-5-(3-(5-methoxy-2,2-dimethyl-2H-chromen-8-yl)-3-oxoprop-1-en-1-yl)phenyl isobutyrate (SKLBC-81)

The title compound was prepared from isobutyric anhydride and SKLBC-28 by a procedure similar to example 60, and the yield was 70.2%. ¹H NMR (CDCl₃, 400 MHz) δ: 1.32 (s, 3H), 1.34 (s, 3H), 1.49 (s, 6H), 2.85 (quint, J=7.6 Hz, 1H), 3.86 (s, 6H), 5.62 (d, J=10.0 Hz, 1H), 6.50 (d, J=8.8 Hz, 1H), 6.68 (d, J=10.0 Hz, 1H), 6.96 (d, J=8.4 Hz, 2H), 7.26 (s, 1H), 7.41 (d, J=8.8 Hz, 1H), 7.60 (m, 2H), 7.70 (d, J=8.8 Hz, 1H) MS (ES+): m/z=437.22.

EXAMPLE 97

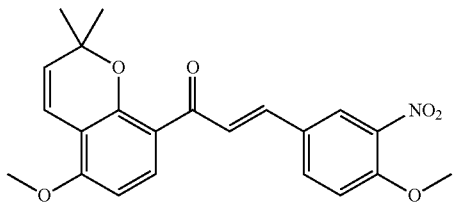

(E)-1-(5-methoxy-2,2-dimethyl-2H-chromen-8-yl)-3-(4-methoxy-3-nitrophenyl)prop-2-en-1-one (SKLBC-82)

The title compound was prepared from 4-methoxy-3-nitrobenzaldehyde by a procedure similar to example 2, and the yield was 70.6%. ¹H NMR (400 MHz, DMSO) δ: 8.25 (d, J=1.6 Hz, 1H), 8.01 (dd, J=8.8, 1.7 Hz, 1H), 7.63 (d, J=15.8 Hz, 1H), 7.56 (dd, J=12.2, 10.2 Hz, 2H), 7.47 (d, J=8.8 Hz, 1H), 6.71 (d, J=8.9 Hz, 1H), 6.62 (d, J=10.1 Hz, 1H), 5.79 (d, J=10.0 Hz, 1H), 3.98 (s, 3H), 3.87 (s, 3H), 1.45 (s, 6H).

EXAMPLE 98

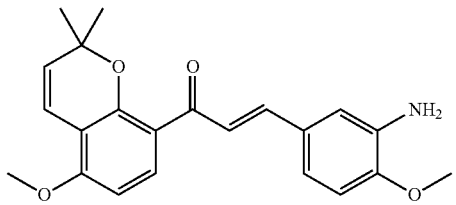

(E)-3-(3-amino-4-methoxyphenyl)-1-(5-methoxy-2,2-dimethyl-2H-chromen-8-yl)prop-2-en-1-one (SKLBC-83)

SKLBC-82 (792 mg, 2 mmol) in EtOH (10 mL) and water (3 mL) was added iron powder (335 mg, 6.7 mmol) and NH₄Cl (64 mg, 1.2 mmol). The reaction was stirred at 85° C. for 1 h, cooled to room temperature and filtered through Celite. The filter cake was washed with dichloromethane (20 mL) and the filtrate was concentrated under pressure. The residue was dissolved in dichloromethane (15 mL), washed with water (5 mL), dried over Na₂SO₄, filtered and concentrated. The residue was purified by flash column chromatography to give the title compound SKLBC-83 (540 mg, 74%). ¹H NMR (400 MHz, CDCl₃) δ 7.68 (d, J=8.8 Hz, 1H), 7.59 (d, J=15.7 Hz, 1H), 7.52 (d, J=15.7 Hz, 1H), 7.01 (d, J=8.4 Hz, 1H), 6.97 (s, 1H), 6.79 (d, J=8.2 Hz, 1H), 6.69 (d, J=10.0 Hz, 1H), 6.50 (d, J=8.8 Hz, 1H), 5.62 (d, J=10.0 Hz, 1H), 3.88 (s, 3H), 3.87 (s, 3H), 1.49 (d, J=5.2 Hz, 7H). MS (ES+): m/z=366.24

EXAMPLE 99

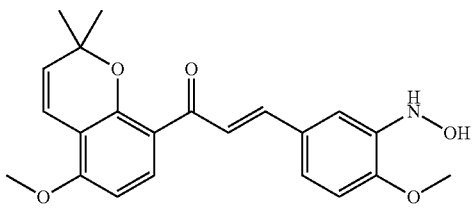 [SMILES: COc1ccc(/C=C/C(=O)c2ccc(OC)c3c2OC(C)(C)C=C3)cc1NO]

(E)-3-(3-(hydroxyamino)-4-methoxyphenyl)-1-(5-methoxy-2,2-dimethyl-2H-chromen-8-yl)prop-2-en-1-one (SKLBC-84)

A solution of SKLBC-82 (0.437 g, 1.10 mmol) in 11 mL THF was cooled in ice-water, sequentially AcOH (1.72 mL, 22.1 mmol) and Zn (2.90 g, 44.2 mmol) were added into the reaction. The reaction was stirred at room temperature for 30 min. Then the solvent was diluted with 30 mL ethyl acetate, and filtered by celit. The filtration was washed by saturate $NaHCO_3$ aqouse, brine, dried over $Na_2SO_4$, filtered and concentrated. The residue was purified by flash column chromatography to give the title compound. $^1$H NMR (400 MHz, $CDCl_3$) δ: 8.43 (s, 1H), 7.91 (s, 1H), 7.63-7.57 (m, 2H), 7.51 (d, J=15.7 Hz, 1H), 7.42 (s, 1H), 7.08 (d, J=8.0 Hz, 1H), 6.92 (d, J=8.2 Hz, 1H), 6.72 (d, J=8.9 Hz, 1H), 6.63 (d, J=10.0 Hz, 1H), 5.80 (d, J=10.0 Hz, 1H), 3.87 (s, 3H), 3.82 (s, 3H), 1.49 (s, 6H). MS(ES+): m/z=382.20.

EXAMPLE 100

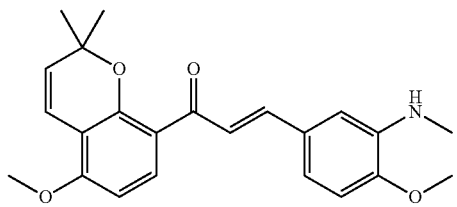

(E)-1-(5-methoxy-2,2-dimethyl-2H-chromen-8-yl)-3-(4-methoxy-3-(methylamino)phenyl)prop-2-en-1-one (SKLBC-85)

To a solution of compound SKLBC-83 (365 mg, 1 mmol) in anhydrous $CH_3CN$ (10 mL) was added anhydrous $K_2CO_3$ (0.345 g, 2.5 mmol). After stirred over 15 min at room temperature, $CH_3I$ (2 equiv) was added into the slurry. The reaction mixture was stirred at reflux for 6 hours. The reaction mixture was filtrate and diluted with EtOAc, then washed by water and brine, dried over anhydrous $Na_2SO_4$ and concentrated in vacuo. The residue was purified by flash chromatograph using petroleum ether/ethyl acetate (5:1) as eluent to give the title compounds, 23%. $^1$H NMR (400 MHz, $CDCl_3$) δ 7.72 (d, J=8.8 Hz, 1H), 7.70-7.59 (m, 2H), 6.93 (d, J=8.1 Hz, 1H), 6.87 (d, J=6.0 Hz, 1H), 6.76 (d, J=7.9 Hz, 1H), 6.70 (d, J=10.0 Hz, 1H), 6.52 (d, J=8.8 Hz, 1H), 5.63 (d, J=10.0 Hz, 1H), 3.88 (s, 6H), 2.90 (s, 3H), 1.52 (s, 6H). MS(ES+): m/z=380.21.

EXAMPLE 101

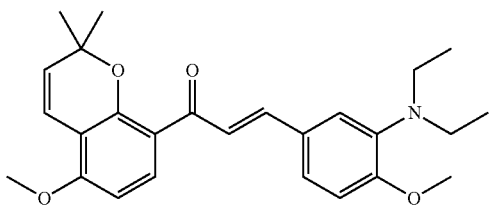 [SMILES: CCN(CC)c1cc(/C=C/C(=O)c2ccc(OC)c3c2OC(C)(C)C=C3)ccc1OC]

(E)-3-(3-(diethylamino)-4-methoxyphenyl)-1-(5-methoxy-2,2-dimethyl-2H-chromen-8-yl)prop-2-en-1-one (SKLBC-86)

The title compound was prepared from $CH_3CH_2I$ by a procedure similar to example 100, and the yield was 84%. $^1$H NMR (400 MHz, $CDCl_3$) δ: 7.71 (d, J=8.8 Hz, 1H), 7.69-7.56 (m, 2H), 7.24 (d, J=7.3 Hz, 1H), 6.90 (dd, J=19.7, 6.8 Hz, 2H), 6.76 (d, J=8.1 Hz, 1H), 6.70 (d, J=10.0 Hz, 1H), 6.52 (d, J=8.8 Hz, 1H), 5.63 (d, J=10.0 Hz, 1H), 3.89 (d, J=7.2 Hz, 6H), 3.19 (p, J=6.7 Hz, 3H), 1.51 (s, 6H), 1.31 (t, J=7.1 Hz, 2H), 1.04 (t, J=7.0 Hz, 3H)

EXAMPLE 102

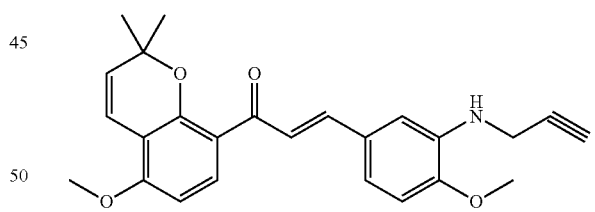

(E)-1-(5-methoxy-2,2-dimethyl-2H-chromen-8-yl)-3-(4-methoxy-3-(prop-2-yn-1-ylamino)phenyl)prop-2-en-1-one (SKLBC-87)

The title compound was prepared from 3-bromoprop-1-yne by a procedure similar to example 100, and the yield was 72%. $^1$H NMR (400 MHz, $CDCl_3$) δ: 7.71 (d, J=9.0 Hz, 1H), 7.62 (t, J=15.1 Hz, 2H), 7.07-6.97 (m, 2H), 6.81 (d, J=8.1 Hz, 1H), 6.70 (d, J=10.0 Hz, 1H), 6.52 (d, J=8.8 Hz, 1H), 5.62 (t, J=10.6 Hz, 1H), 4.01 (s, 2H), 3.89 (d, J=3.4 Hz, 6H), 2.22 (s, 1H), 1.53 (s, 6H). MS(ES+): m/z=404.29.

EXAMPLE 103

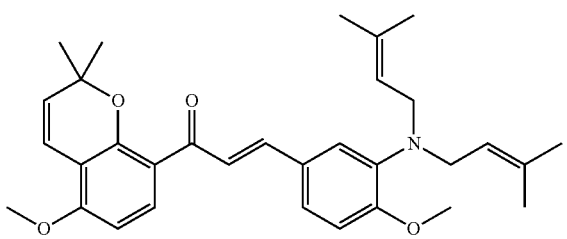 [SMILES: COc1ccc(/C=C/C(=O)c2ccc(OC)c3c2OC(C)(C)C=C3)cc1N(CC=C(C)C)CC=C(C)C]

(E)-3-(3-(bis(3-methylbut-2-en-1-yl)amino)-4-methoxyphenyl)-1-(5-methoxy-2,2-dimethyl-2H-chromen-8-yl)prop-2-en-1-one (SKLBC-88)

The title compound was prepared from 1-bromo-3-methylbut-2-ene by a procedure similar to example 100, and the yield was 61%. $^1$H NMR (400 MHz, CDCl$_3$) δ: 7.72 (d, J=8.7 Hz, 2H), 7.66 (d, J=15.8 Hz, 1H), 7.59 (d, J=15.6 Hz, 1H), 7.23 (d, J=8.2 Hz, 1H), 7.17 (s, 1H), 6.86 (d, J=8.2 Hz, 1H), 6.70 (d, J=10.0 Hz, 1H), 6.52 (d, J=8.8 Hz, 1H), 5.63 (d, J=10.0 Hz, 1H), 5.20 (s, 2H), 4.31 (t, J=6.7 Hz, 1H), 3.91 (s, 3H), 3.88 (s, 3H), 3.72 (d, J=5.9 Hz, 5H), 1.68 (s, 6H), 1.60 (s, 6H), 1.52 (s, 6H), 0.97 (dd, J=14.8, 7.1 Hz, 2H). MS(ES+): m/z=502.39.

EXAMPLE 104

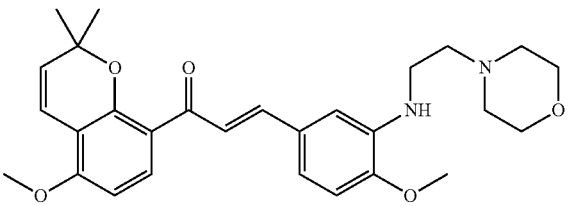 [SMILES: COc1ccc(/C=C/C(=O)c2ccc(OC)c3c2OC(C)(C)C=C3)cc1NCCN1CCOCC1]

(E)-1-(5-methoxy-2,2-dimethyl-2H-chromen-8-yl)-3-(4-methoxy-3-((2-morpholinoethyl)amino)phenyl)prop-2-en-1-one (SKLBC-89)

The title compound was prepared from 4-(2-chloroethyl)morpholine by a procedure similar to example 100, and the yield was 81%. $^1$H NMR (400 MHz, CDCl$_3$) δ: 7.71 (d, J=8.8 Hz, 1H), 7.65 (d, J=15.7 Hz, 1H), 7.58 (d, J=15.7 Hz, 1H), 6.96 (d, J=7.9 Hz, 1H), 6.86 (s, 1H), 6.77 (d, J=8.2 Hz, 1H), 6.70 (d, J=10.0 Hz, 1H), 6.52 (d, J=8.8 Hz, 1H), 5.63 (d, J=10.0 Hz, 1H), 4.82 (s, 1H), 3.91 (s, 3H), 3.89 (s, 3H), 3.73 (s, 4H), 3.21 (s, 2H), 2.70 (s, 2H), 2.49 (s, 4H), 1.51 (s, 7H). MS(ES+): m/z=479.28.

EXAMPLE 105

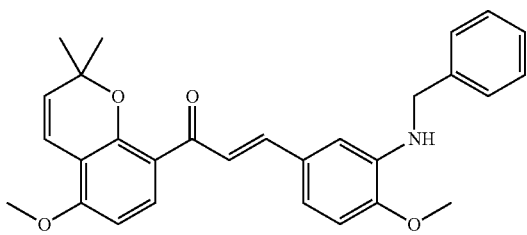 [SMILES: COc1ccc(/C=C/C(=O)c2ccc(OC)c3c2OC(C)(C)C=C3)cc1NCc1ccccc1]

(E)-3-(3-(benzylamino)-4-methoxyphenyl)-1-(5-methoxy-2,2-dimethyl-2H-chromen-8-yl)prop-2-en-1-one (SKLBC-90)

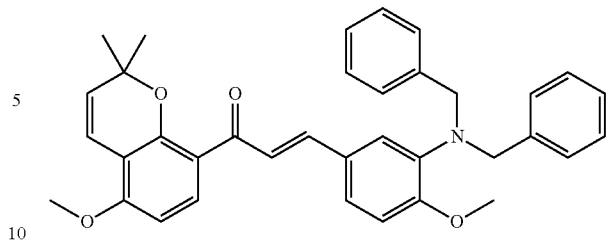

(E)-3-(3-(dibenzylamino)-4-methoxyphenyl)-1-(5-methoxy-2,2-dimethyl-2H-chromen-8-yl)prop-2-en-1-one (SKLBC-91)

The title compounds were prepared from BnBr by a procedure similar to example 100, and the yields were 23% (SKLBC-90) and 33% (SKLBC-91). SKLBC-90 $^1$H NMR (400 MHz, CDCl$_3$) δ 7.69 (d, J=8.8 Hz, 1H), 7.62 (d, J=15.7 Hz, 1H), 7.53 (d, J=15.7 Hz, 1H), 7.36 (q, J=8.0 Hz, 4H), 7.31-7.27 (m, 1H), 6.96 (dd, J=8.2, 1.7 Hz, 1H), 6.88 (d, J=1.7 Hz, 1H), 6.79 (d, J=8.2 Hz, 1H), 6.68 (d, J=10.0 Hz, 1H), 6.50 (d, J=8.8 Hz, 1H), 5.60 (d, J=10.0 Hz, 1H), 4.37 (s, 2H), 3.88 (d, J=5.5 Hz, 6H), 1.45 (s, 6H). MS(ES+): m/z=456.18. SKLBC-91 $^1$H NMR (400 MHz, CDCl$_3$) δ 7.67 (d, J=8.6 Hz, 1H), 7.54 (d, J=15.7 Hz, 1H), 7.45 (d, J=15.7 Hz, 1H), 7.36 (d, J=4.4 Hz, 1H), 7.28 (s, 2H), 7.27-7.16 (m, 9H), 7.06 (s, 1H), 6.91 (d, J=8.4 Hz, 1H), 6.68 (d, J=10.0 Hz, 1H), 6.49 (d, J=8.9 Hz, 1H), 5.61 (d, J=10.0 Hz, 1H), 4.25 (s, 3H), 3.96 (s, 3H), 3.87 (s, 4H), 1.43 (s, 6H). MS(ES+): m/z=546.36.

EXAMPLE 106

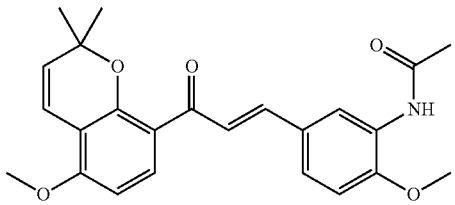 [SMILES: COc1ccc(/C=C/C(=O)c2ccc(OC)c3c2OC(C)(C)C=C3)cc1NC(C)=O]

(E)-N-(2-methoxy-5-(3-(5-methoxy-2,2-dimethyl-2H-chromen-8-yl)-3-oxoprop-1-en-1-yl)phenyl)acetamide (SKLBC-92)

Acetic acid (1.5 mmol) was added to a stirred mixture of SKLBC-83 (365 mg, 1 mmol), EDCI (288 mg, 1.5 mmol), DMAP (61 mg, 0.5 mmol) in anhydrous CH$_2$Cl$_2$ (5 mL). The mixture was stirred at room temperature for 12 h. On completion, the slurry was partitioned between water (20 mL) and CH$_2$Cl$_2$ (20 mL), and the water was extracted with CH$_2$Cl$_2$ (3×10 mL). The organic solvents were combined and removed under reduced pressure to yield a yellow solid. Chromatographic separation (petroleum ether-ethyl acetate, 5:1) gave the title compounds 75%. $^1$H NMR (400 MHz, CDCl$_3$) δ: 8.76 (s, 1H), 7.76 (s, 1H), 7.70 (d, J=8.8 Hz, 1H), 7.25 (d, J=12.1 Hz, 2H), 6.87 (d, J=8.4 Hz, 1H), 6.68 (d, J=10.0 Hz, 1H), 6.50 (d, J=8.8 Hz, 1H), 5.63 (d, J=10.0 Hz, 1H), 3.91 (s, 3H), 3.87 (s, 3H), 2.21 (s, 3H), 1.55 (s, 7H). MS(ES+): m/z=430.20.

EXAMPLE 107

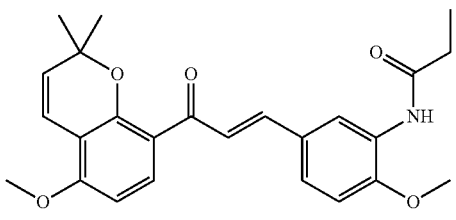

(E)-N-(2-methoxy-5-(3-(5-methoxy-2,2-dimethyl-2H-chromen-8-yl)-3-oxoprop-1-en-1-yl)phenyl)propionamide (SKLBC-93)

The title compound was prepared from propanoic acid by a procedure similar to example 106, and the yield was 56%. $^1$H NMR (400 MHz, CDCl$_3$) δ: 8.80 (s, 1H), 7.75 (s, 1H), 7.69 (d, J=8.8 Hz, 1H), 7.25 (d, J=9.9 Hz, 2H), 6.88 (d, J=8.4 Hz, 1H), 6.68 (d, J=10.0 Hz, 1H), 6.50 (d, J=8.8 Hz, 1H), 5.63 (d, J=10.0 Hz, 1H), 3.92 (s, 3H), 3.88 (s, 3H), 2.43 (q, J=7.5 Hz, 2H), 1.54 (s, 6H), 1.25 (t, J=7.4 Hz, 4H). MS(ES+): m/z=444.22.

EXAMPLE 108

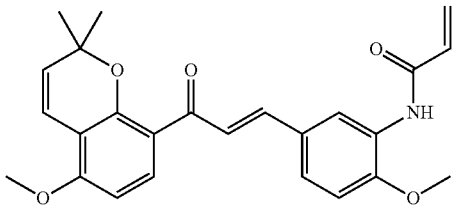 [SMILES: C=CC(=O)Nc1cc(/C=C/C(=O)c2ccc(OC)c3c2OC(C)(C)C=C3)ccc1OC]

(E)-N-(2-methoxy-5-(3-(5-methoxy-2,2-dimethyl-2H-chromen-8-yl)-3-oxoprop-1-en-1-yl)phenyl)acrylamide (SKLBC-94)

The title compound was prepared from acrylic acid by a procedure similar to example 106, and the yield was 71%. $^1$H NMR (400 MHz, CDCl$_3$) δ: 8.89 (s, 1H), 7.86 (s, 1H), 7.70 (d, J=8.8 Hz, 1H), 7.66 (s, 2H), 7.29 (d, J=8.8 Hz, 1H), 6.90 (d, J=8.5 Hz, 1H), 6.68 (d, J=10.0 Hz, 1H), 6.51 (d, J=8.8 Hz, 1H), 6.42 (d, J=16.8 Hz, 1H), 6.29 (dd, J=16.8, 10.1 Hz, 1H), 5.77 (d, J=10.1 Hz, 1H), 5.63 (d, J=10.0 Hz, 1H), 3.94 (s, 3H), 3.88 (s, 3H), 1.55 (s, 6H). MS(ES+): m/z=420.23.

EXAMPLE 109

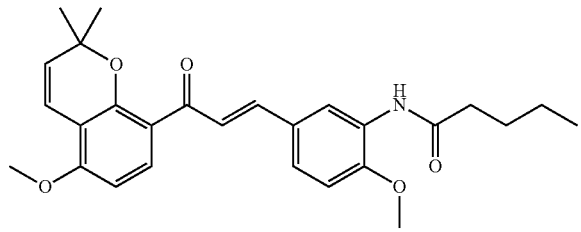 [SMILES: CCCCC(=O)Nc1cc(/C=C/C(=O)c2ccc(OC)c3c2OC(C)(C)C=C3)ccc1OC]

(E)-N-(2-methoxy-5-(3-(5-methoxy-2,2-dimethyl-2H-chromen-8-yl)-3-oxoprop-1-en-1-yl)phenyl)pentanamide (SKLBC-95)

The title compound was prepared from pentanoic acid by a procedure similar to example 106, and the yield was 67%. $^1$H NMR (400 MHz, CDCl$_3$) δ: 8.80 (s, 1H), 7.73 (s, 1H), 7.70 (d, J=8.8 Hz, 1H), 7.65 (s, 2H), 7.24 (s, 1H), 6.88 (d, J=8.4 Hz, 1H), 6.68 (d, J=10.0 Hz, 1H), 6.50 (d, J=8.8 Hz, 1H), 5.63 (d, J=10.0 Hz, 1H), 3.92 (s, 3H), 3.88 (s, 4H), 2.40 (t, J=7.5 Hz, 2H), 1.77-1.67 (m, 2H), 1.54 (s, 6H), 1.42 (dd, J=15.3, 7.7 Hz, 3H), 0.95 (t, J=7.3 Hz, 3H). MS(ES+): m/z=472.25.

EXAMPLE 110

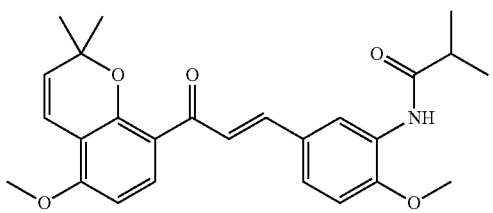 [SMILES: COc1ccc(/C=C/C(=O)c2ccc(OC)c3c2OC(C)(C)C=C3)cc1NC(=O)C(C)C]

(E)-N-(2-methoxy-5-(3-(5-methoxy-2,2-dimethyl-2H-chromen-8-yl)-3-oxoprop-1-en-1-yl)phenyl) isobutyramide (SKLBC-96)

The title compound was prepared from isobutyric acid by a procedure similar to example 106, and the yield was 63%. MS(ES+): m/z=458.19.

EXAMPLE 111

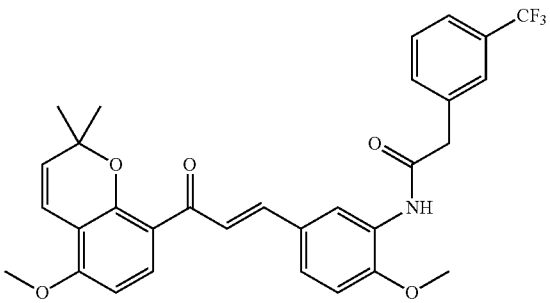 [SMILES: COc1ccc(/C=C/C(=O)c2ccc(OC)c3c2OC(C)(C)C=C3)cc1NC(=O)Cc1cccc(C(F)(F)F)c1]

(E)-N-(2-methoxy-5-(3-(5-methoxy-2,2-dimethyl-2H-chromen-8-yl)-3-oxoprop-1-en-1-yl)phenyl)-2-(3-(trifluoromethyl)phenyl)acetamide (SKLBC-97)

The title compound was prepared from 2-(3-(trifluoromethyl)phenyl)acetic acid by a procedure similar to example 106, and the yield was 74%. $^1$H NMR (400 MHz, CDCl$_3$) δ: 8.76 (s, 1H), 7.76 (s, 1H), 7.70 (d, J=8.8 Hz, 1H), 7.25 (d, J=12.1 Hz, 2H), 6.87 (d, J=8.4 Hz, 1H), 6.68 (d, J=10.0 Hz, 1H), 6.50 (d, J=8.8 Hz, 1H), 5.63 (d, J=10.0 Hz, 1H), 3.91 (s, 3H), 3.87 (s, 3H), 2.21 (s, 3H), 1.55 (s, 7H). MS(ES+): m/z=574.26.

EXAMPLE 112

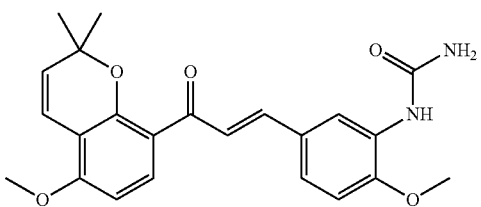 [SMILES: COc1ccc(/C=C/C(=O)c2ccc(OC)c3c2OC(C)(C)C=C3)cc1NC(N)=O]

(E)-1-(2-methoxy-5-(3-(5-methoxy-2,2-dimethyl-2H-chromen-8-yl)-3-oxoprop-1-en-1-yl)phenyl)urea (SKLBC-98)

SKLBC-83 (197 mg, 0.54 mmol) in AcOH (6.8 mL) was added KOCN (131 mg, 1.62 mmol) and water (0.54 mL) and stirred at room temperature overnight. When the reaction was finished, the solvent was removed under vacuum and the residue was purified by flash chromatograph using petroleum ether/ethyl acetate (3:1) as eluent to give the title compound (163 mg, 74% yield as a yellow solid). $^1$H NMR (400 MHz, CDCl$_3$) δ: 8.40 (s, 1H), 7.70 (d, J=8.9 Hz, 1H), 7.65 (s, 2H), 7.23 (d, J=8.6 Hz, 1H), 6.98 (s, 1H), 6.87 (d, J=8.4 Hz, 1H), 6.68 (d, J=10.0 Hz, 1H), 6.51 (d, J=8.8 Hz, 1H), 5.63 (d, J=10.0 Hz, 1H), 5.17-4.40 (m, 1H), 3.89 (d, J=3.6 Hz, 7H), 1.54 (s, 6H). MS(ES+): m/z=431.21.

EXAMPLE 113

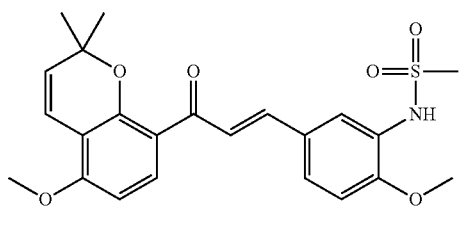

(E)-N-(2-methoxy-5-(3-(5-methoxy-2,2-dimethyl-2H-chromen-8-yl)-3-oxoprop-1-en-1-yl)phenyl)methanesulfonamide (SKLBC-99)

To SKLBC-83 (365 mg, 1 mmol) in CH$_2$Cl$_2$ (5 mL) was added MeSO$_2$Cl (2 equiv) and Et$_3$N (2 equiv) and stirred at room temperature for 6 h. When completed, the solvent was removed under vacuum and the residue was purified by flash chromatograph using petroleum ether/ethyl acetate (5:1) as eluent to give the title compounds (0.359 g, 81%). $^1$H NMR (400 MHz, CDCl$_3$) δ: 7.88 (s, 1H), 7.72 (d, J=9.0 Hz, 1H), 7.65 (t, J=10.5 Hz, 2H), 7.33 (d, J=8.3 Hz, 1H), 6.93 (d, J=8.4 Hz, 1H), 6.88 (s, 1H), 6.68 (d, J=10.0 Hz, 1H), 6.52 (d, J=8.9 Hz, 1H), 5.64 (d, J=10.0 Hz, 1H), 3.93 (s, 3H), 3.88 (s, 3H), 2.98 (s, 3H), 1.54 (s, 7H). MS(ES+): m/z=466.15.

EXAMPLE 114

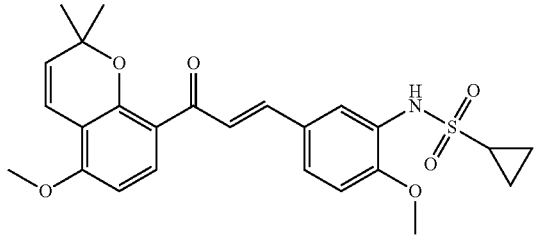 [SMILES: COc1ccc(/C=C/C(=O)c2ccc(OC)c3c2OC(C)(C)C=C3)cc1NS(=O)(=O)C1CC1]

(E)-N-(2-methoxy-5-(3-(5-methoxy-2,2-dimethyl-2H-chromen-8-yl)-3-oxoprop-1-en-1-yl)phenyl)cyclopropanesulfonamide (SKLBC-100)

The title compound was prepared from cyclopropanesulfonyl chloride by a procedure similar to example 113, and the yield was 84%. $^1$H NMR (400 MHz, CDCl$_3$) δ: 7.92 (s, 1H), 7.72 (d, J=8.9 Hz, 1H), 7.66 (d, J=3.6 Hz, 2H), 7.32 (d, J=8.2 Hz, 1H), 6.92 (d, J=8.4 Hz, 1H), 6.84 (s, 1H), 6.68 (d, J=10.0 Hz, 1H), 6.52 (d, J=8.9 Hz, 1H), 5.64 (d, J=10.0 Hz, 1H), 3.93 (s, 3H), 3.88 (s, 3H), 2.51-2.43 (m, 1H), 1.54 (s, 6H), 0.96-C0.82 (m, 4H). MS(ES+): m/z=470.18.

EXAMPLE 115

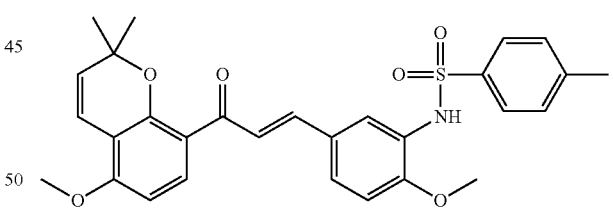

(E)-N-(2-methoxy-5-(3-(5-methoxy-2,2-dimethyl-2H-chromen-8-yl)-3-oxoprop-1-en-1-yl)phenyl)-4-methylbenzenesulfonamide (SKLBC-101)

The title compound was prepared from 4-methylbenzene-1-sulfonyl chloride by a procedure similar to example 113, and the yield was 88%. $^1$H NMR (400 MHz, CDCl$_3$) δ: 8.43 (s, 1H), 8.03 (d, J=8.3 Hz, 1H), 7.87 (d, J=8.4 Hz, 1H), 7.74 (d, J=15.9 Hz, 1H), 7.59 (t, J=11.0 Hz, 2H), 6.73 (d, J=8.9 Hz, 1H), 6.62 (d, J=10.0 Hz, 1H), 5.80 (d, J=10.0 Hz, 1H), 3.88 (s, 3H), 1.44 (s, 6H). MS(ES+): m/z=542.20.

EXAMPLE 116

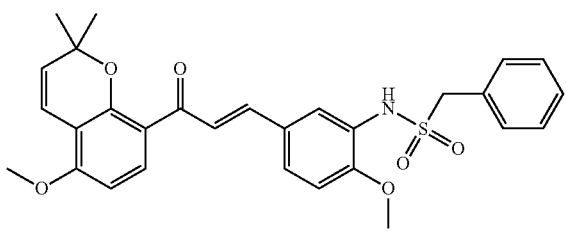 [SMILES: COc1ccc(/C=C/C(=O)c2ccc(OC)c3c2OC(C)(C)C=C3)cc1NS(=O)(=O)Cc1ccccc1]

(E)-N-(2-methoxy-5-(3-(5-methoxy-2,2-dimethyl-2H-chromen-8-yl)-3-oxoprop-1-en-1-yl)phenyl)-1-phenylmethanesulfonamide (SKLBC-102)

The title compound was prepared from phenylmethanesulfonyl chloride by a procedure similar to example 113, and the yield was 83%. $^1$H NMR (400 MHz, CDCl$_3$) δ: 7.90 (s, 1H), 7.74 (d, J=8.8 Hz, 1H), 7.71-7.59 (m, 2H), 7.31 (q, J=6.3 Hz, 4H), 7.18 (d, J=6.9 Hz, 2H), 6.89 (d, J=8.4 Hz, 1H), 6.76 (s, 1H), 6.70 (d, J=10.0 Hz, 1H), 6.53 (d, J=8.8 Hz, 1H), 5.65 (d, J=10.0 Hz, 1H), 4.33 (s, 2H), 3.90 (s, 3H), 3.81 (s, 3H), 1.56 (s, 7H). MS(ES+): m/z=542.27.

EXAMPLE 117

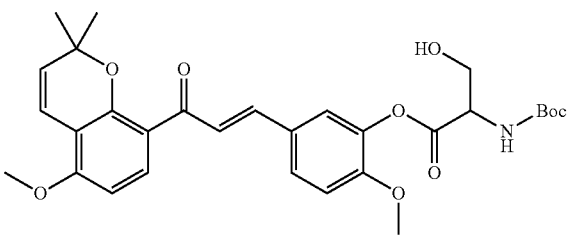 [SMILES: COc1ccc(/C=C/C(=O)c2ccc(OC)c3c2OC(C)(C)C=C3)cc1OC(=O)C(CO)NC(=O)OC(C)(C)C]

(E)-2-methoxy-5-(3-(5-methoxy-2,2-dimethyl-2H-chromen-8-yl)-3-oxoprop-1-en-1-yl)phenyl 2-((tert-butoxycarbonyl)amino)-3-hydroxypropanoate (SKLBC-103)

The title compound was prepared from 2-((tert-butoxycarbonyl)amino)-3-hydroxypropanoic acid by a procedure similar to example 77, and the yield was 67%. $^1$H NMR (400 MHz, CDCl$_3$) δ: 1.43-1.49 (m, 15H), 3.87 (s, 6H), 3.97 (m, 1H), 4.25 (s, 1H), 4.70 (s, 1H), 5.51 (m, 1H), 5.63 (d, J=10.0 Hz, 1H), 6.52 (d, J=8.8 Hz, 1H), 6.69 (d, J=10.0 Hz, 1H), 7.00 (d, J=8.4 Hz, 1H), 7.34 (d, J=8.4 Hz, 1H), 7.47 (dd, J=8.4, 2.0 Hz, 1H), 7.58-7.60 (m, 2H), 7.70 (d, J=8.8 Hz, 1H)

EXAMPLE 118

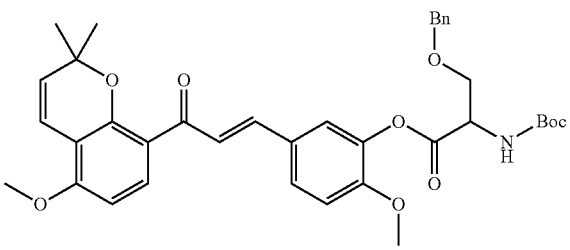 [SMILES: COc1ccc(/C=C/C(=O)c2ccc(OC)c3c2OC(C)(C)C=C3)cc1OC(=O)C(COCc1ccccc1)NC(=O)OC(C)(C)C]

(E)-2-methoxy-5-(3-(5-methoxy-2,2-dimethyl-2H-chromen-8-yl)-3-oxoprop-1-en-1-yl)phenyl 3-(benzyloxy)-2-((tert-butoxycarbonyl)amino)propanoate (SKLBC-104)

The title compound was prepared from N-Boc-O-Bn-D-serine by a procedure similar to example 77, and the yield was 61%. $^1$H NMR (400 MHz, CDCl$_3$) δ: 1.45 (s, 15H), 3.78 (s, 3H), 3.88 (s, 3H), 4.01 (m, 1H), 4.61 (s, 2H), 4.75 (d, J=8.8 Hz, 1H), 5.48 (d, J=8.8 Hz, 1H), 5.59 (d, J=10.0 Hz, 1H), 6.51 (d, J=8.8 Hz, 1H), 6.67 (d, J=10.0 Hz, 1H), 6.96 (d, J=8.4 Hz, 1H), 7.33-7.43 (m, 5H), 7.44 (d, J=7.2 Hz, 1H), 7.51 (d, J=15.6 Hz, 1H), 7.56 (d, J=15.6 Hz, 1H), 7.69 (d, J=8.8 Hz, 1H)

EXAMPLE 119

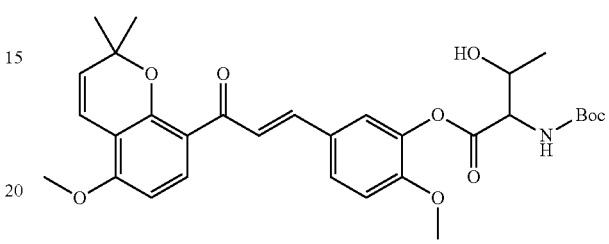

(E)-2-methoxy-5-(3-(5-methoxy-2,2-dimethyl-2H-chromen-8-yl)-3-oxoprop-1-en-1-yl)phenyl 2-((tert-butoxycarbonyl)amino)-3-hydroxybutanoate (SKLBC-105)

The title compound was prepared from N-Boc-L-threonine by a procedure similar to example 77, and the yield was 71%. $^1$H NMR (400 MHz, CDCl$_3$) δ: 1.35 (d, J=6.0 Hz, 3H), 1.43-1.49 (m, 15H), 3.88 (s, 6H), 4.57 (m, 1H), 5.36 (m, 1H), 5.63 (d, J=10.0 Hz, 1H), 6.51 (d, J=6.0 Hz, 1H), 6.69 (d, J=10.0 Hz, 1H), 7.00 (d, J=8.4 Hz, 1H), 7.35 (m, 1H), 7.46 (d, J=7.6 Hz, 1H), 7.58-0.60 (m, 2H), 7.70 (d, J=7.6 Hz, 1H)

EXAMPLE 120

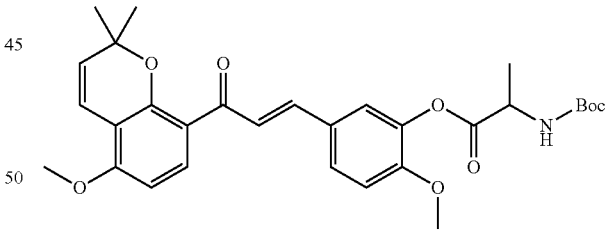

(E)-2-methoxy-5-(3-(5-methoxy-2,2-dimethyl-2H-chromen-8-yl)-3-oxoprop-1-en-1-yl)phenyl 2-((tert-butoxycarbonyl)amino)propanoate (SKLBC-106)

The title compound was prepared from N-Boc-D-alanine by a procedure similar to example 77, and the yield was 79%. $^1$H NMR (400 MHz, CDCl$_3$) δ: 1.49 (s, 15H), 1.57 (d, J=6.8 Hz, 3H), 3.88 (s, 6H), 4.62 (m, 1H), 5.14 (m, 1H), 5.62 (d, J=10.0 Hz, 1H), 6.51 (d, J=8.8 Hz, 1H), 6.67 (d, J=10.0 Hz, 1H), 6.96 (d, J=8.4 Hz, 1H), 7.32 (m, 1H), 7.44 (d, J=7.6 Hz, 1H), 7.53-7.63 (m, 2H), 7.69 (d, J=8.8 Hz, 1H)

EXAMPLE 121

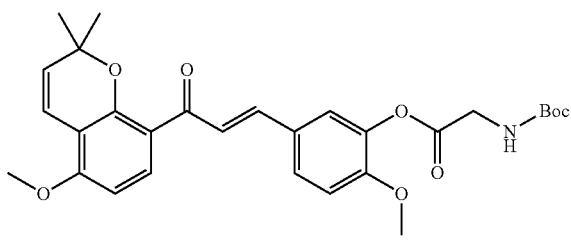 [SMILES: COc1ccc(/C=C/C(=O)c2ccc(OC)c3c2OC(C)(C)C=C3)cc1OC(=O)CNC(=O)OC(C)(C)C]

(E)-2-methoxy-5-(3-(5-methoxy-2,2-dimethyl-2H-chromen-8-yl)-3-oxoprop-1-en-1-yl)phenyl 2-((tert-butoxycarbonyl)amino)acetate (SKLBC-107)

The title compound was prepared from N-Boc-glycine by a procedure similar to example 77, and the yield was 74%. $^1$H NMR (400 MHz, CDCl$_3$) δ: 1.48 (s, 15H), 3.88 (s, 6H), 4.23 (d, J=4.4 Hz, 1H), 5.08 (m, 1H), 5.62 (d, J=10.0 Hz, 1H), 6.50 (d, J=7.6 Hz, 1H), 6.67 (d, J=10.0 Hz, 1H), 6.97 (d, J=8.0 Hz, 1H), 7.31 (m, 1H), 7.45 (d, J=8.0 Hz, 1H), 7.54 (d, J=15.6 Hz, 1H), 7.60 (d, J=15.6 Hz, 1H), 7.69 (d, J=8.0 Hz, 1H). MS(ES+): m/z: [M+H]=524.28, [M+Na]=546.26.

EXAMPLE 122

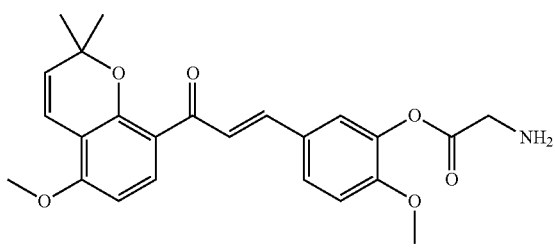 [SMILES: COc1ccc(/C=C/C(=O)c2ccc(OC)c3c2OC(C)(C)C=C3)cc1OC(=O)CN]

(E)-2-methoxy-5-(3-(5-methoxy-2,2-dimethyl-2H-chromen-8-yl)-3-oxoprop-1-en-1-yl)phenyl 2-aminoacetate (SKLBC-108)

The title compound was prepared from glycine by a procedure similar to example 77, and the yield was 75%. $^1$H NMR (400 MHz, CDCl$_3$) δ: 1.48 (s, 6H), 3.74 (m, 2H), 3.88 (s, 6H), 5.58 (d, J=10.0 Hz, 1H), 6.46 (d, J=8.4 Hz, 1H), 6.63 (d, J=10.0 Hz, 1H), 6.88 (d, J=8.0 Hz, 1H), 7.17 (m, 1H), 7.35 (d, J=5.6 Hz, 1H), 7.36-7.52 (m, 2H), 7.62 (d, J=8.0 Hz, 1H). MS(ES+) m/z: [M+H]=424.15.

EXAMPLE 123

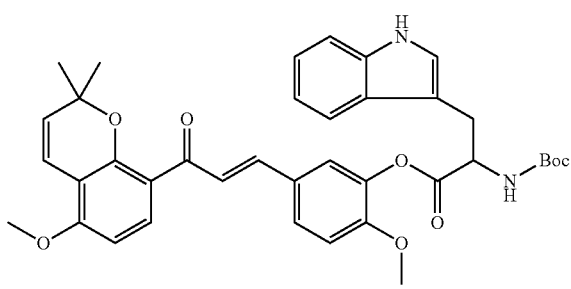 [SMILES: COc1ccc(/C=C/C(=O)c2ccc(OC)c3c2OC(C)(C)C=C3)cc1OC(=O)C(Cc1c[nH]c2ccccc12)NC(=O)OC(C)(C)C]

(E)-2-methoxy-5-(3-(5-methoxy-2,2-dimethyl-2H-chromen-8-yl)-3-oxoprop-1-en-1-yl)phenyl 2-((tert-butoxycarbonyl)amino)-3-(1H-indol-3-yl)propanoate (SKLBC-109)

The title compound was prepared from N-Boc-L-tryptophan by a procedure similar to example 77, and the yield was 75%. $^1$H NMR (400 MHz, CDCl$_3$) δ: 1.45 (s, 15H), 3.44-3.50 (m, 2H), 3.82 (s, 3H), 3.89 (s, 3H), 4.96 (m, 1H), 5.14 (d, J=8.4 Hz, 1H), 5.61 (d, J=10.0 Hz, 1H), 6.51 (d, J=8.8 Hz, 1H), 6.68 (d, J=10.0 Hz, 1H), 6.95 (d, J=8.4 Hz, 1H), 7.04 (m, 1H), 7.12-7.22 (m, 3H), 7.36 (d, J=8.0 Hz, 1H), 7.43 (d, J=8.8 Hz, 1H), 7.46 (d, J=15.6 Hz, 1H), 7.52 (d, J=15.6 Hz, 1H), 7.65 (d, J=7.6 Hz, 1H), 7.68 (d, J=9.2 Hz, 1H), 8.15 (s, 1H). MS(ES+) m/z: [M+H]=653.46.

EXAMPLE 124

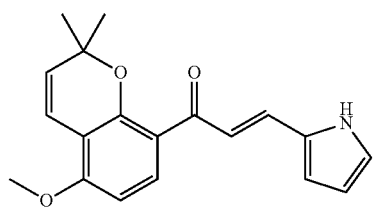 [SMILES: COc1ccc(C(=O)/C=C/c2ccc[nH]2)c2c1C=CC(C)(C)O2]

(E)-1-(5-methoxy-2,2-dimethyl-2H-chromen-8-yl)-3-(1H-pyrrol-2-yl)prop-2-en-1-one (SKLBC-110)

The title compound was prepared from 1H-pyrrole-2-carbaldehyde by a procedure similar to example 2. $^1$H NMR (400 MHz, CDCl$_3$) δ: 1.49 (s, 6H), 3.76 (s, 3H), 3.88 (s, 3H), 5.62 (d, J=10.0 Hz, 1H), 6.20 (m, 1H), 6.52 (d, J=8.8 Hz, 1H), 6.69 (d, J=10.0 Hz, 1H), 6.72 (dd, J=8.0 Hz, 1.6 Hz, 1H), 6.78 (d, 1.6 Hz, 1H), 7.52 (d, J=15.6 Hz, 1H), 7.72 (d, J=15.6 Hz, 1H), 7.24 (d, J=8.8 Hz, 1H). MS(ES+) m/z: [M+H]$^+$=310.26, [M+Na]=332.27.

EXAMPLE 125

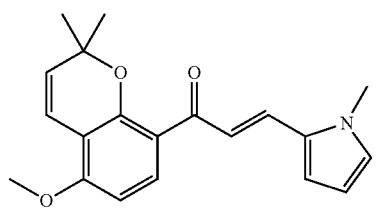

(E)-1-(5-methoxy-2,2-dimethyl-2H-chromen-8-yl)-3-(1-methyl-1H-pyrrol-2-yl)prop-2-en-1-one (SKLBC-111)

The title compound was prepared from 1-methyl-1H-pyrrole-2-carbaldehyde by a procedure similar to example 2. $^1$H NMR (400 MHz, CDCl$_3$) δ: 1.51 (s, 6H), 3.88 (s, 3H), 5.62 (d, J=10.0 Hz, 1H), 6.30-6.32 (m, 1H), 6.50 (d, J=8.8 Hz, 1H), 6.45 (m, 1H), 6.68 (d, J=10.0 Hz, 1H), 6.96 (m, 1H), 7.31 (d, J=15.6 Hz, 1H), 7.61 (d, J=15.6 Hz, 1H), 7.67 (d, J=8.8 Hz, 1H). MS(ES+) m/z: [M+H]=324.26, [M+Na]=346.26.

EXAMPLE 126

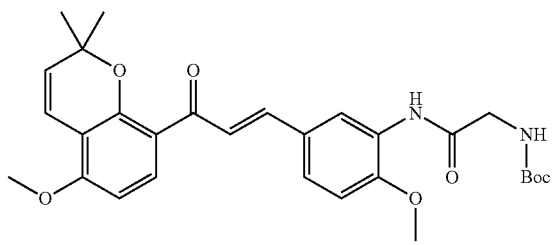 [SMILES: COc1ccc(/C=C/C(=O)c2ccc(OC)c3c2OC(C)(C)C=C3)cc1NC(=O)CNC(=O)OC(C)(C)C]

(E)-tert-butyl(2-((2-methoxy-5-(3-(5-methoxy-2,2-dimethyl-2H-chromen-8-yl)-3-oxoprop-1-en-1-yl)phenyl)amino)-2-oxoethyl)carbamate (SKLBC-112)

The title compound was prepared from Boc-glycine by a procedure similar to example 106, and the yield was 74%. $^1$H NMR (400 MHz, CDCl$_3$) δ: 8.76 (s, 1H), 8.40 (s, 1H), 7.71 (d, J=8.8 Hz, 1H), 7.66 (s, 2H), 7.29 (s, 1H), 6.89 (d, J=8.4 Hz, 1H), 6.68 (d, J=10.0 Hz, 1H), 6.51 (d, J=8.8 Hz, 1H), 5.63 (d, J=10.0 Hz, 1H), 5.20 (s, 1H), 3.96 (s, 2H), 3.92 (s, 3H), 3.88 (s, 3H), 1.54 (s, 6H), 1.49 (s, 9H).

EXAMPLE 127

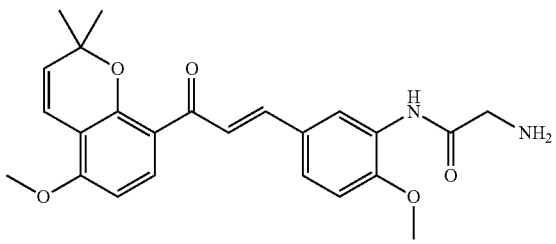 [SMILES: COc1ccc(/C=C/C(=O)c2ccc(OC)c3c2OC(C)(C)C=C3)cc1NC(=O)CN]

(E)-2-amino-N-(2-methoxy-5-(3-(5-methoxy-2,2-dimethyl-2H-chromen-8-yl)-3-oxoprop-1-en-1-yl)phenyl)acetamide (SKLBC-113)

The title compound was prepared from glycine by a procedure similar to example 106, and the yield was 75%. $^1$H NMR (400 MHz, DMSO) δ: 8.81 (d, J=1.8 Hz, 1H), 7.59 (dd, J=12.3, 3.4 Hz, 2H), 7.54 (d, J=15.7 Hz, 1H), 7.37 (dd, J=8.5, 2.0 Hz, 1H), 7.15 (d, J=8.5 Hz, 1H), 6.72 (d, J=8.9 Hz, 1H), 6.62 (d, J=10.0 Hz, 1H), 5.79 (dd, J=10.0, 4.2 Hz, 1H), 3.93 (s, 3H), 3.87 (s, 3H), 3.29 (s, 2H), 1.51 (s, 6H).

EXAMPLE 128

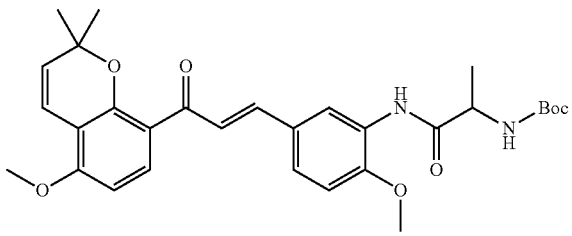 [SMILES: COc1ccc(/C=C/C(=O)c2ccc(OC)c3c2OC(C)(C)C=C3)cc1NC(=O)C(C)NC(=O)OC(C)(C)C]

(E)-tert-butyl (1-((2-methoxy-5-(3-(5-methoxy-2,2-dimethyl-2H-chromen-8-yl)-3-oxoprop-1-en-1-yl)phenyl)amino)-1-oxopropan-2-yl)carbamate (SKLBC-114)

The title compound was prepared from Boc-D-alanine by a procedure similar to example 106, and the yield was 79%. $^1$H NMR (400 MHz, CDCl$_3$) δ: 9.79 (s, 1H), 8.82 (d, J=1.9 Hz, 1H), 7.69 (d, J=8.8 Hz, 1H), 7.65 (s, 2H), 7.28 (d, J=2.1 Hz, 1H), 6.88 (d, J=8.5 Hz, 1H), 6.68 (d, J=10.0 Hz, 1H), 6.50 (d, J=8.9 Hz, 1H), 5.62 (d, J=10.0 Hz, 1H), 3.93 (s, 3H), 3.88 (s, 3H), 3.70 (dd, J=14.1, 7.5 Hz, 1H), 1.54 (s, 6H), 1.45 (d, J=7.0 Hz, 3H).

EXAMPLE 129

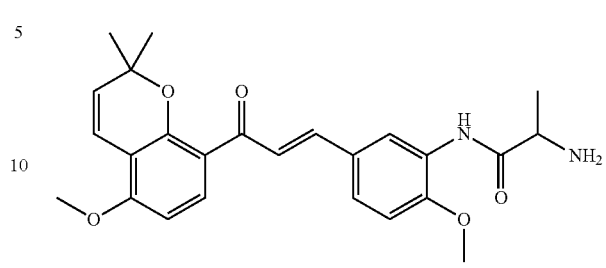

(E)-2-amino-N-(2-methoxy-5-(3-(5-methoxy-2,2-dimethyl-2H-chromen-8-yl)-3-oxoprop-1-en-1-yl)phenyl)propanamide (SKLBC-115)

The title compound was prepared from D-alanine by a procedure similar to example 106, and the yield was 64%. $^1$H NMR (400 MHz, CDCl$_3$) δ: 9.79 (s, 1H), 8.82 (d, J=1.9 Hz, 1H), 7.69 (d, J=8.8 Hz, 1H), 7.65 (s, 2H), 7.28 (d, J=2.1 Hz, 1H), 6.88 (d, J=8.5 Hz, 1H), 6.68 (d, J=10.0 Hz, 1H), 6.50 (d, J=8.9 Hz, 1H), 5.62 (d, J=10.0 Hz, 1H), 3.93 (s, 3H), 3.88 (s, 3H), 3.70 (dd, J=14.1, 7.5 Hz, 1H), 1.54 (s, 6H), 1.45 (d, J=7.0 Hz, 3H).

EXAMPLE 130

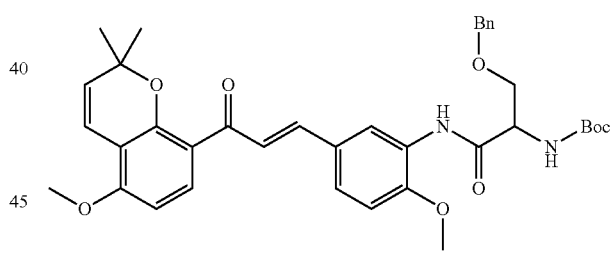

(E)-tert-butyl(3-(benzyloxy)-1-((2-methoxy-5-(3-(5-methoxy-2,2-dimethyl-2H-chromen-8-yl)-3-oxoprop-1-en-1-yl)phenyl)amino)-1-oxopropan-2-yl)carbamate (SKLBC-116)

The title compound was prepared from N-Boc-O-Bn-D-serine by a procedure similar to example 106, and the yield was 61%. $^1$H NMR (400 MHz, CDCl$_3$) δ: 8.92 (s, 1H), 8.79 (s, 1H), 7.70 (d, J=8.8 Hz, 1H), 7.65 (s, 2H), 7.36-7.27 (m, 6H), 6.84 (d, J=8.4 Hz, 1H), 6.68 (d, J=10.0 Hz, 1H), 6.50 (d, J=8.8 Hz, 1H), 5.62 (d, J=10.0 Hz, 1H), 5.55 (s, 1H), 4.60 (dd, J=26.7, 12.0 Hz, 2H), 4.46 (s, 1H), 4.02 (s, 1H), 3.88 (s, 3H), 3.70 (s, 3H), 3.66 (d, J=8.7 Hz, 1H), 1.53 (s, 6H), 1.48 (s, 9H). [M+Na]$^+$=665.3.

EXAMPLE 131

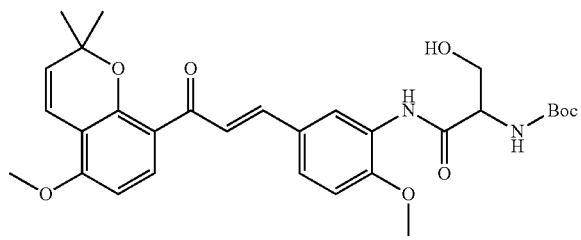 [SMILES: COc1ccc(/C=C/C(=O)c2ccc(OC)c3c2OC(C)(C)C=C3)cc1NC(=O)C(CO)NC(=O)OC(C)(C)C]

(E)-tert-butyl(3-hydroxy-1-((2-methoxy-5-(3-(5-methoxy-2,2-dimethyl-2H-chromen-8-yl)-3-oxo-prop-1-en-1-yl)phenyl)amino)-1-oxopropan-2-yl)carbamate (SKLBC-117)

The title compound was prepared from N-Boc-D-serine by a procedure similar to example 106, and the yield was 67%. $^1$H NMR (400 MHz, CDCl$_3$) δ: 9.00 (s, 1H), 8.68 (s, 1H), 7.70 (d, J=8.8 Hz, 1H), 7.64 (s, 2H), 7.29 (s, 1H), 6.87 (d, J=8.4 Hz, 1H), 6.68 (d, J=10.0 Hz, 1H), 6.50 (d, J=8.9 Hz, 1H), 5.80 (d, J=7.1 Hz, 1H), 5.63 (d, J=10.0 Hz, 1H), 4.40-4.36 (m, 1H), 4.20 (s, 1H), 4.05 (d, J=10.2 Hz, 1H), 3.88 (d, J=4.5 Hz, 6H), 3.78 (s, 1H), 1.53 (s, 3H), 1.48 (s, 3H), 1.44 (s, 9H).

EXAMPLE 132

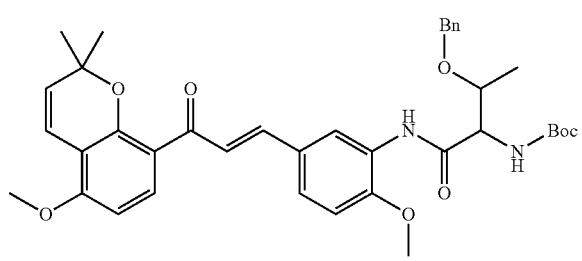 [SMILES: COc1ccc(/C=C/C(=O)c2ccc(OC)c3c2OC(C)(C)C=C3)cc1NC(=O)C(NC(=O)OC(C)(C)C)C(C)OCc1ccccc1]

(E)-tert-butyl(3-(benzyloxy)-1-((2-methoxy-5-(3-(5-methoxy-2,2-dimethyl-2H-chromen-8-yl)-3-oxo-prop-1-en-1-yl)phenyl)amino)-1-oxobutan-2-yl)carbamate (SKLBC-118)

The title compound was prepared from N-Boc-O-Bn-L-threonine by a procedure similar to example 106, and the yield was 68%. $^1$H NMR (400 MHz, CDCl$_3$) δ: 8.98 (s, 1H), 8.79 (s, 1H), 7.70 (d, J=8.7 Hz, 1H), 7.66 (s, 2H), 7.39-7.27 (m, 6H), 6.83 (d, J=8.2 Hz, 1H), 6.68 (d, J=10.0 Hz, 1H), 6.50 (d, J=8.7 Hz, 1H), 5.63 (t, J=10.3 Hz, 2H), 4.65 (s, 2H), 4.48 (s, 1H), 4.25 (s, 1H), 3.88 (s, 3H), 3.60 (s, 3H), 1.53 (s, 6H), 1.49 (s, 9H).

EXAMPLE 133

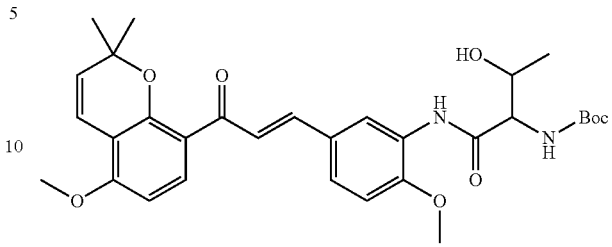

(E)-tert-butyl(3-hydroxy-1-((2-methoxy-5-(3-(5-methoxy-2,2-dimethyl-2H-chromen-8-yl)-3-oxo-prop-1-en-1-yl)phenyl)amino)-1-oxobutan-2-yl)carbamate (SKLBC-119)

The title compound was prepared from N-Boc-L-threonine by a procedure similar to example 106, and the yield was 71%. $^1$H NMR (400 MHz, CDCl$_3$) δ: 8.95 (s, 1H), 8.73 (d, J=1.9 Hz, 1H), 7.70 (d, J=8.8 Hz, 1H), 7.65 (d, J=1.4 Hz, 2H), 7.25 (d, J=1.9 Hz, 1H), 6.86 (d, J=8.5 Hz, 1H), 6.68 (d, J=10.0 Hz, 1H), 6.50 (d, J=8.9 Hz, 1H), 5.66 (d, J=8.1 Hz, 1H), 5.62 (d, J=10.0 Hz, 1H), 4.50 (d, J=5.5 Hz, 1H), 4.40 (s, 1H), 4.25 (d, J=7.8 Hz, 1H), 3.89 (s, 3H), 3.88 (s, 3H), 1.54 (d, J=2.3 Hz, 6H), 1.49 (s, 9H), 1.44 (s, 3H).

EXAMPLE 134

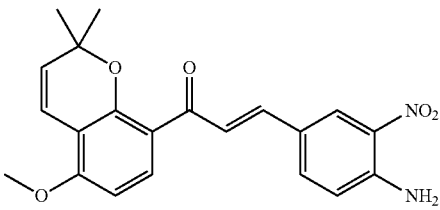 [SMILES: COc1ccc(C(=O)/C=C/c2ccc(N)c([N+](=O)[O-])c2)c2c1C=CC(C)(C)O2]

(E)-3-(4-amino-3-nitrophenyl)-1-(5-methoxy-2,2-dimethyl-2H-chromen-8-yl)prop-2-en-1-one (SKLBC-120)

The title compound was prepared from 4-amino-3-nitrobenzaldehyde by a procedure similar to example 2, and the yield was 72%. $^1$H NMR (400 MHz, CDCl$_3$) δ: 8.42 (d, J=1.4 Hz, 1H), 7.73 (d, J=8.8 Hz, 1H), 7.68 (d, J=15.7 Hz, 1H), 7.58 (dd, J=8.6, 7.0 Hz, 2H), 6.85 (d, J=8.7 Hz, 1H), 6.70 (d, J=10.0 Hz, 1H), 6.52 (d, J=8.9 Hz, 1H), 6.32 (s, 2H), 5.64 (d, J=10.0 Hz, 1H), 3.89 (s, 3H), 1.53 (s, 6H).

EXAMPLE 135

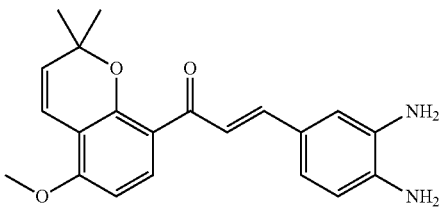

(E)-3-(3,4-diaminophenyl)-1-(5-methoxy-2,2-dimethyl-2H-chromen-8-yl)prop-2-en-1-one (SKLBC-121)

The title compound was prepared from SKLBC-120 by a procedure similar to example 98, and the yield was 60%. $^1$H NMR (400 MHz, CDCl$_3$) δ: 7.67 (d, J=8.8 Hz, 1H), 7.58 (d, J=15.7 Hz, 1H), 7.54-7.45 (m, 1H), 7.03 (dd, J=8.0, 1.3 Hz, 1H), 6.97 (s, 1H), 6.69 (d, J=9.9 Hz, 2H), 6.50 (d, J=8.8 Hz, 1H), 5.62 (d, J=10.0 Hz, 1H), 3.88 (s, 3H), 1.49 (s, 6H).

EXAMPLE 136

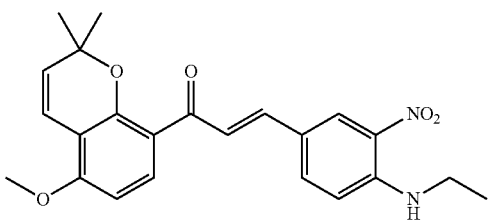

(E)-3-(4-(ethylamino)-3-nitrophenyl)-1-(5-methoxy-2,2-dimethyl-2H-chromen-8-yl)prop-2-en-1-one (SKLBC-122)

The title compound was prepared from SKLBC-120 and ethyliodide by a procedure similar to example 100, and the yield was 73%. $^1$H NMR (400 MHz, CDCl$_3$) δ: 8.48 (s, 1H), 8.21 (s, 1H), 7.74 (d, J=8.5 Hz, 1H), 7.71-7.64 (m, 2H), 7.60 (d, J=15.6 Hz, 1H), 6.90 (d, J=8.6 Hz, 1H), 6.70 (d, J=10.0 Hz, 1H), 6.53 (d, J=8.5 Hz, 1H), 5.65 (d, J=10.0 Hz, 1H), 3.89 (s, 3H), 3.49-3.35 (m, 2H), 1.54 (s, 6H), 1.40 (t, J=7.2 Hz, 3H).

EXAMPLE 137

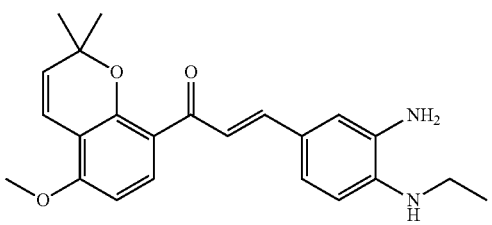 [SMILES: CCNc1ccc(/C=C/C(=O)c2ccc(OC)c3c2OC(C)(C)C=C3)cc1[N+](=O)[O-]]

(E)-3-(3-amino-4-(ethylamino)phenyl)-1-(5-methoxy-2,2-dimethyl-2H-chromen-8-yl)prop-2-en-1-one (SKLBC-123)

The title compound was prepared from SKLBC-122 by a procedure similar to example 98, and the yield was 55%. $^1$H NMR (400 MHz, CDCl$_3$) δ: 7.67 (d, J=8.8 Hz, 1H), 7.61 (d, J=15.7 Hz, 1H), 7.47 (d, J=15.6 Hz, 1H), 7.14 (dd, J=8.2, 1.4 Hz, 1H), 6.99 (d, J=1.5 Hz, 1H), 6.69 (d, J=10.0 Hz, 1H), 6.62 (d, J=8.2 Hz, 1H), 6.50 (d, J=8.8 Hz, 1H), 5.62 (d, J=10.0 Hz, 1H), 3.87 (s, 3H), 3.21 (q, J=7.1 Hz, 2H), 1.50 (s, 6H), 1.32 (t, J=7.1 Hz, 3H). [M+H]$^+$=379.32.

EXAMPLE 138

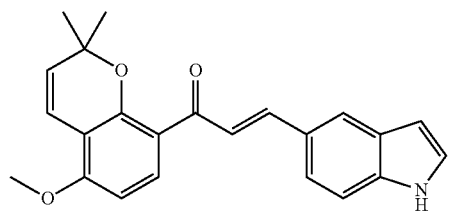 [SMILES: COc1ccc(C(=O)/C=C/c2ccc3[nH]ccc3c2)c2c1C=CC(C)(C)O2]

(E)-3-(1H-indol-5-yl)-1-(5-methoxy-2,2-dimethyl-2H-chromen-8-yl)prop-2-en-1-one (SKLBC-124)

The title compound was prepared from 1H-indole-5-carbaldehyde by a procedure similar to example 2, and the yield was 67%. $^1$H NMR (400 MHz, CDCl$_3$) δ: 8.32 (s, 1H), 7.86 (d, J=15.2 Hz, 2H), 7.71 (dd, J=12.2, 10.1 Hz, 2H), 7.52 (dd, J=8.5, 1.2 Hz, 1H), 7.40 (d, J=8.5 Hz, 1H), 7.25-7.22 (m, 1H), 6.71 (d, J=10.0 Hz, 1H), 6.60 (s, 1H), 6.52 (d, J=8.8 Hz, 1H), 5.64 (d, J=10.0 Hz, 1H), 3.89 (s, 3H), 1.52 (s, 6H).

EXAMPLE 139

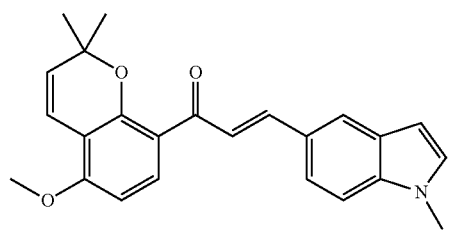 [SMILES: COc1ccc(C(=O)/C=C/c2ccc3c(ccn3C)c2)c2c1C=CC(C)(C)O2]

(E)-1-(5-methoxy-2,2-dimethyl-2H-chromen-8-yl)-3-(1-methyl-1H-indol-5-yl)prop-2-en-1-one (SKLBC-125)

The title compound was prepared from SKLBC-124 and MeI by a procedure similar to example 100, and the yield was 88%. $^1$H NMR (400 MHz, CDCl$_3$) δ: 7.90-7.83 (m, 2H), 7.70 (dd, J=12.2, 10.0 Hz, 2H), 7.55 (dd, J=8.6, 1.4 Hz, 1H), 7.33 (d, J=8.6 Hz, 1H), 7.07 (d, J=3.1 Hz, 1H), 6.71 (d, J=10.0 Hz, 1H), 6.55-6.49 (m, 2H), 5.64 (d, J=10.0 Hz, 1H), 3.88 (s, 3H), 3.80 (s, 3H), 1.52 (s, 6H).

EXAMPLE 139

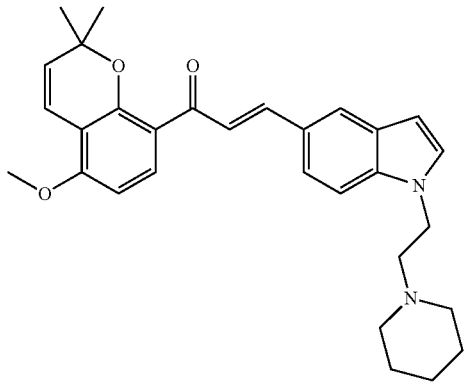 [SMILES: COc1ccc(C(=O)/C=C/c2ccc3c(ccn3CCN3CCCCC3)c2)c2c1C=CC(C)(C)O2]

(E)-1-(5-methoxy-2,2-dimethyl-2H-chromen-8-yl)-
3-(1-(2-(piperidin-1-yl)ethyl)-1H-indol-5-yl)prop-2-
en-1-one (SKLBC-126)

The title compound was prepared from SKLBC-124 and 1-(2-chloroethyl)piperidine by a procedure similar to example 100, and the yield was 91%. $^1$H NMR (400 MHz, CDCl$_3$) δ: 7.86 (d, J=15.5 Hz, 2H), 7.70 (dd, J=12.2, 10.4 Hz, 2H), 7.57-7.49 (m, 1H), 7.36 (d, J=8.6 Hz, 1H), 7.16 (d, J=3.1 Hz, 1H), 6.70 (d, J=10.0 Hz, 1H), 6.51 (dd, J=6.0, 2.7 Hz, 2H), 5.63 (d, J=10.0 Hz, 1H), 4.24 (t, J=7.2 Hz, 2H), 3.88 (s, 3H), 2.70 (t, J=7.2 Hz, 2H), 2.45 (s, 4H), 1.59 (dt, J=11.0, 5.6 Hz, 4H), 1.52 (s, 6H), 1.47-1.41 (m, 2H). [M+H]$^+$=471.3.

EXAMPLE 140

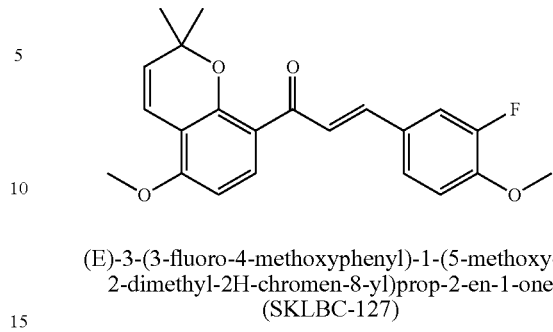

(E)-3-(3-fluoro-4-methoxyphenyl)-1-(5-methoxy-2,
2-dimethyl-2H-chromen-8-yl)prop-2-en-1-one
(SKLBC-127)

The title compound was prepared from 3-fluoro-4-methoxybenzaldehyde by a procedure similar to example 2, and the yield was 76%. $^1$H NMR (400 MHz, CDCl$_3$) δ: 7.72 (d, J=8.8 Hz, 1H), 7.59 (s, 2H), 7.35 (dd, J=12.2, 2.0 Hz, 1H), 7.32-7.28 (m, 1H), 6.97 (t, J=8.5 Hz, 1H), 6.70 (d, J=10.0 Hz, 1H), 6.52 (d, J=8.9 Hz, 1H), 5.64 (d, J=10.0 Hz, 1H), 3.93 (s, 3H), 3.88 (s, 3H), 1.51 (s, 6H). [M+H]$^+$=369.17.

Pharmacodynamics Experiment
Cell Proliferative Assay

The synthesized compounds were evaluated for their cytotoxin activity against suspended tumor cells. These cells were seeded on 96-well plates and incubated for 24 h. Selected compounds were added at various doses and incubated for 72 h, MTT was then added, and the absorbance was measured at a wavelength of 590 nm. IC$_{50}$ values are expressed as the mean±SEM from the dose-response curves of at least three independent experiments. As summarized in Table 1, Millepachine, SKLBC-4, 9, 10, 12, 14, 16, 17, 18, 28, 33, 41, 45, 46, 47, 49, 50, 52, 54, 55 possessed better inhibitory activity against tumor cells, and among these compounds, SKLBC-1 and SKLBC-45 possessed best inhibitory activity against the tumor cells including cancer cell lines coming from colon, liver, and leukemia.

TABLE 1

In vitro cell growth inhibitory effects of optimization compounds.

| Compds | IC$_{50}$s (µM) | | | | |
| --- | --- | --- | --- | --- | --- |
| | HepG2 | SW620 | HT29 | K562 | HCT116 |
| Millepachine | 2.61 | 0.76 | 3.29 | 4.56 | 4.66 |
| SKLBC-2 | >10 | >10 | >10 | >10 | >10 |
| SKLBC-3 | >10 | 9.15 | >10 | >10 | 7.65 |
| SKLBC-4 | 7.56 | 6.57 | >10 | >10 | >10 |
| SKLBC-5 | >10 | >10 | >10 | >10 | >10 |
| SKLBC-6 | >10 | >10 | >10 | >10 | >10 |
| SKLBC-7 | >10 | >10 | >10 | >10 | 1.92 |
| SKLBC-8 | >10 | >10 | >10 | >10 | 5.82 |
| SKLBC-9 | 0.73 | 0.57 | 1.87 | 3.50 | 1.63 |
| SKLBC-10 | 0.21 | 2.14 | 4.48 | 3.67 | >10 |
| SKLBC-11 | >10 | >10 | >10 | >10 | >10 |
| SKLBC-12 | 2.30 | >10 | 1.31 | 4.60 | >10 |
| SKLBC-13 | >10 | >10 | >10 | >10 | 4.53 |
| SKLBC-14 | 4.74 | >10 | >10 | >10 | 8.88 |
| SKLBC-15 | >10 | >10 | 6.6 | >10 | 8.05 |
| SKLBC-16 | 4.28 | 2.25 | 3.79 | 3.02 | >10 |
| SKLBC-17 | 2.61 | 3.52 | 3.73 | 7.77 | >10 |
| SKLBC-18 | 2.83 | 4.09 | 4.26 | 5.87 | 8.05 |
| SKLBC-19 | >10 | >10 | >10 | >10 | >10 |
| SKLBC-20 | >10 | >10 | >10 | >10 | >10 |
| SKLBC-21 | >10 | >10 | >10 | >10 | >10 |
| SKLBC-22 | >10 | >10 | >10 | >10 | >10 |
| SKLBC-23 | >10 | >10 | >10 | >10 | >10 |
| SKLBC-24 | >10 | >10 | >10 | >10 | >10 |
| SKLBC-25 | >10 | >10 | >10 | >10 | 9.71 |
| SKLBC-26 | >10 | >10 | >10 | >10 | >10 |

TABLE 1-continued

In vitro cell growth inhibitory effects of optimization compounds.

| | | | | | |
|---|---|---|---|---|---|
| SKLBC-27 | >10 | >10 | >10 | >10 | >10 |
| SKLBC-28 | 0.78 | 0.67 | 1.47 | 3.55 | 1.63 |
| SKLBC-29 | >10 | >10 | >10 | >10 | >10 |
| SKLBC-30 | >10 | >10 | >10 | >10 | >10 |
| SKLBC-31 | >10 | >10 | >10 | >10 | >10 |
| SKLBC-32 | >10 | >10 | >10 | >10 | >10 |
| SKLBC-33 | 5.76 | 5 | 2.12 | 5.40 | >10 |
| SKLBC-34 | >10 | >10 | >10 | >10 | >10 |
| SKLBC-35 | >10 | >10 | >10 | >10 | >10 |
| SKLBC-36 | >10 | >10 | >10 | >10 | >10 |
| SKLBC-37 | >10 | >10 | >10 | >10 | 9.44 |
| SKLBC-38 | >10 | >10 | >10 | >10 | 5.24 |
| SKLBC-39 | >10 | >10 | >10 | >10 | >10 |
| SKLBC-40 | >10 | >10 | >10 | >10 | >10 |

| Compds | HepG2 | A549 | A375 | SMMC-7221 | K562 | LO2 |
|---|---|---|---|---|---|---|
| SKLBC-45 | 0.148 | 0.36 | 0.62 | 0.61 | 0.522 | 20 |
| SKLBC-46 | 9.7 | 9.7 | 8.4 | >10 | 4.42 | 8.2 |
| SKLBC-47 | 0.185 | 8.45 | 0.45 | 0.23 | 0.528 | >20 |
| SKLBC-48 | >10 | 17.1 | 9.6 | >10 | 8.75 | >20 |
| SKLBC-49 | 5.55 | 6.9 | 4.1 | 8.6 | 2.92 | 8.6 |
| SKLBC-50 | 0.703 | 1.61 | 9.2 | 9.7 | 0.59 | >20 |
| SKLBC-51 | >10 | >20 | >10 | >10 | >10 | 20 |
| SKLBC-52 | 0.59 | 0.94 | 0.61 | 0.78 | 0.3165 | >10 |
| SKLBC-53 | 8.2 | >10 | 3.75 | 3.38 | 4.25 | >10 |
| SKLBC-54 | 0.533 | 0.41 | 0.2625 | 0.773 | 0.51 | >10 |
| SKLBC-55 | 1.07 | 0.5 | 0.48 | 1.62 | 1.05 | >10 |
| SKLBC-56 | 9.45 | 9.1 | >10 | 0.59 | 6.57 | >10 |
| SKLBC-57 | >10 | >10 | >10 | >10 | >10 | >20 |
| SKLBC-58 | 0.226 | 0.58 | 0.67 | 1.32 | 0.5 | >10 |
| SKLBC-59 | >10 | >10 | >10 | >10 | >10 | >20 |
| SKLBC-60 | >10 | >10 | >10 | >10 | >10 | >20 |
| SKLBC-61 | 0.44 | 0.44 | 1.05 | 1.145 | 0.58 | >10 |
| SKLBC-62 | >10 | >10 | >10 | >10 | >10 | |
| SKLBC-63 | >10 | >10 | >10 | >10 | >10 | |
| SKLBC-64 | >10 | >10 | >10 | >10 | >10 | |
| SKLBC-65 | 2.1 | 0.55 | 3.8 | 0.98 | 0.6 | >10 |
| SKLBC-66 | 0.368 | 2.36 | 0.413 | 2.34 | 1.11 | 8.4 |
| SKLBC-67 | 0.195 | 0.86 | 0.105 | 1.895 | 0.43 | 10 |
| SKLBC-68 | 0.068 | 0.8 | 0.68 | 1.62 | 0.245 | >10 |
| SKLBC-69 | 3.6 | 8.6 | 2.4 | 9.2 | 7.85 | >10 |
| SKLBC-70 | >10 | >10 | >10 | >10 | >10 | >10 |
| SKLBC-71 | 0.58 | 1.2 | 2.2 | 0.87 | 0.62 | >10 |
| SKLBC-72 | >10 | >10 | >10 | >10 | >10 | >20 |
| SKLBC-73 | >10 | >10 | >10 | >10 | >10 | >20 |
| SKLBC-74 | 0.09 | 0.226 | 0.245 | 2.735 | 0.202 | >10 |
| SKLBC-75 | 0.06 | 0.49 | 0.19 | 1.16 | 0.295 | >10 |
| SKLBC-76 | 0.103 | 0.475 | 0.4433 | 2.15 | 0.164 | >10 |
| SKLBC-77 | 9 | >10 | >10 | >10 | 9.24 | >10 |
| SKLBC-78 | 2.52 | 6.4 | 1.06 | >10 | 2.83 | 5.58 |
| SKLBC-79 | 0.09 | 1.18 | 0.3775 | 1.0325 | 0.24 | >10 |
| SKLBC-80 | 0.118 | 1.32 | 0.3825 | 1.44 | 0.41 | >10 |
| SKLBC-81 | 0.15 | 0.98 | 0.505 | 2.63 | 0.57 | >10 |
| SKLBC-82 | >10 | >10 | >10 | >10 | >10 | >20 |
| SKLBC-83 | 0.042 | 0.285 | 0.111 | 0.2775 | 0.246 | 8.5 |
| SKLBC-84 | >10 | >10 | >10 | >10 | >10 | >20 |
| SKLBC-85 | >10 | >10 | >10 | >10 | >10 | >20 |
| SKLBC-86 | >10 | >10 | >10 | >10 | >10 | >20 |
| SKLBC-87 | >10 | >10 | >10 | >10 | >10 | >20 |
| SKLBC-88 | >10 | >10 | >10 | >10 | 7.5 | 9.7 |
| SKLBC-89 | 0.05 | 0.215 | 0.215 | 0.245 | 0.093 | 2.65 |
| SKLBC-90 | 4.85 | 10 | 3.94 | >10 | 9.28 | >10 |
| SKLBC-91 | >10 | >10 | >10 | >10 | 0.57 | >10 |
| SKLBC-92 | 2.85 | 5 | 2.15 | 2.24 | 3.5 | >10 |
| SKLBC-93 | 4.55 | >10 | 4.6 | 5.1 | 2.4 | 7.8 |
| SKLBC-94 | >10 | >10 | >10 | >10 | >10 | >20 |
| SKLBC-95 | >10 | >10 | >10 | >10 | >10 | >20 |
| SKLBC-96 | >10 | >10 | >10 | >10 | >10 | >20 |
| SKLBC-97 | >10 | >10 | >10 | >10 | >10 | >10 |
| SKLBC-98 | 3.6 | 8.6 | 2.4 | 9.2 | 7.85 | >10 |
| SKLBC-99 | 10 | >10 | 9 | 5.6 | 8.85 | 9.8 |
| SKLBC-100 | >10 | >10 | >10 | >10 | >10 | >20 |
| SKLBC-101 | >10 | >10 | >10 | 6.8 | >10 | >10 |
| SKLBC-102 | >10 | >10 | >10 | >10 | >10 | >20 |

In Vivo Antitumor Activity
(1) In Malignant Melanoma B16 Tumor Xenograft Study of Millepachine Six-week-old female mice were obtained from Chinese Academy of Medical Science (Beijing, China). B16F10 cells ($5 \times 10^5$ in 100 μl saline) were injected subcutaneously into the right flanks of C57 mice. When the tumor reached about 100 $mm^3$, mice were selected and randomly divided into four groups including control and three compounds-treated groups. The animals were intravenous injection with Millepachine (5, 10 and 15 mg/kg) or vehicle once every other day for seven times. Tumor burden was measured every 2 or 3 days with a caliper (calculated volume $[mm^3] = \pi/6 \times length \times width \times width$). After treatment, mice were killed tumors were collected and weighted. The results were shown in FIGS. 1, 2 and 3.

At the end of treatment, we found that treatment with respective 5, 10 and 15 mg/kg Millepachine could suppress tumor growth and prolong the survivor time of tumor-bearing mice in comparison with control group (P<0.01).

(2) The Effect of Millepachine on the Malignant Melanoma B16-Induced Lung Metastasis Six-week-old female mice were obtained from Chinese Academy of Medical Science (Beijing, China). B16F10 cells ($5 \times 10^5$ in 100 μl saline) were injected intravenous into the caudal vein of C57 mice. The animals were intravenous injection with Millepachine (7.5 and 15 mg/kg) or vehicle once every other day for seven times after incubation of cell. After stop treatment for 20 days, mice were killed and lung metastasis was observed. The results were shown in FIG. 4. As shown in FIG. 4, Millepachine significantly inhibited the lung metastasis.

(3) In Vivo Anti-Tumor Activity of SKLBC-9 on Human Lung Cancer A549 Xenograft

Six-week-old female mice were obtained from Chinese Academy of Medical Science (Beijing, China). A549 cells ($5 \times 10^6$ in 100 μl saline) were injected subcutaneously into the right flanks of Balbc mice. When the tumor reached about 100 $mm^3$, mice were selected and randomly divided into five groups including control, cisplatin (1.5 mg/kg) and SKLBC-9 (5,10,20 mg/kg). The animals were intravenous injection with SKLBC-9 (5, 10 and 20 mg/kg) or vehicle once three days for eight times. Tumor burden was measured every 2 or 3 days with a caliper (calculated volume $[mm^3] = n/6 \times length \times width \times width$). After treatment, mice were killed and tumors were collected and weighted. The results were shown in FIGS. 5 and 6. At the end of treatment, we found that treatment with respective 5, 10 and 20 mg/kg SKLBC-9 could suppress tumor growth in comparison with control group (P<0.01).

(4) In Vivo Anti-Tumor Activity of SKLBC-9 on Human Lung Cancer SPC-A1 Xenograft Six-week-old Balb/c nude mice were obtained from Chinese Academy of Medical Science (Beijing, China). SPC-A1 cells ($5 \times 10^6$ in 100 μl saline) were injected subcutaneously into the right flanks of the mice. 14 days after cell injection, forty mice were selected and randomly divided into four groups including control, cisplatin (1.5 mg/kg) and SKLBC-9 (10, 20 mg/kg). The animals were intravenously injected with SKLBC-9 or vehicle every three days for eight times. Tumor burden and animal body weight was measured every 2 or 3 days. The survival rate was also recorded. After treatment, mice were killed and tumors were collected and weighted. The results were shown in FIGS. 7 and 8.

At the end of treatment, we found that treatment with SKLBC-9 significantly inhibited the growth of tumor compared to vehicle control group. Meanwhile, the average tumor weight of SKLBC-9 treatment group was significantly lower than that of the vehicle control group.

(5) In Vivo Anti-Tumor Activity of SKLBC-45 on Human Hepatocarcinoma HepG2 Xenograft Six-week-old Balb/c nude mice were obtained from Chinese Academy of Medical Science (Beijing, China). HepG2 cells ($10^7$ in 100 μl saline) were injected subcutaneously into the right flanks of the mice. 14 days after cell injection, seventy mice were selected and randomly divided into seven groups including saline control, vehicle control, four doses of SKLBC-45 (2.5, 5, 10, 20 mg/kg) and positive control Adriamycin (5 mg/kg). The animals were intravenously injected with saline, SKLBC-45, adriamycin or vehicle every three days for eight times. Tumor burden and animal body weight was measured every 2 or 3 days. The survival rate was also recorded. After treatment, mice were killed and tumors were collected and weighted. The results were shown in FIGS. 9 and 10.

At the end of treatment, we found that treatment with SKLBC-45 significantly inhibited the growth of tumor compared to vehicle control group. Meanwhile, the average tumor weight of SKLBC-45 treatment groups was significantly lower than that of the vehicle control group.

(6) In Vivo Anti-Tumor Activity of SKLBC-76 on Human Hepatocarcinoma HepG2 Xenograft Six-week-old Balb/c nude mice were obtained from Chinese Academy of Medical Science (Beijing, China). HepG2 cells ($10^7$ in 100 μl saline) were injected subcutaneously into the right flanks of the mice. 14 days after cell injection, fifty mice were selected and randomly divided into five groups including control, three doses of SKLBC-76 (2.5, 5, 10 mg/kg) and positive control taxol (5 mg/kg). The animals were intravenously injected with SKLBC-76 or taxol every three days for eight times. Tumor burden and animal body weight was measured every 2 or 3 days. The survival rate was also recorded. After treatment, mice were killed and tumors were collected and weighted. The results were shown in FIGS. 11 and 12.

At the end of treatment, we found that treatment with SKLBC-76 significantly inhibited the growth of tumor compared to control group. Meanwhile, the average tumor weight of SKLBC-76 treatment groups was significantly lower than that of the control group.

(7) In Vivo Anti-Tumor Activity of SKLBC-83 on C26-Tumor Bearing Mice Model.

Six-week-old Balb/c mice were obtained from Chinese Academy of Medical Science (Beijing, China). C26 cells ($3 \times 10^6$ in 100 μl saline) were injected subcutaneously into the right flanks of the mice. 10 days after cell injection, thirty mice were selected and randomly divided into three groups including saline control, SKLBC-83 (10 mg/kg) and positive control taxol (5 mg/kg). The animals were intravenously injected with SKLBC-76 or taxol every two days for eight times. Tumor burden and animal body weight was measured every 2 or 3 days. The survival rate was also recorded. After treatment, mice were killed and tumors were collected and weighted. The results were shown in FIGS. 13 and 14.

At the end of treatment, we found that treatment with SKLBC-83 significantly inhibited the growth of tumor compared to control group. Meanwhile, the average tumor weight of SKLBC-83 treatment groups was significantly lower than that of the control group.

(8) In Vivo Anti-Tumor Activity of SKLBC-45, SKLBC-68, SKLBC-74, SKLBC-75, SKLBC-76, SKLBC-79, SKLBC-80 on C26-Tumor Bearing Mice Model.

Six-week-old Balb/c mice were obtained from Chinese Academy of Medical Science (Beijing, China). C26 cells (3×10⁶ in 100 μl saline) were injected subcutaneously into the right flanks of the mice. 10 days after cell injection, when the average tumor volume reached ~60 mm³. Fifty-four mice were selected and randomly divided into nine groups including saline control, seven compounds and positive control taxol (5 mg/kg). The treatment started one day later. The animals were intravenously injected with SKLBC-45, SKLBC-68, SKLBC-74, SKLBC-75, SKLBC-76, SKLBC-79, SKLBC-80 (all 10 mg/kg) or taxol every two days for eight times. Tumor burden and animal body weight was measured every 2 or 3 days. The survival rate was also recorded. After treatment, mice were killed and tumors were collected and weighted. The results were shown in FIGS. 15, 16, 17, 18, 19, 20 and 21.

At the end of treatment, we found that treatment with SKLBC-83 significantly inhibited the growth of tumor compared to control group. Meanwhile, the average tumor weight of SKLBC-83 treatment groups was significantly lower than that of the control group.

The invention claimed is:

1. A compound of Formula I:

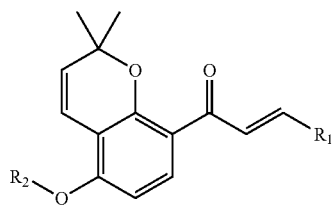

I wherein:

$R_1$ is an aromatic ring, unsubstituted or substituted with one or more substituents selected from the group consisting of: halogen, hydroxyl, —SH, C1-C10 alkoxy, C1-C4 aminoalkyl, halogen substituted C1-C5 alkyl, C1-10 alkyl, $NO_2$, cyano,

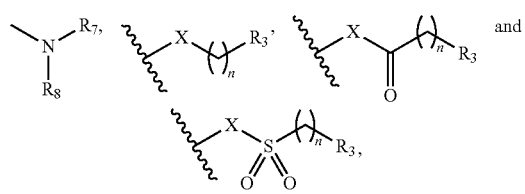

wherein:

X is O, S or NH;

n=0-4;

$R_7$ and $R_8$ are each independently selected from the group consisting of: hydrogen, C1-C6 aliphatic hydrocarbon, C3-C10 cyclic alkyl, —OH, C1-C10 carbonyl,

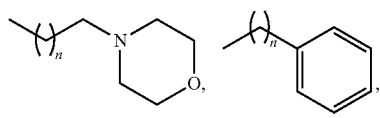

wherein n=0-4;

$R_3$ is selected from the group consisting of: hydrogen, C1-5 hydrocarbon, halogen, halogen substituted C1-C5 alkyl, hydroxyl, C3-C10 cyclic alkyl, C1-C5 alkoxy, C1-4 cyclic alkoxy, hydroxylamine, hydroxyl amide, carboxyl, trifluoromethyl, C3-C7 aliphatic heterocyclic ring,

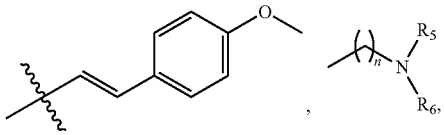

C5-C7 aromatic ring wherein:

the C5-C7 aromatic ring is substituted with one or more substituents selected from the group consisting of: halogen, C1-3 alkoxy and trifluoromethyl;

n=0-4; and $R_5$ and $R_6$ are each independently selected from the group consisting of: hydrogen, C1-C4 aliphatic alkyl, and phenyl; and $R_2$ is selected from the group consisting of: C1-C10 aliphatic hydrocarbon,

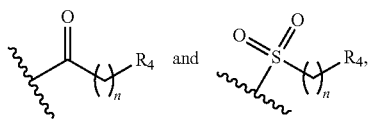

wherein:

n=0-4; and $R_4$ is selected from the group consisting of: C1-C10 aliphatic hydrocarbon, C3-C10 cyclic alkyl,

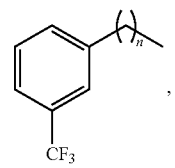

an aromatic ring, wherein:

n=0-4; and the aromatic ring is substituted with one or more substituents selected from the group consisting of: H, halogen, —SH, —OH, hydroxylamine, hydroxyl amide, carboxyl, cyano, —$NO_2$, —$CF_3$, C1-10 alkyl, and C1-10 alkyoxy.

2. The compound of claim 1, wherein $R_1$ is the unsubstituted or substituted aromatic ring with 5-11 carbon atoms.

3. The compound of claim 1, wherein $R_1$ is the unsubstituted or substituted aromatic ring with 6-10 carbon atoms.

4. The compound of claim 3, wherein the unsubstituted or substituted aromatic ring of $R_1$ is a benzene or naphthalene ring.

5. The compound of claim 1, wherein $R_7$ and $R_8$ are each independently: hydrogen, C1-C6 aliphatic hydrocarbon,

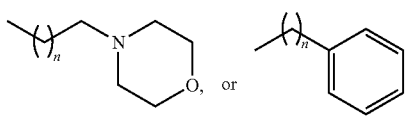

wherein n=0-2.

6. The compound of claim 5 wherein $R_3$ is selected from the group consisting of: linear or branched, saturated or unsaturated C1-5 hydrocarbon, C1-C3 alkoxy, hydroxyl, C3-C10 cyclic alkyl, C3-C7 aliphatic heterocyclic ring with one or more hetero atom comprising N or O, and

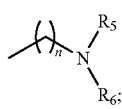

wherein n=0-4; and $R_5$ and $R_6$ are each independently hydrogen or C1-C4 aliphatic alkyl.

7. The compound of claim 6 wherein $R_3$ is C1-C4 hydrocarbon, C3-C10 cyclic alkyl, or C5-C7 aryl.

8. The compound of claim 6 wherein $R_3$ is C1-C4 hydrocarbon, C3-C10 cyclic alkyl, or benzene.

9. The compound of claim 1 wherein $R_2$ is

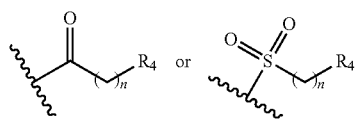

and n=1-4.

10. The compound of claim 1 wherein $R_2$ is C1-C4 alkyl.

11. The compound represented by formula II

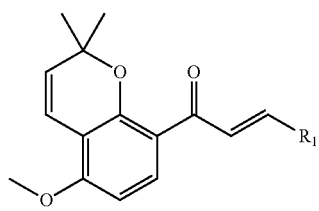

II wherein:

$R_1$ is a unsubstituted or substituted aromatic ring with one or more substituents selected from the group consisting of: halogen, SH, hydroxylamine, hydroxy amide, carboxyl, C1-C4 alkyl carbonyl oxygen, C1-C4 aminoalkyl, OH, C1-C4 alkanes amide, cyano, $NO_2$,

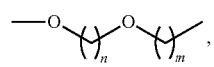

$CF_3$, C1-C4 alkyl, C1-C4 alkoxy, wherein $R_3$ is C1-C4 alkyl or C5-C7 alkyl aromatic ring; n=1-4, m=0-7.

12. The compound represented by formula III:

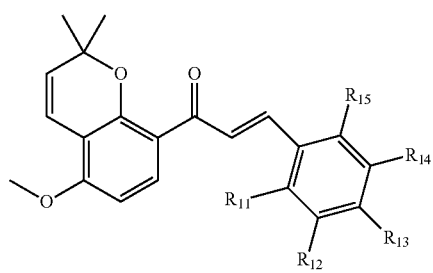

III wherein $R_{11}$-$R_{15}$ are independently H, halogen, SH, hydroxylamine, hydroxy amide, carboxyl, C1-C4 alkyl carbonyl oxygen, C1-C4 alkylation amino, OH, C1-C4 alkanes amide, cyano, $NO_2$,

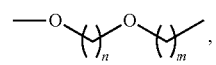

$CF_3$, C1-C4 alkyl, C1-C4 alkoxy, C5-C7 alkyl aromatic ring, $NH(R_3)_2$; wherein $R_3$ is C1-C4 alkyl or C5-C7 alkyl aromatic ring; n=1-4, m=0-7.

13. The compound of claim 12 wherein $R_{11}$-$R_{15}$ are independently H, F, Cl, Br, OH, SH, carboxyl, C1-C4 silane oxygen carbonyl, C1-C4 alkylation amino, $NO_2$,

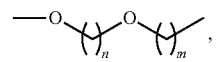

$CF_3$, C1-C4 alkyl, C1-C4 alkoxy, C5-C7 alkyl aromatic ring, $NH(R_3)_2$; wherein $R_3$ is C1-C4 alkyl or C5-C7 alkyl aromatic ring; n=1-4, m=0-7.

14. The compound of claim 13 wherein $R_{11}$-$R_{15}$ are independently H, F, Cl, Br, OH, SH, C1-C4 alkylation amino, $NO_2$,

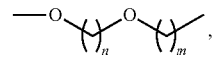

$CF_3$, C1-C4 alkyl, C1-C4 alkoxy, C5-C7 alkyl aromatic ring, $NH(R_3)_2$; wherein $R_3$ is C1-C4 alkyl or benzene; n=1, m=0-4.

15. The compound of claim 14 wherein $R_{11}$-$R_{15}$ are independently H, F, Cl, Br, OH, $NO_2$,

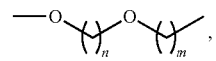

$CF_3$, C1-C4 alkyl, C1-C4 alkoxy, C5-C7 alkyl aromatic ring, $NH(R_3)_2$; wherein $R_3$ is C1-C4 alkyl or benzene; n=1, m=0-4.

16. The compound of claim 1, wherein $R_1$ is substituted and the compound is represented by formula IV:

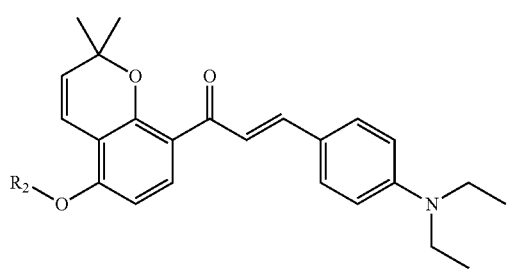

wherein $R_2$ is hydrogen, C1-C6 linear or branched alkyl, C2-C6 alkenyl or alkynyl, C1-C3 alkyl with one or more substituents selected from: hydroxyl, amino or halogen, atom, C3-C6 cyclic alkyl, aralkyl not replace or various substituted phenyl, aromatic heterocyclic ring; C1-C6 linear or branched alkyl ester, with one or more selected from hydroxyl, amino and halogen atom C1-C3 alkyl ester, ring of C3-C6 alkyl esters, aralkyl not replace or various substituted phenyl ester, aromatic heterocyclic base ester; C1-C6 linear or branched chain sulfonic acid ester, with one or more selected from hydroxyl, amino and halogen atom C1-C3 sulfonic acid ester, C3-C6 ring alkyl sulfonate, aralkyl not replace or substituted phenyl sulfonic acid ester, aromatic heterocyclic sulfonic acid ester.

17. The compound of claim 1, wherein $R_1$ is substituted and the compound is represented by formula V:

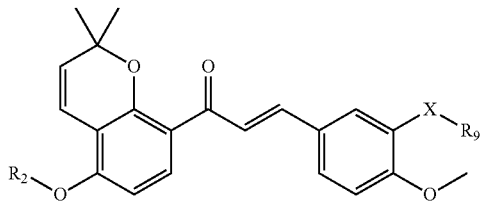

wherein X is N, O or S;

$R_9$ is hydrogen, C1-C6 linear or branched alkyl, C2-C6 alkenyl or alkynyl, C1-C3 alkyl with one or more substituents selected from hydroxyl, amino, halogen atom, C3-C6 naphthenic base, aralkyl not replace or various substituted phenyl, aromatic heterocyclic base; C1-C6 linear or branched alkyl ester, with one or more selected from hydroxyl, amino and halogen atom C1-C3 alkyl ester, ring of C3-C6 alkyl esters, aralkyl not replace or various substituted phenyl ester, aromatic heterocyclic base ester; C1-C6 linear or branched chain sulfonic acid ester, with one or more selected from hydroxyl, amino and halogen atom C1-C3 sulfonic acid ester, C3-C6 ring alkyl sulfonate, aralkyl not replace or substituted phenyl sulfonic acid ester, aromatic heterocyclic base sulfonic acid ester; C3-C6 amino acid base.

18. The compound of claim 1 with the formula:

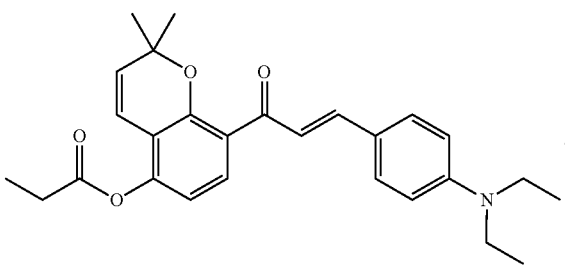

19. The compound of claim 1 with the formula:

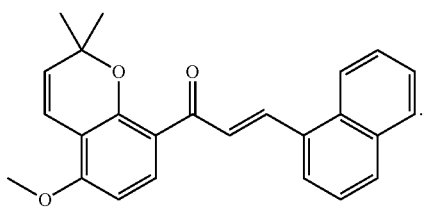 [SMILES: COc1ccc(C(=O)/C=C/c2cccc3ccccc23)c2c1C=CC(C)(C)O2]

* * * * *